(12) United States Patent
Montclare et al.

(10) Patent No.: US 9,617,525 B2
(45) Date of Patent: Apr. 11, 2017

(54) PHOSPHOTRIESTERASE ENZYMES, METHODS AND COMPOSITIONS RELATED THERETO

(71) Applicant: New York University, New York, NY (US)

(72) Inventors: Jin Kim Montclare, New York, NY (US); Richard Bonneau, New York, NY (US); P. Douglas Renfrew, New York, NY (US); Ching-Yao Yang, Elmhurst, NY (US); Carlo Yuvienco, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/804,277

(22) Filed: Jul. 20, 2015

(65) Prior Publication Data

US 2016/0083702 A1 Mar. 24, 2016

Related U.S. Application Data

(60) Provisional application No. 62/026,579, filed on Jul. 18, 2014.

(51) Int. Cl.
*C12N 9/16* (2006.01)
*C12Q 1/44* (2006.01)

(52) U.S. Cl.
CPC ............... *C12N 9/16* (2013.01); *C12Q 1/44* (2013.01); *C12Y 301/08* (2013.01)

(58) Field of Classification Search
CPC ....................................................... C12N 9/16
See application file for complete search history.

(56) References Cited

U.S. PATENT DOCUMENTS

2004/0161818 A1* 8/2004 Horne ................ C12N 9/16
435/69.1

OTHER PUBLICATIONS

Baker et al., Abstracts, 40th Mid. Atlantic Regional Meeting of ACS, Queens, NY, USA, May 17-21, 2008, ACS, Washington DC.*
Voloshchuk et al., Incorporation of unnatural amino acids for synthetic biology, Mol. BioSys. 2010, 6, 65-80.
More et al., Posttranslational Modification of Proteins Incorporating Nonnatural Amino Acids, Functional Polymers by Post-Polymerization Modification . . . , GWiley-VCH Verlag GmbH, 2013.
Tang et al., Fluorinated Coiled-Coil Proteins Prepared in Vivo Display Enhanced Thermal and Chemical Stability, Angew. Chem. Int. Ed. 2001, 40, 1494-1496.
Tang et al., Biosynthesis of a Highly Stable Coiled-Coil Protein Containing Hexafluoroleucine in an Engineered Bacterial Host, J. Am. Chem. Soc. 2001, 123, 11089-11090.
Montclare et al., Biosynthesis and Stability of Coiled-Coil Peptides Containing (2S,4R)-5,5,5-Trifluoroleucine and (2S,4S)-5,5,5-Trifluoroleucine, ChemBioChem 2009, 10, 84-86.
Son, Stabilization of bzip Peptides through Incorporation of Fluorinated Aliphatic Residues, ChemBioChem 2006, 7, 1251-1257.
Voloshchuk et al., Positional effects of monofluorinated phenylalanines on histone acetyltransferase stability and activity, Bioorg. Med. Chem. Lett. 2009, 19, 5449-5451.
Panchenko et al., Influence of Global Fluorination on Choloramphenicol Acetyltransferase Activity and Stability, Biotech. Bioeng. 2006, 94, 921-930.
Voloshchuk et al., BFluorinated chloramphenicol acetyltransferase thermostability and activity profile: Improved thermostability by a single-isoleucine mutant, Bioorg. Med. Chem. Lett. 2007, 17, 5907-5911.
Mehta et al., Modulating substrate specificity of histone acetyltransferase with unnatural amino acids, Mol. BioSyst. 2011, 7, 3050-3055.
Hammill et al., Preparation of site-specifically labeled fluorinated proteins for 19F-NMR structural characterization, Nature Prot. 2007, 2, 2601-2607.
Budisa et al., Residue-specific global fluroination of Candida antarctica lipase B in Pichia pastoris, Mol. BioSys. 2010, 5, 1630-1639.
Hoesl et al., Lipase Congeners Designed by Genetic Code Engineering, ChemCatChem 2011, 3, 213-221.
Merkel et al., Parallel Incorporation of Different Fluorinated Amino Acids: on the Way to Teflon Proteins, ChemBioChem 2010, 11, 1505-1507.
Holzberger et al., Replacing 32 Proline Residues by a Noncanonical Amino Acid Results in a Highly Active DNA Polymerase, J. Am. Chem. Soc. 2010, 132, 15708-15713.
Yuvienco et al., Modulating Supramolecular Assemblies and Mechanical Properties of Engineered Protein Materials by Fluorinated Amino Acids, Biomacromolecules 2012, 13, 2273-2278.
Montclare et al., Evolving Proteins of Novel Composition, Angew. Chem. Int. Ed. 2006, 45, 4518-4521.
Baker et al., Enhanced Refoldability and Thermoactivity of Fluorinated Phosphotriesterase, ChemBioChem 2011, 12, 1845-1848.
Leaver-Fay et al., ROSETTA3: An Object-Oriented Software Suite for the Simulation and Design of Macromolecules, Methods Enzymol. 2011, 487, 545-574.
Davis et al., ROSETTALIGAND Docking with Full Ligand and Receptor Flexibility, J. Mol. Biol. 2009, 385, 381-392.
Davis et al., Blind docking of pharmaceutically relevant compounds using RosettaLigand, Protein Sci. 2009, 18, 1998-2002.

(Continued)

*Primary Examiner* — Maryam Monshipouri
(74) *Attorney, Agent, or Firm* — Hodgson Russ LLP

(57) ABSTRACT

The instant invention provides methods and related compositions for identifying polypeptides with improved stability and/or enzymatic activity in comparison to native forms, wherein the identified polypeptides comprise one or more non-natural amino acids. In certain embodiments, the present invention relates to novel phosphotriesterase enzymes comprising one or more non-natural amino acids. In a particular embodiment, the instant invention provides novel phosphotriesterase enzymes with greater stability and/or enhanced activity in comparison to native forms of the enzyme. The present invention also relates to compositions comprising novel phophotriesterase enzymes, such as prophylactics, decontaminants, animal feedstocks, and assay kits.

14 Claims, 32 Drawing Sheets

(56) References Cited

OTHER PUBLICATIONS

Miklos et al., Structure-Based Design of Supercharged, Highly Thermoresistant Antibodies, Chem. Biol. 2012, 19, 449-455.
Dantas et al., a Large Scale Test of Computational Protein Design: Folding and Stability of Nine Completely Redesigned Globular Proteins, J. Mol. Biol. 2003, 332, 449-460.
Dantas et al., High-resolution Structural and Thermodynamic Analysis of Extreme Stabilization of Human Procarboxypeptidase by Computational Protein Design, J. Mol. Biol. 2007, 366, 1209-1221.
Joachimiak et al., Computational Design of a New Hydrogen Bond Network and at Least a 300-fold Specificity Switch at a Protein-Protein Interface, J. Mol. Biol. 2006, 361, 195-208.
Stranges et al., Computational design of a symmetric homodimer using B-strand assembly, Proc. Natl. Acad. Sci. USA 2011, 108, 20562-20567.
Kuhlman et al., Design of a Novel Globular Protein Fold with Atomic-Level Accuracy, Science 2003, 302, 1364-1368.
Richter et al., De Novo Enzyme Design Using Rosetta3, PloS One 2011, 6, e19230.
Khare et al., Computational redesign of a mononuclear zinc metalloenzyme for organophosphate hydrolysis, Nature Chem. Biol. 2012, 8, 294-300.
Renfrew et al., Incorporation of Noncanonical Amino Acids into Rosetta and Use in Computational Protein-Peptide Interface Design, PloS One 2012, 7, e32637.
Benning et al., High Resolution X-ray Structures of Different Metal-Substituted Forms of Phosphotriesterase from Pseudomonas diminuta Biochemistry 2001, 40, 2712-2272.
Chaudhury et al., PyRosetta: a script-based interface for implementing molecular modeling algorithms using Rosetta, Bioinformatics 2010, 26, 689-691.
Grimsley et al., Organophosphorus Hydrolase Is a Remarkably Stable Enzyme That Unfolds through a Homodimeric Intermediate, Biochemistry 1997, 36, 14366-14374.
Fan et al., Thermal unfolding of *Escherichia coli* trigger factor studied by ultra-sensitive differential scanning aalorimetry, Biochim. Biophys. Acta 2008, 1784, 1728-1734.
Tsytlonok et al., The how's and whys of protein folding intermediates, Arch. Biochem. Biophys 2013, 531, 14-23.
Yoo et al., Evolution of a fluorinated green fluorescent protein, Proc. Natl. Acad. Sci. USA 2007, 104, 13887-13890.
Khersonsky et al., Optimization of the in silico designed Kemp eliminase KE70 by computational design and directed evolution, J. Mol. Biol. 2011, 407, 391-412.
Bloom et al., Evolving strategies for enzyme engineering, Curr. Op. Struct. Biol. 2005, 15, 447-452.
Brustad et al., Optimizing Non-natural Protein Function with Directed Evolution, Curr. Op. Chem. Biol. 2011, 15, 201-210.
Hill et al., Stereochemical Specificity of Organophosphorus Acid Anhydrolase toward p-Nitrophenyl Analogs of Soman and Sarin, Bioorganic Chemistry, 2001, 29(1), pp. 27-35.
Li et al., Stereoselective Detoxification of Chiral Sarin and Soman Analogues by Phosphotriesterase, Bioorganic and Medicinal Chemistry, 2001, 9(8), pp. 2083-2091.
Li et al., Enzymatic Synthesis of Chiral Organophosphothioates from Prochiral Precursors, J. Am. Chem. Soc. 2002, 124(14), pp. 3498-3499.
Raushel et al., Phosphotriesterase: An Enzyme in Search of its Natural Substrate, Advances in Enzymology, vol. 14, 2000, 74 pp. 51-93.
Raushel, Bacterial detoxification of organophosphate nerve agents, Current Opinion in Microbiology, 2002, 5(3), 288-295.
Griffiths et al., Directed evolution of an extremely fast phosphotriesterase by in vitro compartmentalization, Embo Journal, 2003, 22(1), 24-35.
Hill et al., Enhanced Degradation of Chemical Warfare Agents through Molecular Engineering of the Phosphotriesterase Active Site, J. Am. Chem. Soc. 2003, 125(30), 8990-8991.
Li et al., Operational Control of Stereoselectivity during the Enzymatic Hydrolysis of Racemic Organophosphorus compounds, J. Am. Chem. Soc. 2003, 125(25), 7526-7527.
Aubert et al., Mechanism for the Hydrolysis of Organophosphates by the Bacterial Phosphotriesterase, Biochemistry, 2004, 43, 5707-5715.
Hong et al., Control of Stereoselectivity in Phosphotriesterase, Protein Engineering, 2004, 388, 256-266.
Li et al., Enzymatic Resolution of Chiral Phosphinate Esters, J. Am. Chem. Soc. 2004, 126(29), pp. 8888-8889.
Raushel, Engineered Variants of Phosphotriesterase for Enhanced Detoxification of Organophosphate Nerve Agents, Toxicology and Applied Pharmacology 2004, 197(3), 171.
Ghanem et al., Detoxification of organophosphate nerve agents by bacterial phosphotriesterase, Toxicol. Appl. Pharmacol. 2005, 207(2 Suppl), 459-470.
Tsai et al., Stereoselective Hydrolysis of Organophosphate Nerve Agents by the Bacterial Phosphotriesterase, Biochemistry, 2010, 49(37), 7978-1987.
Tsai et al., Structural Determinants for the Stereoselective Hydrolysis of Chiral Substrates by Phosphotriesterase, Biochemistry 2010, 49(37), 7988-7997.
Roodveldt et al., Shared Promiscuous Activities and Evolutionary Features in Various Members of the Amidohydrolase Superfamily, Biochemistry 2005, 44(38), 12728-12736.
Seibert et al., Structural and Catalytic Diversity within the Amidohydrolase Superfamily, Biochemistry 2005, 44(17), 6383-6391.
Holm et al., Protein folds and families: sequence and structure alignments, Nucleic Acids Research, 1999, 27(1), 244-7.
Benning et al., High Resolution X-ray Structures of Different Metal-Substituted Forms of Phosphotriesterase from Pseudomonas diminuta, Biochemistry 2001, 40(9), 2712-2722.
Chen-Goodspeed et al., Structural Determinants of the Substrate and Stereochemical Specificity of Phosphotriesterase, Biochemistry 2001, 40(5), 1325-1331.
Hong et al., Stereochemical Constraints on the Catalytic Hydrolysis of Organophosphate Nerve Agents by Phosphotriesterase, Phosphorus Sulfur and Silicon and the Related Elements, 1999, 146, 521-524.
Donarski et al., Structure-Activity Relationships in the Hydrolysis of Substrates by the Phosphotriesterase from Pseudomonas diminuta, Biochemistry 1989, 28, 4650-4655.
Dumas et al., Purification and Properties of the Phosphotriesterase from Pseudomonas diminuta, Journal of Biological Chemistry, 1989, 264(33), pp. 19659-19665.

\* cited by examiner

FIGURE 3

The intensity of peaks identified from MALDI-TOF.

| MALDI-TOF of pFF-S5 and pFF-104A | | | |
|---|---|---|---|
| m/z | PTE | pFF-PTE | pFFF-104A |
| | Intensity | | |
| 1096.716 | 45900.57 | 4258 | 13296 |
| 1114 (1096 with 1 pFF) | - | 90652 | 8382 |
| 1132 (1096 with 2 pFF) | - | 12818 | 57667 |
| 1861.671 | 38639.06 | 6515 | 13053 |
| 1879 (1861 with pFF) | - | 49885 | 39563 |
| 2266.393 | 32616.02 | 2241 | 1262 |
| 2284 (2266 with pFF) | - | 16629 | 3797 |

FIGURE 4

Protein yield of PTE, 104A, pFF-PTE, and pFF-104A.

| Protein Yield and Percent Incorporation | | | |
|---|---|---|---|
| Protein | Purified (mg) | Lysate (mg) | % pFF Incorporation* |
| PTE | 0.94 | 1.87 | - |
| 104A | 1.86 | 1.94 | - |
| pFF-PTE | 0.20 | 0.92 | 92 |
| pFF-104A | 0.40 | 1.27 | 80 |

All expressed in 250 mL of medium. *Calculated from MALDI-TOF Analysis.

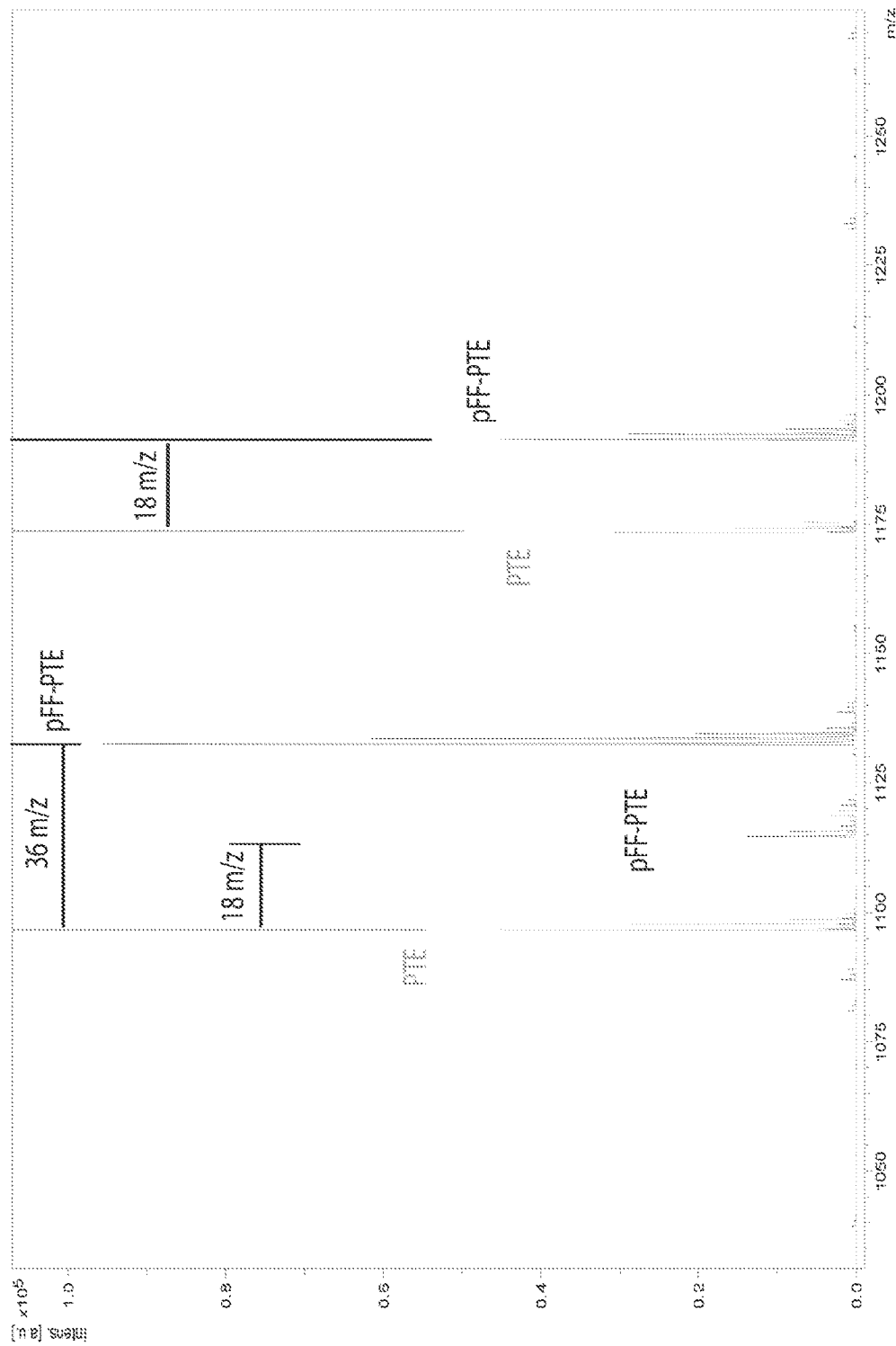

FIGURE 7

| Kinetics of paraoxon hydrolysis as a function of temperature | | | | | |
|---|---|---|---|---|---|
| Protein | | 25 °C | 35 °C | 45 °C | 55 °C |
| PTE | $k_{cat}/K_M$ $[x10^6 M^{-1} s^{-1}]$ | 2.00 ± 0.13 | 0.76 ± 0.11 | 0.72 ± 0.12 | 0.46 ± 0.18 |
| | $k_{cat}$ $[s^{-1}]$ | 2.1 ± 0.4 | 1.3 ± 0.1 | 1.4 ± 0.1 | 0.9 ± 0.1 |
| pFF-PTE | $k_{cat}/K_M$ $[x10^6 M^{-1} s^{-1}]$ | 3.27 ± 0.11 | 2.42 ± 0.10 | 1.84 ± 0.21 | 0.80 ± 0.09 |
| | $k_{cat}$ $[s^{-1}]$ | 6.0 ± 1.1 | 5.6 ± 0.1 | 4.0 ± 1.1 | 2.0 ± 0.9 |
| F104A | $k_{cat}/K_M$ $[x10^6 M^{-1} s^{-1}]$ | 0.23 ± 0.04 | 0.21 ± 0.03 | NA | NA |
| | $k_{cat}$ $[s^{-1}]$ | 0.1 ± 0.0 | 0.1 ± 0.0 | NA | NA |
| pFF-F104A | $k_{cat}/K_M$ $[x10^6 M^{-1} s^{-1}]$ | 2.23 ± 0.15 | 1.94 ± 0.18 | 1.49 ± 0.20 | 1.11 ± 0.09 |
| | $k_{cat}$ $[s^{-1}]$ | 3.3 ± 0.3 | 3.3 ± 0.6 | 2.6 ± 1.0 | 2.0 ± 0.7 |

FIGURE 9

| Kinetics of paraoxon hydrolysis as a function of time | | | | | |
|---|---|---|---|---|---|
| Protein | | Day 1 | Day 2 | Day 3 | Day 7 |
| PTE | $k_{cat}/K_M$ $[x10^6 M^{-1} s^{-1}]$ | 2.06 ± 0.23 | 1.89 ± 0.23 | 1.53 ± 0.18 | 0.89 ± 0.10 |
| | $k_{cat} [s^{-1}]$ | 2.5 ± 0.5 | 0.97 ± 0.03 | 0.23 ± 0.01 | 0.10 ± 0.01 |
| pFF-PTE | $k_{cat}/K_M$ $[x10^6 M^{-1} s^{-1}]$ | 3.53 ± 0.12 | 2.01 ± 0.28 | 1.62 ± 0.21 | 1.13 ± 0.09 |
| | $k_{cat} [s^{-1}]$ | 6.23 ± 0.97 | 3.23 ± 0.88 | 2.13 ± 0.94 | 1.46 ± 0.97 |
| F104A | $k_{cat}/K_M$ $[x10^6 M^{-1} s^{-1}]$ | 0.18 ± 0.02 | NA | NA | NA |
| | $k_{cat} [s^{-1}]$ | 0.11 ± 0.02 | NA | NA | NA |
| pFF-F104A | $k_{cat}/K_M$ $[x10^6 M^{-1} s^{-1}]$ | 1.83 ± 0.21 | 1.72 ± 0.20 | 1.43 ± 0.13 | 1.20 ± 0.10 |
| | $k_{cat} [s^{-1}]$ | 2.25 ± 0.32 | 2.03 ± 0.31 | 1.61 ± 0.25 | 1.43 ± 0.25 |

FIGURE 10
a)
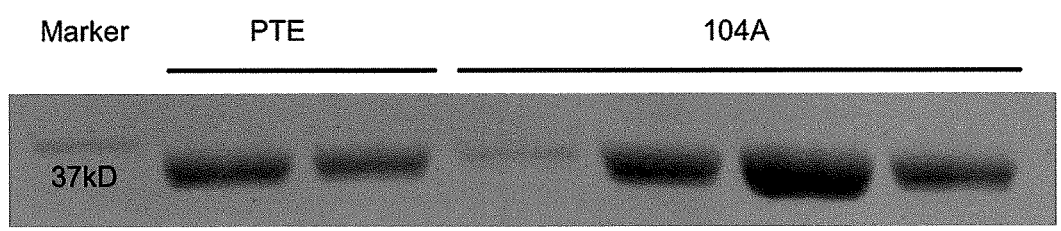
b)
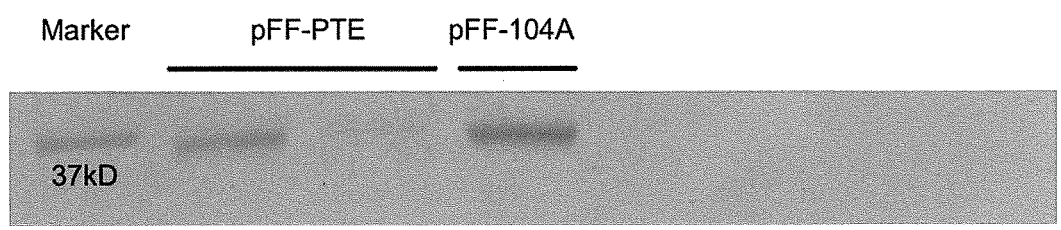

FIGURE 12

| Nano-DSC of proteins. | | |
|---|---|---|
| Protein | $T_m1$ (°C) | $T_m2$ (°C) |
| PTE | 41.3 ± 0.2 | 48.0 ± 0.2 |
| 104A | 41.5 ± 0.2 | 48.2 ± 0.3 |
| pFF-PTE | 42.0 ± 0.1 | 48.6 ± 0.2 |
| pFF-104A | - | 49.7 ± 0.2 |

FIGURE 13

(A)  Wildtype PTE protein sequence (SEQ ID NO: 1):
MRGSHHHHHHMITNSGDRINTVRGPITISEAGFTLTHEHICGSSAGFLRAWPEFFGSRKA
LAEKAVRGLRRARAAGVRTIVDVSTFDIGRDVSLLAEVSRAADVHIVAATGLWFDPPLS
MRLRSVEELTQFFLREIQYGIEDTGIRAGIIKVATTGKATPFQELVLRAAARASLATGVPV
TTHTAASQRGGEQQAAIFESEGLSPSRVCIGHSDDTDDLSYLTALAARGYLIGLDHIPHS
AIGLEDNASASALLGIRSWQTRALLIKALIDQGYMKQILVSNDWLFGFSSYVTNIMDVM
DSVNPDGMAFIPLRVIPFLREKGVPQETLAGITVTNPARFLSPTLRAS (pFF-PTE: replace all "F" with "X"; X: para-fluoro-phenylalanine)

(B)  Wildtype PTE DNA sequence (SEQ ID NO: 2):
ATGAGAGGATCGCATCACCATCACCATCACGGATCCATGATCACCAACAGCGGCGA
TCGGATCAATACCGTGCGCGGTCCTATCACAATCTCTGAAGCGGGTTTCACACTGAC
TCACGAGCACATCTGCGGCAGCTCGGCAGGATTCTTGCGTGCTTGGCCAGAGTTCTT
CGGTAGCCGCAAAGCTCTAGCGGAAAAGGCTGTGAGAGGATTGCGCCGCGCCAGAG
CGGCTGGCGTGCGAACGATTGTCGATGTGTCGACTTCGATATCGGTCGCGATGTCA
GTTTATTGGCCGAGGTTTCGCGGGCTGCCGACGTTCATATCGTGGCGGCGACCGGCT
TGTGGTTCGACCCGCCACTTTCGATGCGATTGAGGAGTGTAGAGGAACTCACACAGT
TCTTCCTGCGTGAGATTCAATATGGCATCGAAGACACCGGAATTAGGGCGGGCATTA
TCAAGGTCGCGACCACAGGCAAGGCGACCCCCTTTCAGGAGTTAGTGTTAAGGGCG
GCCGCCCGGGCCAGCTTGGCCACCGGTGTTCCGGTAACCACTCACACGGCAGCAAG
TCAGCGCGGTGGTGAGCAGCAGGCCGCCATTTTTGAGTCCGAAGGCTTGAGCCCCTC
ACGGGTTTGTATTGGTCACAGCGATGATACTGACGATTTGAGCTATCTCACCGCCCT
CGCTGCGCGCGGATACCTCATCGGTCTAGACCACATCCCGCACAGTGCGATTGGTCT
AGAAGATAATGCGAGTGCATCAGCCCTCCTGGGCATCCGTTCGTGGCAAACACGGG
CTCTCTTGATCAAGGCGCTCATCGACCAAGGCTACATGAAACAAATCCTCGTTTCGA
ATGACTGGCTGTTCGGGTTTTCGAGCTATGTCACCAACATCATGGACGTGATGGATA
GCGTGAACCCCGACGGGATGGCCTTCATTCCACTGAGAGTGATCCCATTCCTACGAG
AGAAGGGCGTCCCACAGGAAACGCTGGCAGGCATCACTGTGACTAACCCGGCGCGG
TTCTTGTCACCGACCTTGCGGGCGTCATGA

FIGURE 14

(A) F104A-PTE protein sequence (SEQ ID NO: 3):

MRGSHHHHHHMITNSGDRINTVRGPITISEAGFTLTHEHICGSSAGFLRAWPEFFGSRKA
LAEKAVRGLRRARAAGVRTIVDVSTADIGRDVSLLAEVSRAADVHIVAATGLWFDPPLS
MRLRSVEELTQFFLREIQYGIEDTGIRAGIIKVATTGKATPFQELVLRAAARASLATGVPV
TTHTAASQRGGEQQAAIFESEGLSPSRVCIGHSDDTDDLSYLTALAARGYLIGLDHIPHS
AIGLEDNASASALLGIRSWQTRALLIKALIDQGYMKQILVSNDWLFGFSSYVTNIMDVM
DSVNPDGMAFIPLRVIPFLREKGVPQETLAGITVTNPARFLSPTLRAS (pFF-PTE: replace all "F" with "X"; X: para-fluoro-phenylalanine)

(B) F104A-PTE DNA sequence (SEQ ID NO: 4):

ATGAGAGGATCGCATCACCATCACCATCACGGATCCATGATCACCAACAGCGGCGA
TCGGATCAATACCGTGCGCGGTCCTATCACAATCTCTGAAGCGGGTTTCACACTGAC
TCACGAGCACATCTGCGGCAGCTCGGCAGGATTCTTGCGTGCTTGGCCAGAGTTCTT
CGGTAGCCGCAAAGCTCTAGCGGAAAAGGCTGTGAGAGGATTGCGCCGCGCCAGAG
CGGCTGGCGTGCGAACGATTGTCGATGTGTCGACTGCCGATATCGGTCGCGATGTCA
GTTTATTGGCCGAGGTTTCGCGGGCTGCCGACGTTCATATCGTGGCGGCGACCGGCT
TGTGGTTCGACCCGCCACTTTCGATGCGATTGAGGAGTGTAGAGGAACTCACACAGT
TCTTCCTGCGTGAGATTCAATATGGCATCGAAGACACCGGAATTAGGGCGGGCATTA
TCAAGGTCGCGACCACAGGCAAGGCGACCCCCTTTCAGGAGTTAGTGTTAAGGGCG
GCCGCCCGGGCCAGCTTGGCCACCGGTGTTCCGGTAACCACTCACACGGCAGCAAG
TCAGCGCGGTGGTGAGCAGCAGGCCGCCATTTTTGAGTCCGAAGGCTTGAGCCCCTC
ACGGGTTTGTATTGGTCACAGCGATGATACTGACGATTTGAGCTATCTCACCGCCCT
CGCTGCGCGCGGATACCTCATCGGTCTAGACCACATCCCGCACAGTGCGATTGGTCT
AGAAGATAATGCGAGTGCATCAGCCCTCCTGGGCATCCGTTCGTGGCAAACACGGG
CTCTCTTGATCAAGGCGCTCATCGACCAAGGCTACATGAAACAAATCCTCGTTTCGA
ATGACTGGCTGTTCGGGTTTTCGAGCTATGTCACCAACATCATGGACGTGATGGATA
GCGTGAACCCCGACGGGATGGCCTTCATTCCACTGAGAGTGATCCCATTCCTACGAG
AGAAGGGCGTCCCACAGGAAACGCTGGCAGGCATCACTGTGACTAACCCGGCGCGG
TTCTTGTCACCGACCTTGCGGGCGTCATGA

FIGURE 15

Mutant PTE "SOBA" protein sequence (SEQ ID NO: 5):

M G D R I N T V R G P I T I S E A G F T L T H E H I C G S S S̲ G F L R R̲ W P E F F G S R
K A L A E K A V R G L R R A R A A G V R T I V D V A̲ T A̲S I G E D̲ A̲ S L L A E V S R A
A D V H I V A A T G S̲ W F D A̲S L S L̲ R L R S V E E L T Q F F L R H I Q Y G I E D T G I
R A G I I K V A T T G K A T P F Q E L V L R A A A R A S L A T G V P V T T H T A A S Q
R G G E Q Q A A I F E S E G L S P S R V C I G H S D D T D D L S Y L T A L A A R G Y L I
G L D H I P H S A I G L E D N A S A S A L L G I R S W Q T R A L L I K A L I D Q G Y M
K Q I L V S N D W L F G F S S Y V T N I M D V M D S V N P D G M A F I P L R V I P F L
R E K G V P Q E T L A G I T V T N P A R F L S P T L R A S (pFF-SOBA: replace all "F" with "X"; X: para-fluoro-phenylalanine)

FIGURE 16

Mutant PTE protein sequences (SEQ ID NOS: 6-13):

SEQ ID NO: 6

MRGSHHHHHHMITNSGDRINTVRGPITISEAG<u>L</u>TLTHEHICGSSAGFLRAWPEFFGSRKA
LAEKAVRGLRRARAAGVRTIVDVSTFDIGRDVSLLAEVSRAADVHIVAATGLWFDPPLS
MRLRSVEELTQFFLREIQYGIEDTGIRAGIIKVATTGKATPFQELVLRAAARASLATGVPV
TTHTAASQRGGEQQAAIFESEGLSPSRVCIGHSDDTDDLSYLTALAARGYLIGLDHIPHS
AIGLEDNASASALLGIRSWQTRALLIKALIDQGYMKQILVSNDWLFGFSSYVTNIMDVM
DSVNPDGMAFIPLRVIPFLREKGVPQETLAGITVTNPARFLSPTLRAS
(pFF-PTE: replace all "F" with "X"; X: para-fluoro-phenylalanine)

SEQ ID NO: 7

MRGSHHHHHHMITNSGDRINTVRGPITISEAGFTLTHEHICGSSAGFLRAWPEFFGSRKA
LAEKAVRGLRRARAAGVRTIVDVSTFDIGRDVSLLAEVSRAADVHIVAATGLWFDPPLS
MRLRSVEELTQF<u>M</u>LREIQYGIEDTGIRAGIIKVATTGKATPFQELVLRAAARASLATGVP
VTTHTAASQRGGEQQAAIFESEGLSPSRVCIGHSDDTDDLSYLTALAARGYLIGLDHIPH
SAIGLEDNASASALLGIRSWQTRALLIKALIDQGYMKQILVSNDWLFGFSSYVTNIMDV
MDSVNPDGMAFIPLRVIPFLREKGVPQETLAGITVTNPARFLSPTLRAS
(pFF-PTE: replace all "F" with "X"; X: para-fluoro-phenylalanine)

SEQ ID NO: 8

MRGSHHHHHHMITNSGDRINTVRGPITISEAGFTLTHEHICGSSAGFLRAWPEFFGSRKA
LAEKAVRGLRRARAAGVRTIVDVSTFDIGRDVSLLAEVSRAADVHIVAATGLWFDPPLS
MRLRSVEELTQFFLREIQYGIEDTGIRAGIIKVATTGKATPFQELVLRAAARASLATGVPV
TTHTAASQRGGEQQAAI<u>L</u>ESEGLSPSRVCIGHSDDTDDLSYLTALAARGYLIGLDHIPHS
AIGLEDNASASALLGIRSWQTRALLIKALIDQGYMKQILVSNDWLFGFSSYVTNIMDVM
DSVNPDGMAFIPLRVIPFLREKGVPQETLAGITVTNPARFLSPTLRAS
(pFF-PTE: replace all "F" with "X"; X: para-fluoro-phenylalanine)

SEQ ID NO: 9

MRGSHHHHHHMITNSGDRINTVRGPITISEAGFTLTHEHICGSSAGFLRAWPEFFGSRKA
LAEKAVRGLRRARAAGVRTIVDVSTFDIGRDVSLLAEVSRAADVHIVAATGLWFDPPLS
MRLRSVEELTQFFLREIQYGIEDTGIRAGIIKVATTGKATPFQELVLRAAARASLATGVPV
TTHTAASQRGGEQQAAIFESEGLSPSRVCIGHSDDTDDLSYLTALAARGYLIGLDHIPHS
AIGLEDNASASALLGIRSWQTRALLIKALIDQGYMKQILVSNDWL<u>L</u>GFSSYVTNIMDVM
DSVNPDGMAFIPLRVIPFLREKGVPQETLAGITVTNPARFLSPTLRAS
(pFF-PTE: replace all "F" with "X"; X: para-fluoro-phenylalanine)

FIGURE 16 (cont.)

SEQ ID NO: 10

MRGSHHHHHHMITNSGDRINTVRGPITISEAGFTLTHEHICGSSAGFLRAWPEFFGSRKA
LAEKAVRGLRRARAAGVRTIVDVSTFDIGRDVSLLAEVSRAADVHIVAATGLWFDPPLS
MRLRSVEELTQFFLREIQYGIEDTGIRAGIIKVATTGKATPFQELVLRAAARASLATGVPV
TTHTAASQRGGEQQAAIFESEGLSPSRVCIGHSDDTDDLSYLTALAARGYLIGLDHIPHS
AIGLEDNASASALLGIRSWQTRALLIKALIDQGYMKQILVSNDWLFG<u>L</u>SSYVTNIMDVM
DSVNPDGMAFIPLRVIPFLREKGVPQETLAGITVTNPARFLSPTLRAS
(pFF-PTE: replace all "F" with "X"; X: para-fluoro-phenylalanine)

SEQ ID NO: 11

MRGSHHHHHHMITNSGDRINTVRGPITISEAGFTLTHEHICGSSAGFLRAWPEFFGSRKA
LAEKAVRGLRRARAAGVRTIVDVSTFDIGRDVSLLAEVSRAADVHIVAATGLWFDPPLS
MRLRSVEELTQFFLREIQYGIEDTGIRAGIIKVATTGKATPFQELVLRAAARASLATGVPV
TTHTAASQRGGEQQAAIFESEGLSPSRVCIGHSDDTDDLSYLTALAARGYLIGLDHIPHS
AIGLEDNASASALLGIRSWQTRALLIKALIDQGYMKQILVSNDWLFGFSSYVTNIMDVM
DSVNPDGMA<u>L</u>IPLRVIPFLREKGVPQETLAGITVTNPARFLSPTLRAS
(pFF-PTE: replace all "F" with "X"; X: para-fluoro-phenylalanine)

SEQ ID NO: 12

MRGSHHHHHHMITNSGDRINTVRGPITISEAGFTLTHEHICGSSAGFLRAWPEFFGSRKA
LAEKAVRGLRRARAAGVRTIVDVSTFDIGRDVSLLAEVSRAADVHIVAATGLWFDPPLS
MRLRSVEELTQFFLREIQYGIEDTGIRAGIIKVATTGKATPFQELVLRAAARASLATGVPV
TTHTAASQRGGEQQAAIFESEGLSPSRVCIGHSDDTDDLSYLTALAARGYLIGLDHIPHS
AIGLEDNASASALLGIRSWQTRALLIKALIDQGYMKQILVSNDWLFGFSSYVTNIMDVM
DSVNPDGMAFIPLRVIP<u>M</u>LREKGVPQETLAGITVTNPARFLSPTLRAS
(pFF-PTE: replace all "F" with "X"; X: para-fluoro-phenylalanine)

SEQ ID NO: 13

MRGSHHHHHHMITNSGDRINTVRGPITISEAGFTLTHEHICGSSAGFLRAWPEFFGSRKA
LAEKAVRGLRRARAAGVRTIVDVSTFDIGRDVSLLAEVSRAADVHIVAATGLWFDPPLS
MRLRSVEELTQFFLREIQYGIEDTGIRAGIIKVATTGKATPFQELVLRAAARASLATGVPV
TTHTAASQRGGEQQAAIFESEGLSPSRVCIGHSDDTDDLSYLTALAARGYLIGLDHIPHS
AIGLEDNASASALLGIRSWQTRALLIKALIDQGYMKQILVSNDWLFGFSSYVTNIMDVM
DSVNPDGMAFIPLRVIPFLREKGVPQETLAGITVTNPARLLSPTLRAS
(pFF-PTE: replace all "F" with "X"; X: para-fluoro-phenylalanine)

non-PTE gene
+ pNPB + neutral red

PTE gene
+ pNPB + neutral red

FIGURE 23

Table 1. Chlorpyrifos binding scores for unique sequences with improved binding energies over the wild type PTE.
Scores are ensemble averages given in REU (Rosetta Energy Units).

A. PTE-chlorpyrifos docked conformation 1

| Sequence ID Number | Binding score [REU] | Δ WT [REU] | Residue positions mutated from wild type sequence |
|---|---|---|---|
| 14 | -9.2688 | -3.9978 | 60:VAL 106:GLY 131:SER 132:TRP 233:SER 254:GLY 257:LEU 271:TRP 302:TYR 303:GLY 306:ASP 308:GLY 309:GLY 317:ARG 136:ALA |
| 15 | -8.9544 | -3.6834 | 60:VAL 106:SER 131:SER 132:TRP 233:ASN 254:GLY 257:PHE 271:TRP 302:TYR 303:ALA 306:MET 308:ALA 309:GLY 317:LEU 136:ALA |
| 16 | -8.5154 | -3.2444 | 60:VAL 106:LEU 131:GLY 271:TRP 302:TYR 303:CYS 306:ASN 308:LEU 309:GLY 317:HIS 136:GLY |
| 17 | -8.2021 | -2.9311 | 60:VAL 106:THR 131:GLY 132:MET 233:GLU 254:ASN 257:ALA 271:TRP 302:TYR 303:ALA 306:ILE 308:PHE 309:GLY 317:HIS 136:ALA |
| 18 | -8.1061 | -2.8351 | 60:VAL 106:LEU 131:GLY 132:LEU 254:ALA 271:TRP 302:TYR 303:CYS 306:LEU 308:ALA 309:GLY 317:HIS 136:TRP |
| 19 | -8.0206 | -2.7496 | 106:GLN 131:GLY 271:TRP 302:TYR 303:GLY 306:LEU 308:ALA 309:GLY 317:HIS 136:ALA |
| 20 | -7.9296 | -2.6586 | 60:MET 106:THR 131:GLY 132:TRP 271:TRP 302:TYR 303:SER 306:ASN 308:LEU 309:GLY 317:GLU 136:ALA |
| 21 | -7.9085 | -2.6375 | 60:VAL 106:GLN 131:GLY 271:TRP 302:TYR 303:GLY 306:MET 308:ALA 309:GLY 317:ILE 136:ALA |
| 22 | -7.8713 | -2.6003 | 60:ALA 106:SER 131:GLY 132:TRP 271:TRP 302:TYR 303:SER 306:VAL 308:ILE 309:GLY 317:HIS 136:ALA |
| 23 | -7.7927 | -2.5217 | 60:VAL 106:SER 132:ALA 271:TRP 303:ALA 306:GLY 308:ASN 317:TRP 136:GLY |

FIGURE 23 (cont.)

B. PTE-chlorpyrifos docked conformation 2

| Sequence ID Number | Binding score [REU] | Δ WT [REU] | Residue positions mutated from wild type sequence |
|---|---|---|---|
| 24 | -9.3380 | -3.9076 | 60:MET 106:GLN 131:GLY 132:TRP 233:SER 254:SER 257:TRP 271:TRP 303:GLY 306:ALA 308:ALA 309:GLY 317:TYR 136:ALA |
| 25 | -9.0051 | -3.5747 | 60:CYS 106:GLN 131:GLY 132:ASN 254:CYS 257:TRP 271:TRP 302:TYR 303:GLY 306:ALA 308:ALA 309:GLY 317:LEU 136:ALA |
| 26 | -8.8582 | -3.4278 | 60:VAL 106:ALA 132:ALA 257:PHE 271:TRP 303:HIS 306:GLY 308:GLY 317:HIS 136:SER |
| 27 | -8.6783 | -3.2479 | 106:GLN 131:GLY 132:LEU 254:GLN 257:PHE 271:TRP 302:TYR 303:ALA 306:LEU 308:ALA 309:GLY 317:HIS 136:ALA |
| 28 | -8.4665 | -3.0361 | 60:VAL 106:GLN 131:GLY 132:PRO 233:ASN 254:ALA 271:TRP 302:TYR 303:ALA 306:LEU 308:ASN 309:GLY 317:HIS 136:GLY |
| 29 | -8.3672 | -2.9368 | 106:GLY 131:SER 132:TRP 254:SER 257:LYS 271:TRP 302:TYR 303:ALA 306:LEU 308:ALA 309:GLY 317:HIS 136:ALA |
| 30 | -8.3631 | -2.9327 | 60:ALA 106:GLN 131:GLY 132:TRP 254:GLN 271:TRP 302:TYR 303:PRO 306:VAL 308:ALA 309:GLY 317:VAL 136:SER |
| 31 | -8.2796 | -2.8492 | 60:ALA 106:ASP 131:GLY 132:PRO 254:ASN 257:PHE 271:TRP 302:TYR 303:PRO 306:LEU 308:ALA 309:GLY 317:VAL 136:ALA |
| 32 | -8.2702 | -2.8398 | 106:MET 132:ILE 257:PHE 271:TRP 303:ALA 306:LEU 308:ALA 317:LEU 136:GLU |
| 33 | -8.2329 | -2.8025 | 60:PHE 106:MET 131:GLY 132:TRP 254:ALA 271:TRP 302:TYR 303:SER 306:MET 308:ALA 309:GLY 317:HIS 136:ALA |

FIGURE 24

Mutant PTE protein sequences (SEQ ID NOS: 14-33):

SEQ ID NO: 14

DRINTVRGPITISEAGFTLTHEHICVSSAGFLRAWPEFFGSRKALAEKAVRGLRRARAAG
VRTIVDVSTFDGGRDVSLLAEVSRAADVHIVAATGLSWDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDSTDDLSYLTALAARGYLIGLDGIPLSAIGLEDNASASAWLGIR
SWQTRALLIKALIDQGYMKQILVSNDYGFGDSGGVTNIMDVRDSVNPDGMAFIPLRVIP
FLREKGVPQETLAGITVTNPARFLSPTLRAS
(pFF-PTE: replace all "F" with "X"; X: para-fluoro-phenylalanine)

SEQ ID NO: 15

DRINTVRGPITISEAGFTLTHEHICVSSAGFLRAWPEFFGSRKALAEKAVRGLRRARAAG
VRTIVDVSTFDSGRDVSLLAEVSRAADVHIVAATGLSWDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDNTDDLSYLTALAARGYLIGLDGIPFSAIGLEDNASASAWLGI
RSWQTRALLIKALIDQGYMKQILVSNDYAFGMSAGVTNIMDVLDSVNPDGMAFIPLRVI
PFLREKGVPQETLAGITVTNPARFLSPTLRAS
(pFF-PTE: replace all "F" with "X"; X: para-fluoro-phenylalanine)

SEQ ID NO: 16

DRINTVRGPITISEAGFTLTHEHICVSSAGFLRAWPEFFGSRKALAEKAVRGLRRARAAG
VRTIVDVSTFDLGRDVSLLAEVSRAADVHIVAATGLGFDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDHIPHSAIGLEDNASASAWLGI
RSWQTRALLIKALIDQGYMKQILVSNDYCFGNSLGVTNIMDVHDSVNPDGMAFIPLRVI
PFLREKGVPQETLAGITVTNPARFLSPTLRAS
(pFF-PTE: replace all "F" with "X"; X: para-fluoro-phenylalanine)

FIGURE 24 (cont.)

SEQ ID NO: 17

DRINTVRGPITISEAGFTLTHEHICVSSAGFLRAWPEFFGSRKALAEKAVRGLRRARAAG
VRTIVDVSTFDTGRDVSLLAEVSRAADVHIVAATGLGMDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDETDDLSYLTALAARGYLIGLDNIPASAIGLEDNASASAWLGI
RSWQTRALLIKALIDQGYMKQILVSNDYAFGISFGVTNIMDVHDSVNPDGMAFIPLRVIP
FLREKGVPQETLAGITVTNPARFLSPTLRAS
(pFF-PTE: replace all "F" with "X"; X: para-fluoro-phenylalanine)

SEQ ID NO: 18

DRINTVRGPITISEAGFTLTHEHICVSSAGFLRAWPEFFGSRKALAEKAVRGLRRARAAG
VRTIVDVSTFDLGRDVSLLAEVSRAADVHIVAATGLGLDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDAIPHSAIGLEDNASASAWLGI
RSWQTRALLIKALIDQGYMKQILVSNDYCFGLSAGVTNIMDVHDSVNPDGMAFIPLRVI
PFLREKGVPQETLAGITVTNPARFLSPTLRAS
(pFF-PTE: replace all "F" with "X"; X: para-fluoro-phenylalanine)

SEQ ID NO: 19

DRINTVRGPITISEAGFTLTHEHICGSSAGFLRAWPEFFGSRKALAEKAVRGLRRARAAG
VRTIVDVSTFDQGRDVSLLAEVSRAADVHIVAATGLGFDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDHIPHSAIGLEDNASASAWLGI
RSWQTRALLIKALIDQGYMKQILVSNDYGFGLSAGVTNIMDVHDSVNPDGMAFIPLRVI
PFLREKGVPQETLAGITVTNPARFLSPTLRAS
(pFF-PTE: replace all "F" with "X"; X: para-fluoro-phenylalanine)

SEQ ID NO: 20

DRINTVRGPITISEAGFTLTHEHICMSSAGFLRAWPEFFGSRKALAEKAVRGLRRARAAG
VRTIVDVSTFDTGRDVSLLAEVSRAADVHIVAATGLGWDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDHIPHSAIGLEDNASASAWLGI
RSWQTRALLIKALIDQGYMKQILVSNDYSFGNSLGVTNIMDVEDSVNPDGMAFIPLRVIP
FLREKGVPQETLAGITVTNPARFLSPTLRAS
(pFF-PTE: replace all "F" with "X"; X: para-fluoro-phenylalanine)

FIGURE 24 (cont.)

SEQ ID NO: 21

DRINTVRGPITISEAGFTLTHEHICVSSAGFLRAWPEFFGSRKALAEKAVRGLRRARAAG
VRTIVDVSTFDQGRDVSLLAEVSRAADVHIVAATGLGFDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDHIPHSAIGLEDNASASAWLGI
RSWQTRALLIKALIDQGYMKQILVSNDYGFGMSAGVTNIMDVIDSVNPDGMAFIPLRVI
PFLREKGVPQETLAGITVTNPARFLSPTLRAS
(pFF-PTE: replace all "F" with "X"; X: para-fluoro-phenylalanine)

SEQ ID NO: 22

DRINTVRGPITISEAGFTLTHEHICASSAGFLRAWPEFFGSRKALAEKAVRGLRRARAAG
VRTIVDVSTFDSGRDVSLLAEVSRAADVHIVAATGLGWDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDHIPHSAIGLEDNASASAWLGI
RSWQTRALLIKALIDQGYMKQILVSNDYSFGVSIGVTNIMDVHDSVNPDGMAFIPLRVIP
FLREKGVPQETLAGITVTNPARFLSPTLRAS
(pFF-PTE: replace all "F" with "X"; X: para-fluoro-phenylalanine)

SEQ ID NO: 23

DRINTVRGPITISEAGFTLTHEHICVSSAGFLRAWPEFFGSRKALAEKAVRGLRRARAAG
VRTIVDVSTFDSGRDVSLLAEVSRAADVHIVAATGLWADPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDHIPHSAIGLEDNASASAWLGI
RSWQTRALLIKALIDQGYMKQILVSNDWAFGGSNYVTNIMDVWDSVNPDGMAFIPLRV
IPFLREKGVPQETLAGITVTNPARFLSPTLRAS
(pFF-PTE: replace all "F" with "X"; X: para-fluoro-phenylalanine)

SEQ ID NO: 24

DRINTVRGPITISEAGFTLTHEHICMSSAGFLRAWPEFFGSRKALAEKAVRGLRRARAAG
VRTIVDVSTFDQGRDVSLLAEVSRAADVHIVAATGLWDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDSTDDLSYLTALAARGYLIGLDSIPWSAIGLEDNASASAWLGI
RSWQTRALLIKALIDQGYMKQILVSNDWGFGASAGVTNIMDVYDSVNPDGMAFIPLRVI
PFLREKGVPQETLAGITVTNPARFLSPTLRAS
(pFF-PTE: replace all "F" with "X"; X: para-fluoro-phenylalanine)

FIGURE 24 (cont.)

SEQ ID NO: 25

DRINTVRGPITISEAGFTLTHEHICCSSAGFLRAWPEFFGSRKALAEKAVRGLRRARAAG
VRTIVDVSTFDQGRDVSLLAEVSRAADVHIVAATGLGNDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDCIPWSAIGLEDNASASAWLGI
RSWQTRALLIKALIDQGYMKQILVSNDYGFGASAGVTNIMDVLDSVNPDGMAFIPLRVI
PFLREKGVPQETLAGITVTNPARFLSPTLRAS
(pFF-PTE: replace all "F" with "X"; X: para-fluoro-phenylalanine)

SEQ ID NO: 26

DRINTVRGPITISEAGFTLTHEHICVSSAGFLRAWPEFFGSRKALAEKAVRGLRRARAAG
VRTIVDVSTFDAGRDVSLLAEVSRAADVHIVAATGLWADPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDHIPFSAIGLEDNASASAWLGI
RSWQTRALLIKALIDQGYMKQILVSNDWHFGGSGYVTNIMDVHDSVNPDGMAFIPLRVI
PFLREKGVPQETLAGITVTNPARFLSPTLRAS
(pFF-PTE: replace all "F" with "X"; X: para-fluoro-phenylalanine)

SEQ ID NO: 27

DRINTVRGPITISEAGFTLTHEHICGSSAGFLRAWPEFFGSRKALAEKAVRGLRRARAAG
VRTIVDVSTFDQGRDVSLLAEVSRAADVHIVAATGLGLDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDQIPFSAIGLEDNASASAWLGI
RSWQTRALLIKALIDQGYMKQILVSNDYAFGLSAGVTNIMDVHDSVNPDGMAFIPLRVI
PFLREKGVPQETLAGITVTNPARFLSPTLRAS
(pFF-PTE: replace all "F" with "X"; X: para-fluoro-phenylalanine)

SEQ ID NO: 28

DRINTVRGPITISEAGFTLTHEHICVSSAGFLRAWPEFFGSRKALAEKAVRGLRRARAAG
VRTIVDVSTFDQGRDVSLLAEVSRAADVHIVAATGLGPDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDNTDDLSYLTALAARGYLIGLDAIPHSAIGLEDNASASAWLGI
RSWQTRALLIKALIDQGYMKQILVSNDYAFGLSNGVTNIMDVHDSVNPDGMAFIPLRVI
PFLREKGVPQETLAGITVTNPARFLSPTLRAS
(pFF-PTE: replace all "F" with "X"; X: para-fluoro-phenylalanine)

FIGURE 24 (cont.)

SEQ ID NO: 29

DRINTVRGPITISEAGFTLTHEHICGSSAGFLRAWPEFFGSRKALAEKAVRGLRRARAAG
VRTIVDVSTFDGGRDVSLLAEVSRAADVHIVAATGLSWDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDSIPKSAIGLEDNASASAWLGI
RSWQTRALLIKALIDQGYMKQILVSNDYAFGLSAGVTNIMDVHDSVNPDGMAFIPLRVI
PFLREKGVPQETLAGITVTNPARFLSPTLRAS
(pFF-PTE: replace all "F" with "X"; X: para-fluoro-phenylalanine)

SEQ ID NO: 30

DRINTVRGPITISEAGFTLTHEHICASSAGFLRAWPEFFGSRKALAEKAVRGLRRARAAG
VRTIVDVSTFDQGRDVSLLAEVSRAADVHIVAATGLWDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDQIPHSAIGLEDNASASAWLGI
RSWQTRALLIKALIDQGYMKQILVSNDYPFGVSAGVTNIMDVVDSVNPDGMAFIPLRVI
PFLREKGVPQETLAGITVTNPARFLSPTLRAS
(pFF-PTE: replace all "F" with "X"; X: para-fluoro-phenylalanine)

SEQ ID NO: 31

DRINTVRGPITISEAGFTLTHEHICASSAGFLRAWPEFFGSRKALAEKAVRGLRRARAAG
VRTIVDVSTFDDGRDVSLLAEVSRAADVHIVAATGLPDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDNIPFSAIGLEDNASASAWLGI
RSWQTRALLIKALIDQGYMKQILVSNDYPFGLSAGVTNIMDVVDSVNPDGMAFIPLRVI
PFLREKGVPQETLAGITVTNPARFLSPTLRAS
(pFF-PTE: replace all "F" with "X"; X: para-fluoro-phenylalanine)

SEQ ID NO: 32

DRINTVRGPITISEAGFTLTHEHICGSSAGFLRAWPEFFGSRKALAEKAVRGLRRARAAG
VRTIVDVSTFDMGRDVSLLAEVSRAADVHIVAATGLWIDPPLSMRLRSVEELTQFFLREI
QYGIEDTGIRAGIILVATTGKATPFQELVLRAAARASLATGVPVTTHTAASQRGGEQQA
AIFESEGLSPSRVCIGHSDDTDDLSYLTALAARGYLIGLDHIPFSAIGLEDNASASAWLGI
RSWQTRALLIKALIDQGYMKQILVSNDWAFGLSAYVTNIMDVLDSVNPDGMAFIPLRVI
PFLREKGVPQETLAGITVTNPARFLSPTLRAS
(pFF-PTE: replace all "F" with "X"; X: para-fluoro-phenylalanine)

FIGURE 24 (cont.)

SEQ ID NO: 33

DRINTVRGPITISEAGFTLTHEHICFSSAGFLRAWPEFFGSRKALAEKAVRGLRRARAAG
VRTIVDVSTFDMGRDVSLLAEVSRAADVHIVAATGLGWDPPLSMRLRSVEELTQFFLRE
IQYGIEDTGIRAGIILVATTGKATPFQELVLRAAARASLATGVPVTTHTAASQRGGEQQA
AIFESEGLSPSRVCIGHSDDTDDLSYLTALAARGYLIGLDAIPHSAIGLEDNASASAWLGI
RSWQTRALLIKALIDQGYMKQILVSNDYSFGMSAGVTNIMDVHDSVNPDGMAFIPLRVI
PFLREKGVPQETLAGITVTNPARFLSPTLRAS
(pFF-PTE: replace all "F" with "X"; X: para-fluoro-phenylalanine)

PHOSPHOTRIESTERASE ENZYMES, METHODS AND COMPOSITIONS RELATED THERETO

CROSS-REFERENCE TO RELATED APPLICATION

This application claims the benefit of priority of U.S. Provisional Application Ser. No. 62/026,579, filed Jul. 18, 2014. The foregoing application is incorporated herein by reference in its entirety.

FEDERAL FUNDING

This invention was made, in part, with government support under Grant No. ARO DURIP (W911NF-12-1-029; J.K.M.). The Federal Government has certain rights in the invention.

FIELD OF THE INVENTION

The instant invention provides methods and related compositions for identifying polypeptides with improved stability and/or enzymatic activity in comparison to native forms, wherein the identified polypeptides comprise one or more non-natural amino acids. In certain embodiments, the present invention relates to novel phosphotriesterase enzymes comprising one or more non-natural amino acids. In a particular embodiment, the instant invention provides novel phosphotriesterase enzymes with greater stability and/or enhanced activity in comparison to native forms of the enzyme. The present invention also relates to compositions comprising novel phophotriesterase enzymes, such as prophylactics, decontaminants, animal feedstocks, and assay kits.

BACKGROUND OF THE INVENTION

Organophosphates are a class of compounds that comprise many commercial pesticides as well as military-grade nerve gas agents. Organophosphates inactivate acetylcholinesterase (AChE) by binding to their active site, which leads to accumulation of acetylcholine and subsequent hyper-stimulation of nerve synapses. A fraction of an ounce (1 to 10 mL) of sarin—a nerve agent—on the skin can be fatal. Methods of dissemination include air, water, food, and agricultural contamination. Both inhalation and skin exposure to sarin produce health effects within 1 to 10 minutes. Current methods of neutralization of these chemicals are resigned to the application of either detergents (with copious amounts of water) or caustic/industrial strength cleansers. It has, however, long since been demonstrated that phosphotriesterase enzymes found in nature are capable of hydrolyzing organophosphates, including pesticides and nerve gas agents. These enzymes, by and large, have yet to be optimized for stability as well as integrated into a deployment-ready solution.

SUMMARY OF THE INVENTION

In certain embodiments, the instant invention relates to an isolated mutated phosphotriesterase class enzyme, comprising at least two mutations in comparison to the non-mutated phosphotriesterase class enzyme from which it is derived, wherein at least one natural amino acid is mutated to a different natural amino acid and wherein at least a second natural amino acid is mutated to a non-canonical amino acid (NCAA).

In further embodiments, the enzyme exhibits enhanced activity at elevated temperatures and/or maintains activity over multiple days in solution at room temperature.

In some embodiments, the enzyme is effective against an organophosphate pesticide. In a particular embodiment, the pesticide is chlorpyrifos.

In certain embodiments, the NCAA is p-fluorophenylalanine (pFF). In a particular embodiment, the enzyme comprises the amino acid sequence depicted in SEQ ID NO: 3. In a further embodiment, the amino acid sequence is encoded by the nucleic acid sequence depicted in SEQ ID NO: 4.

The instant invention also relates to isolated host cells comprising the mutated phosphotriesterase enzymes described herein. In some embodiments, the host cell comprises a vector comprising the nucleic acid sequence depicted in SEQ ID NO: 4.

In yet other embodiments, the instant invention relates to a composition comprising the mutated phosphotriesterase enzymes described herein. In certain embodiments, the composition is a prophylactic. In particular embodiments, the prophylactic is a respiratory filter, inhaler, or topical cream. In some embodiments, the composition is a decontaminant. In other embodiments, the composition is a water filtration system. In yet other embodiments, the composition is a detergent. In certain embodiments, the composition is feedstock. In a particular embodiment, the mutated phosphotriesterase class enzyme is encoded by the nucleic acid sequence depicted in SEQ ID NO: 4. In further embodiments, the mutated phosphotriesterase enzyme comprises the amino acid sequence depicted in SEQ ID NO: 3.

In some embodiments, the invention relates to an assay for detecting organophosphate contamination, comprising a mutated phosphotriesterase enzyme described herein, wherein hydrolysis of one or more organophosphates by the mutated phosphotriesterase enzyme is coupled to a detectable reaction to sense the resulting change in pH. In certain embodiments, the detectable reaction is colorimetric. In other embodiments, the detectable reaction is fluorometric. In a particular embodiment, the mutated phosphotriesterase enzyme comprises the amino acid sequence depicted in SEQ ID NO: 3.

In some embodiments, the invention relates to a method of generating a polypeptide with improved stability and/or activity, comprising (a) replacing one or more amino acid residues in the polypeptide with an NCAA, (b) mutating at least one NCAA position to any amino acid except the native amino acid of the position, (c) evaluating the mutated residue in comparison to the native NCAA residue of (a) based on total energy and predicted binding energy of each chain, (d) identifying any destabilizing reductions in energy with one or more neighboring amino acids as a result of the mutated residue, (e) mutating the destabilizing residue of (d) with an alternative natural amino acid, and (f) evaluating the mutated residue of (e) for improved stability and/or activity in comparison to the polypeptide of (a), wherein any stabilizing or improved activity as a result of the mutated residue in (f) is indicative of a polypeptide with improved stability and/or activity. in certain embodiments, all residues of one type of amino acid in the polypeptide are replaced with an NCAA. In further embodiments, the type of amino acid replaced with an NCAA is phenylalanine. In yet further embodiments, the NCAA is p-fluorophenylalanine (pFF). In some embodiments, the polypeptide is a phosphotriesterase class enzyme.

BRIEF DESCRIPTION OF THE DRAWINGS

FIG. 3 is a table depicting the intensity of peaks identified from MALDI-TOF.

FIG. 4 is a table depicting protein yield of PTE, 104A, pFF-PTE, and pFF-104A.

FIG. 7 is a table depicting kinetics of paraoxon hydrolysis as a function of temperature.

FIG. 9 is a table depicting kinetics of paraoxon hydrolysis as a function of time.

FIG. 10 depicts the results of SDS-PAGE of purified proteins: a) purified PTE and 104A, b) purified pFF-PTE and pFF-104A.

FIG. 12 is a table depicting $T_m$ of protein.

FIG. 13 depicts a wildtype PTE (A) amino acid sequence and (B) DNA sequence. The "pFF-PTE" amino acid sequence is depicted in SEQ ID NO: 34.

FIG. 14 depicts the F104A-PTE (A) amino acid sequence and (B) DNA sequence. The "pFF-PTE" amino acid sequence is depicted in SEQ ID NO: 35.

FIG. 15 depicts the amino acid sequence for the mutant PTE termed "SOBA." The "pFF-SOBA" amino acid sequence is depicted in SEQ ID NO: 36.

FIG. 16 depicts the amino acid sequences for various mutant PTEs according to the instant invention. The "pFF-PTE" amino acid sequences are depicted in SEQ ID NOS: 37-44, respectively, in order of appearance.

FIG. 23A-B show two tables depicting several unique mutation sets that improve the binding score of chlorpyrifos to PTE.

FIG. 24 depicts amino acid sequences of PTE variants that may be effective in chlorpyrifos binding. The "pFF-PTE" amino acid sequences are depicted in SEQ ID NOS: 45-64, respectively, in order of appearance.

DETAILED DESCRIPTION OF THE INVENTION

Figure 1:
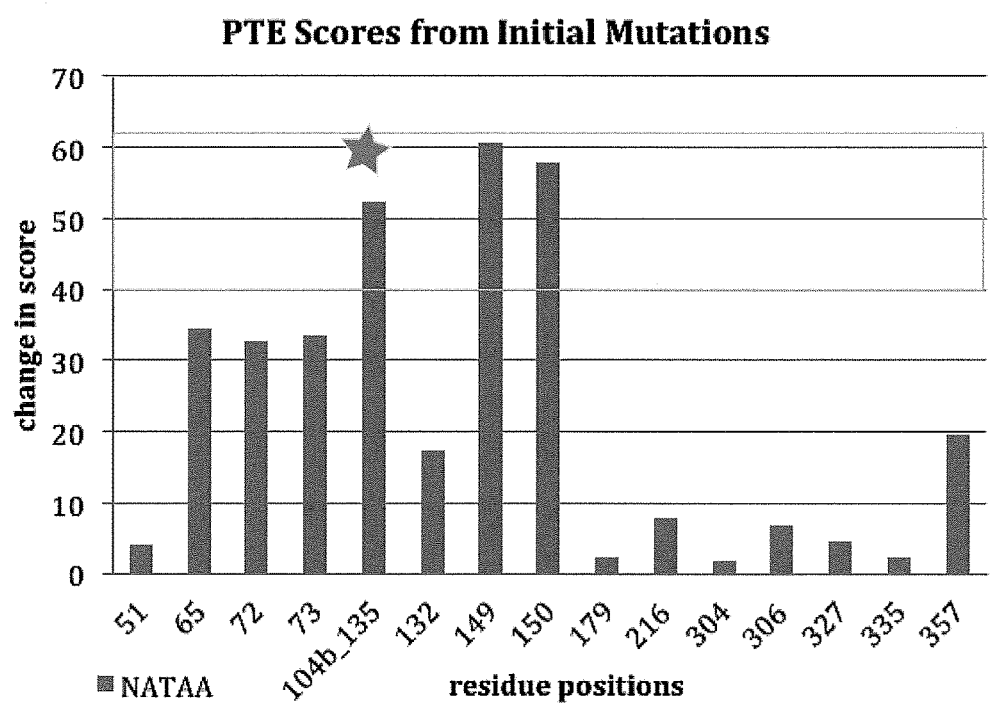
FIG. 1 depicts the energy scores of the individually mutated pFF positions within pFF-PTE with minimization as calculated by the Rosetta score 12 scoring function and relative to the energy of the wild type sequence. Star indicates pFF 104 which is known to be in the dimer interface. The other residue positions 149 and 150, also showed improved scores and are currently being explored.
Figure 2:
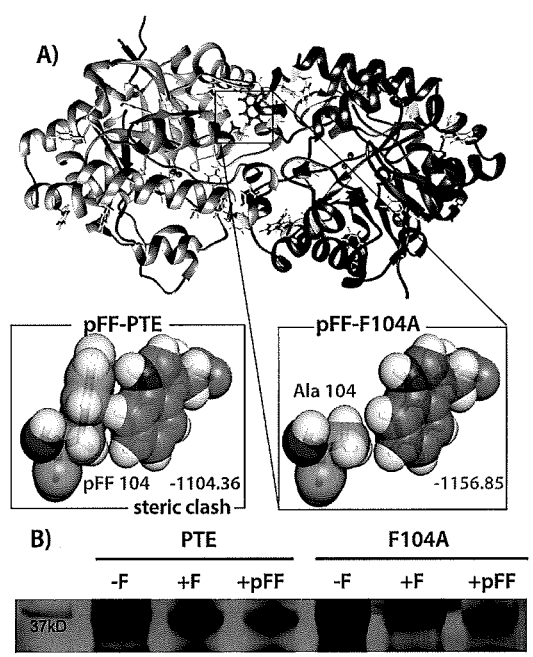
FIG. 2 depicts A) Structure of pFF-F104A identified from Rosetta in which pFFs (yellow) and F104A (red) are highlighted. Comparison of pFF-F104A and pFF-PTE with energy scores showing that pFF 104 exhibits a steric clash with neighboring residue. The original structure from 1HZY (PDB) is mutated and modified by Rosetta and rendered by UCSF Chimera. B) SDS-PAGE analysis of pFF-F104A, F104A, pFF-PTE and PTE demonstrating overexpression of all proteins. L represents ladder, F is phenylalanine and pFF is p-fluorophenylalanine.

With non-canonical amino acid (NCAA) incorporation methodologies enabling the expansion of the genetic code, methods to assist in the design of proteins bearing such analogs are urgently needed. Provided herein are computational approaches to facilitate the design of proteins containing NCAAs.

The expansion of the genetic code has led to the biosynthetic incorporation of a wide range of NCAAs into proteins [1]. In particular, fluorinated amino acids (FAAs) have been integrated into small coiled-coil proteins [2], a range of enzymes [3] and biomaterials [4]. While the incorporation of FAAs into the target protein may lead to enhanced function or stability, in some cases a loss in activity or stability occur and further improvements on the resulting artificial protein have been made through rational mutagenesis[3c] and directed evolution strategies [5]. Recently, it has been demonstrated that the residue-specific incorporation of p-fluorophenylalanine (pFF) into the S5PTE (pFF-PTE) resulted in enhanced thermoactivity [6]. While improved refolding behavior at high concentrations was observed upon fluorination, there was a significant loss in soluble protein yields, indicating that each pFF residue may not be stabilizing. Accordingly, improved pFF-PTE proteins with greater stability are desired.

While methods enabling the biosynthesis of artificial protein bearing NCAAs are known [1], tools to help further improve the overall activity and stability are needed. Although mutagenesis and evolutionary approaches have been employed successfully to identify variants with enhanced function, they rely heavily on testing or screening several to millions of constructs [3c, 5, 20]. As demonstrated herein, the use of novel methods involving computational analysis were employed to successfully isolate a fluorinated protein variant that exhibited superior stability against heat and half-life. Notably, the pFF-F104A variant is only functional in the fluorinated form, affirming the protein mutation-based design detailed herein using pFF. This provides another useful tool for artificial protein design and could be employed in conjunction with the aforementioned approaches [21].

The use of any publicly available software protein design program, such as Rosetta-design, can be employed in the design of novel proteins according to the methods of the instant invention. A discussion of the Rosetta-design software platforms can be found in, e.g., Carol A. Rohl, et al., Editor(s), Methods in Enzymology, Academic Press, 2004, Volume 383, Pages 66-93; Andrew Leaver-Fay, et al., Chapter nineteen-Rosetta3: An Object-Oriented Software Suite for the Simulation and Design of Macromolecules, In: Michael L. Johnson and Ludwig Brand, Editor(s), Methods in Enzymology, Academic Press, 2011, Volume 487, Pages 545-574; Gautam Dantas, et al., High-resolution Structural and Thermodynamic Analysis of Extreme Stabilization of Human Procarboxypeptidase by Computational Protein Design, Journal of Molecular Biology, Volume 366, Issue 4, 2 Mar. 2007, Pages 1209-1221; Drew K, et al. (2013) Adding Diverse Noncanonical Backbones to Rosetta: Enabling Peptidomimetic Design. PLoS ONE 8(7): e67051; and DiMaio F, et al. (2011) Modeling Symmetric Macromolecular Structures in Rosetta3. PLoS ONE 6(6): e20450. See also Renfrew, P D et al. (2012) Incorporation of Non-canonical Amino Acids into Rosetta and Use in Computational Protein-Peptide Interface Design. PLoS ONE 7(3): e32637. The foregoing references are hereby incorporated by reference in their entireties.

The methods of the instant invention are applicable to any number of polypeptides. More particularly, in certain embodiments, the invention provides a method of generating a polypeptide with improved stability and/or activity, comprising (a) replacing one or more amino acid residues in the polypeptide with an NCAA, (b) mutating each NCAA position to any amino acid except the native amino acid, (c) evaluating the mutated residue in comparison to the native NCAA residue of (a) based on total energy and predicted binding energy of each chain, (d) identifying any destabilizing reductions in energy with one or more neighboring amino acids as a result of the mutated residue, (e) mutating the destabilizing residue of (d) with alternative natural amino acids, and (f) evaluating the mutated residue of (e) for improved stability and/or activity in comparison to the polypeptide of (a), wherein any stabilizing or improved activity as a result of the mutated polypeptide in (f) is indicative of a polypeptide with improved stability and/or activity.

In certain embodiments, the invention pertains to a method wherein one or more of the same type of amino acid (e.g., phenylalanine) in a polypeptide is mutated to an NCAA using a computational design software program (e.g., Rosetta-design), and then one or more of the NCAAs in the polypeptide are mutated and analyzed to determine total energy and predicted binding energy between the mutated NCAA polypeptide and the parent NCAA polypeptide, wherein site-specific mutations are identified that enhance protein stability and/or activity (e.g., enzymatic activity, binding activity). In some embodiments, all amino acids of a certain type (e.g., phenylalanine) are mutated to a NCAA. In yet other embodiments, one or more of a certain type of amino acid (e.g., phenylalanine) are mutated to one type of NCAA (e.g., pFF), and one or more of a second type of amino acid are mutated to a second type of NCAA.

Any NCAA is generally suitable for use in the methods of the instant invention. A general review that provides a range of NCAAs suitable for incorporation is provided in Link, A. James, and David A. Tirrell. "Reassignment of sense codons in vivo." Methods 36.3 (2005): 291-298, and fluorinated amino acid incorporation is discussed in Merkel, L., and N. Budisa. "Organic fluorine as a polypeptide building element: in vivo expression of fluorinated peptides, proteins and proteomes." Organic & biomolecular chemistry 10.36 (2012): 7241-7261.

Examples of suitable phenylalalnine analogs, in addition to pFF, include meta-fluorophenylalanine/mFF, ortho-flourophenylalanine/oFF (see Voloshchuk, Natalya, et al. "Positional effects of monofluorinated phenylalanines on histone acetyltransferase stability and activity." Bioorganic & medicinal chemistry letters 19.18 (2009): 5449-5451.) Other suitable NCAAs include: 2-napthylalanine/2-NA (See Link, A. James, and David A. Tirrell. "Reassignment of sense codons in vivo." Methods 36.3 (2005): 291-298.); p-bromophenylalanine/pBF (See Link, A. James, and David A. Tirrell. "Reassignment of sense codons in vivo." Methods 36.3 (2005): 291-298.); p-iodophenylalanine (see Kirshenbaum, Kent, Isaac S. Carrico, and David A. Tirrell. "Biosynthesis of proteins incorporating a versatile set of phenylalanine analogues." ChemBioChem 3.2-3 (2002): 235-237.); p-cyanophenylalnine (see Kirshenbaum, Kent, Isaac S. Carrico, and David A. Tirrell. "Biosynthesis of proteins incorporating a versatile set of phenylalanine analogues." ChemBioChem 3.2-3 (2002): 235-237.); p-ethynylphenylalanine (See Kirshenbaum, Kent, Isaac S. Carrico, and David A. Tirrell. "Biosynthesis of proteins incorporating a versatile set of phenylalanine analogues." ChemBioChem 3.2-3 (2002): 235-237.); acetylphenylalanine (See Link, A. James, and David A. Tirrell. "Reassignment of sense codons in vivo." Methods 36.3 (2005): 291-298.); benzofuranylalanine/BFA (See Link, A. James, and David A. Tirrell. "Reassignment of sense codons in vivo." Methods 36.3 (2005): 291-298.); azidophenylalanine (See Kirshenbaum, Kent, Isaac S. Carrico, and David A. Tirrell. "Biosynthesis of proteins incorporating a versatile set of phenylalanine analogues." ChemBioChem 3.2-3 (2002): 235-237.); 2-, 3-, and 4-pyridylalanine (see Kirshenbaum, Kent, Isaac S. Carrico, and David A. Tirrell. "Biosynthesis of proteins incorporating a versatile set of phenylalanine analogues." ChemBioChem 3.2-3 (2002): 235-237.)

Met analogs: propargylalanine/Pra (see Truong, Frank, et al. "Two-strain, cell-selective protein labeling in mixed bacterial cultures." Journal of the American Chemical Society 134.20 (2012): 8551-8556.); homoproargylglycine/Hpg (see Beatty, Kimberly E., et al. "Selective dye-labeling of newly synthesized proteins in bacterial cells." Journal of the American Chemical Society 127.41 (2005): 14150-14151, Beatty, Kimberly E., and David A. Tirrell. "Two-color labeling of temporally defined protein populations in mammalian cells." Bioorganic & medicinal chemistry letters 18.22 (2008): 5995-5999.); homoallylglycine/Hag (See Link, A. James, and David A. Tirrell. "Reassignment of sense codons in vivo." Methods 36.3 (2005): 291-298.); transcrotylglycine/Tcg (See Link, A. James, and David A. Tirrell. "Reassignment of sense codons in vivo." Methods 36.3 (2005): 291-298.); azidohomoalanine/Aha (See Link, A. James, and David A. Tirrell. "Cell Surface Labeling of *Escherichia coli* via Copper (I)-Catalyzed [3+2] Cycloaddition." Journal of the American Chemical Society 125.37 (2003): 11164-11165; Kiick, Kristi L., et al. "Incorporation of azides into recombinant proteins for chemoselective modification by the Staudinger ligation." Proceedings of the National Academy of Sciences 99.1 (2002): 19-24.); difluoromethionine/Dfm (see Vaughan, Mark D., et al. "Difluoromethionine as a novel 19F NMR structural probe for internal amino acid packing in proteins." Journal of the American Chemical Society 121.37 (1999): 8475-8478.); trifluormethionine/Tfm (see Vaughan, Mark D., Peter B. Sampson, and John F. Honek. "Methionine in and out of proteins: targets for drug design." Current medicinal chemistry 9.3 (2002): 385-409.); telluromethionine/Tm (see Vaughan, Mark D., Peter B. Sampson, and John F. Honek. "Methionine in and out of proteins: targets for drug design." Current medicinal chemistry 9.3 (2002): 385-409.); trifluoronorleucine/Tfn (see Merkel, L., and N. Budisa. "Organic fluorine as a polypeptide building element: in vivo expression of fluorinated peptides, proteins and proteomes." Organic & biomolecular chemistry 10.36 (2012): 7241-7261.)

Leu analogs: trifluoroleucine/TFL and SS, SR isomers (see Montclare, Jin Kim, and David A. Tirrell. "Evolving proteins of novel composition." Angewandte Chemie 118.27 (2006): 4630-4633, Montclare, Jin Kim, et al. "Biosynthesis and Stability of Coiled-Coil Peptides Containing (2S,4R)-5, 5, 5-Trifluoroleucine and (2S,4S)-5, 5, 5-Trifluoroleucine." ChemBioChem 10.1 (2009): 84-86; Panchenko, Tatyana, Wan Wen Zhu, and Jin Kim Montclare. "Influence of global fluorination on chloramphenicol acetyltransferase activity and stability." Biotechnology and bioengineering 94.5 (2006): 921-930, Voloshchuk, Natalya, et al. "Fluorinated chloramphenicol acetyltransferase thermostability and activity profile: Improved thermostability by a single-isoleucine mutant." Bioorganic & medicinal chemistry letters 17.21 (2007): 5907-5911.); hexafluoroleucine/HFL (See Tang, Yi, and David A. Tirrell. "Biosynthesis of a highly stable coiled-coil protein containing hexafluoroleucine in an engineered bacterial host." Journal of the American Chemical Society 123.44 (2001): 11089-11090.)

Ile analogs: trifluoroisoleucine/TFI (See Son, Soojin, I. Caglar Tanrikulu, and David A. Tirrell. "Stabilization of bzip peptides through incorporation of fluorinated aliphatic residues." ChemBioChem 7.8 (2006): 1251-1257.).

Val analogs: trifluorovaline/TFV (See Son, Soojin, I. Caglar Tanrikulu, and David A. Tirrell. "Stabilization of bzip peptides through incorporation of fluorinated aliphatic residues." ChemBioChem 7.8 (2006): 1251-1257.)

Pro analogs: 2S-pipecolic acid ((See Link, A. James, and David A. Tirrell. "Reassignment of sense codons in vivo." Methods 36.3 (2005): 291-298.) (3R-F)Pro, (3S-F)Pro, (4R-F)Pro, (4S-F)Pro, (4-F2)Pro (see Merkel, L., and N. Budisa. "Organic fluorine as a polypeptide building element: in vivo expression of fluorinated peptides, proteins and proteomes." Organic & biomolecular chemistry 10.36 (2012): 7241-7261.)

His analogs: (2-F)His, (4-S)His (see Merkel, L., and N. Budisa. "Organic fluorine as a polypeptide building element: in vivo expression of fluorinated peptides, proteins and proteomes." Organic & biomolecular chemistry 10.36 (2012): 7241-7261.)

Tyr analogs: (2-F)Tyr, (3-F)Tyr (see Merkel, L., and N. Budisa. "Organic fluorine as a polypeptide building element: in vivo expression of fluorinated peptides, proteins and proteomes." Organic & biomolecular chemistry 10.36 (2012): 7241-7261.).

Trp analogs: (4-F)Trp, (5-F)Trp, (6-F)Trp, (7-F)Trp (See Merkel, L., and N. Budisa. "Organic fluorine as a polypeptide building element: in vivo expression of fluorinated peptides, proteins and proteomes." Organic & biomolecular chemistry 10.36 (2012): 7241-7261.)

Any vector and host cell suitable for expressing proteins incorporating NCAAs may be used in the methods of the instant invention. For example, host cells that are phenylalanine auxotrophs will be suitable for expressing polypeptides comprising p-fluorophenylalanine (pFF). This similarly applies to o- and m-isomers of pFF. In addition, expression of a gene of interest is typically controlled under a strict inducible promoter system. However, wild-type sequences in the absence of non-canonical amino acids for incorporation may be expressed in any number of hosts and vectors, including *Saccharomyces cerevisiae*.

It is understood to one of ordinary skill in the art that conditions for culturing a host cell varies according to the particular gene and that routine experimentation is necessary at times to determine the optimal conditions for culturing the vector depending on the host cell. A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; M. J. Gait (Editor), 1984, Oligonucleotide Synthesis: A Practical Approach, Irl Press; and, D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

The term "nucleic acid" encompasses DNA, RNA (e.g., mRNA, tRNA), heteroduplexes, and synthetic molecules capable of encoding a polypeptide and includes all analogs and backbone substitutes such as PNA that one of ordinary skill in the art would recognize as capable of substituting for naturally occurring nucleotides and backbones thereof. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences, which encode a particular amino acid sequence.

Unless otherwise indicated, nucleic acids are written left to right in 5' to 3' orientation; amino acid sequences are written left to right in amino to carboxy orientation, respectively.

As used herein, the term "amino acid sequence" is synonymous with the terms "polypeptide," "protein," and "peptide," and are used interchangeably. Where such amino acid sequences exhibit activity, they may be referred to as an "enzyme." The conventional one-letter or three-letter code for amino acid residues are used herein.

As used herein, a "synthetic" molecule is produced by in vitro chemical or enzymatic synthesis rather than by an organism.

As used herein, the term "expression" refers to the process by which a polypeptide is produced based on the nucleic acid sequence of a gene. The process includes both transcription and translation.

A "gene" refers to the DNA segment encoding a polypeptide or RNA.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% free of these materials.

"Native" proteins or polypeptides refer to proteins or polypeptides isolated from the source in which the proteins naturally occur. "Recombinant" polypeptides refer to polypeptides produced by recombinant DNA techniques, e.g., produced from cells transformed by an exogenous DNA construct encoding the desired polypeptide. "Synthetic" polypeptides include those prepared by chemical synthesis.

By "homolog" is meant an entity having a certain degree of identity with the subject amino acid sequences and the subject nucleotide sequences. As used herein, the term "homolog" covers identity with respect to structure and/or function, for example, the expression product of the resultant nucleotide sequence has the enzymatic activity of a subject amino acid sequence. With respect to sequence identity, preferably there is at least 70%, 75%, 80%, 81%, 82%, 83%, 84%, 85%, 86%, 87%, 88%, 89%, 90%, 91%, 92%, 93%, 94%, 95%, 96%, 97%, 98%, or even 99% sequence identity. The term, homolog, may apply to the relationship between genes separated by the event of speciation or to the relationship between genes separated by the event of genetic duplication.

Relative sequence identity can be determined by commercially available computer programs that can calculate % identity between two or more sequences using any suitable algorithm for determining identity, using, for example, default parameters. A typical example of such a computer program is CLUSTAL. Advantageously, the BLAST algorithm is employed, with parameters set to default values. The BLAST algorithm is described in detail on the National Center for Biotechnology Information (NCBI) website.

The homologs of the peptides as provided herein typically have structural similarity with such peptides. A homolog of a polypeptide includes one or more conservative amino acid substitutions, which may be selected from the same or different members of the class to which the amino acid belongs.

As used herein, "fragment" or "portion" as applied to a gene or a polypeptide, will ordinarily be at least 10 residues, more typically at least 20 residues, and preferably at least 30 (e.g., 50) residues in length, but less than the entire, intact sequence. Fragments of these genes can be generated by methods known to those skilled in the art, e.g., by restriction digestion of naturally occurring or recombinant genes, by recombinant DNA techniques using a vector that encodes a defined fragment of the gene, or by chemical synthesis.

Any polypeptide (for which improved stability and/or activity is desired) may be employed in the methods of the invention to generate a modified polypeptide having enhanced stability and/or activity. Examples of polypeptides suitable for use in the methods of the instant invention include enzymes, receptors, protein ligands, peptide hormones, carrier proteins, structural proteins, and cell adhesion proteins.

In certain embodiments, the methods of the instant invention provide for the development and production of modified phosphotriesterase (PTE) polypeptides. In an advantageous embodiment, the modified PTE polypeptide has improved stability and/or enzymatic activity over the wildtype PTE polypeptide from which the modified PTE is derived. PTE polypeptides encompass a class of proteins capable of hydrolyzing organophosphates.

Identified from *Pseudomonas diminuta*, PTE hydrolyzes a broad range of substrates including organophosphates and esters [22-37]. As a member of the amidohydrolase superfamily, it adopts a TIM barrel motif where a binuclear zinc center exists at the C-terminus of each monomer [38-41]. The insecticide, paraoxon, has been used as the standard for determining organophosphate degradation. Though the use of paraoxon as an insecticide is limited, its degradation by PTE has been well documented; in comparison to the commonly used insecticide, chlorpyrifos, PTE hydrolyzes paraoxon ~1,200 fold more efficiently [42-44]. The catalytic efficiency and the rate limiting step are dependent on the pKa of the leaving group [42]. Although numerous studies have been completed to understand the PTE mechanism of action and improve activity [27], the protein's soluble expression levels, stability, and activity under non-natural conditions including high temperatures have remained largely unexplored.

As defined herein, a member of the PTE family of enzymes comprises a sequence that has a blastp alignment to each of SEQ ID NOS: 1-5 with an e-value lower than 1e-6. PTE members as defined herein should also typically either have (1) EC id 3.1.8.1 (Enzyme Nomenclature, Supplement 19, International Union of Biochemistry and Molecular Biology, 2013) and/or (2) the ability to catalyze the cleavage of organic phosphodiesters such as V-series nerve agents, chlorpyrifos, and paraoxon as demonstrated by an enzymatic assay. In certain embodiments, Blastp version 2.2.29 (or equivalent) should be used with default parameters to compute the e-value.

In certain embodiments, the modified PTE polypeptides of the invention are derived from the wildtype PTE protein having the amino acid sequence depicted in SEQ ID NO: 1, which is encoded by the nucleic acid sequence depicted in SEQ ID NO: 2. See, e.g., Benning, M M, et al. Biochemistry (2001) 40:2712-2722.

As described herein, the Rosetta-design software was employed in one embodiment of the instant invention to develop a fluorinated phosphotriesterase variant of SEQ ID NO: 1, pFF-104A, that was isolated and characterized and that demonstrated enhanced thermostability and half-life. Incorporating p-fluorophenylalanine (pFF) into phosphotriesterase (PTE) dramatically improved folding, leading to enhanced stability and function at elevated temperatures. The pFF-104A protein that was discovered exhibited enhanced activity at elevated temperatures and also maintained activity over multiple days in solution at room temperature. The amino acid sequence of the pFF-104A protein is depicted in SEQ ID NO: 3, and the nucleic acid sequence encoding the pFF-104A protein is depicted in SEQ ID NO: 4.

As detailed herein, Rosetta was used to identify multiple potential stabilizing mutations. In a particular embodiment, the instant invention relates to the modified PTE protein having the amino acid sequence depicted in SEQ ID NO: 5. In yet other embodiments, the instant invention relates to the modified PTE protein having the amino acid sequence depicted in any one of SEQ ID NOS: 6-13.

In certain embodiments, the invention relates to modified PTE enzymes that exhibit enhanced activity at elevated temperatures and/or maintain activity over multiple days in solution at room temperature or at 37° C. In further embodiments, the instant invention relates to a recombinantly generated enzyme that neutralizes the toxic effects of pesticides and warfare-grade nerve agents. For example, in a particular embodiment, the invention provides a recombinantly generated enzyme that is a computationally-optimized structural variant of a naturally occurring phosphotriesterase class enzyme found in Pseudomonas diminuta. In further embodiments, the engineered protein is catalytic in nature, and neutralizes a lot with very little starting material, in very little time. In a particular embodiment, it facilitates this neutralization reaction within minutes.

In certain embodiments, the instant invention relates to a highly engineered protein that is endowed with increased enzymatic stability for the degradation of organophosphates present in pesticides and nerve gases. In further embodiments, the protein is capable of neutralizing bulk amounts of chemical warfare stocks, such as those composed of sarin gas.

Examples of pesticides that one or more PTE variants of the instant invention may demonstrate efficacy against (e.g., demonstrate an ability to degrade organophosphates present in the pesticide) include organophosphate pesticides such as acephate (O,S-dimethyl acetyl-phosphoramidothioate) and its cholinesterase-inhibiting metabolite O,S-dimethyl phosphoramidothioate; 4-tert-butyl-2-chlorophenyl methyl methyl phosphoramidate; S-[(tert-Butylthio)methyl]O,O-diethyl phosphorodithioate and its cholinesterase-inhibiting metabolites; carbophenothion (S-[(p-chlorophenyl)thiolmethyl]O,O-diethyl phosphorodithioate) and its cholinesterase-inhibiting metabolites; chlorpyrifos (O,O-diethyl O-(3,5,6-trichloro-2-pyridyl)phosphorothioate); chlorpyrifos-methyl (O,O-dimethyl-O-(3,5,6-trichloro-2-pyridyl) phosphorothioate; 2-Chloro-1-(2,4,5-trichlorophenyl)vinyl dimethyl phosphate; 2-Chloro-1-(2,4-dichlorophenyl) vinyl diethyl phosphate; coumaphos (O,O-diethyl O-3-chloro-4-methyl-2-oxo-2H-1-benzopyran-7-yl phosran-7-yl phosphate); coumaphos oxygen analog (O,O-diethyl O-3-chloro-4-methyl-2-oxo-2H-1-benzopyphorothioate); dialifor (S-(2-chloro-1-phthalimidoethyl) O,O-diethyl phosphorodithioate); dialifor oxygen analog (S-(2-chloro-1-phthalimidoethyl) O,O-diethyl phosphorothioate); demeton (a mixture of O,O-diethyl O-(and S) [2-ethylthio)ethyl] phosphorothioates); 2,2-Dichlorovinyl dimethyl phosphate; O,O-diethyl S[2-(ethylthio)ethyl]phosphorodithioate and its cholinesterase-inhibiting metabolites; O,O-diethyl O-(2-diethylamino-6-methyl-4-pyrimidinyl)phosphorothioate and its oxygen analog diethyl 2-diethylamino-6-methyl-4-pyrimidinyl phosphate; O,O-diethyl O-(2-isoprophyl-4-methyl-6-pyrimidinyl)phosphorothioate; O,O-diethyl O-[p-(methylsulfinyl)phenyl]phosphorothioate and its cholinesterase-inhibiting metabolites; diethyl 2-pyrazinyl phosphate; O,O-diethyl O-2-pyrazinyl phosphorothioate; S—(O,O-diisopropyl phosphorodithioate) of N-(2-mercaptoethyl)benzenesulfonamide; dimethoate (O,O-dimethyl S—(N-methyl-carbamoylmethyl)phosphorodithioate); dimethoate oxygen analog (O,O-dimethyl S—(N-methyl-carbamoylmethyl) phosphorothioate); O,O-dimethyl O-p-(dimethylsulfamoyl)phenyl phosphate; O,O-dimethyl O-p-(dimethylsulfamoyl)phenyl phosphorothioate; O,O-dimethyl S-[4-oxo-1,2,3-benzotriazin-3-(4H)-ylmethyl] phosphorodithioate; dimethyl phosphate of 3-hydroxy-N,N-dimethyl-cis-crotonamide; dimethyl phosphate of 3-hydroxy-N-methyl-cis-crotonamide; dimethyl phosphate of α-methylbenzyl 3-hydroxy-cis-crotonate; O,O-dimethyl 2,2,2-trichloro-1-hydroxyethyl phosphonate; O,O-dimethyl phosphorodithioate, S-ester with 4-(mercaptomethyl)-2-methozy-Δ2-1,3,4-thiadiazolin-5-one; dioxathion (2,3-p-dioxanedithiol S,S-bis (O,O-diethylphosphorodithioate)) containing approximately 70 percent cis and trans isomers and approximately 30 percent related compounds; EPN; ethion; ethion oxygen analog (5-[[(diethoxyphosphinothioyl)thio] methyl]O,O-diethyl phosphorothioate); O-ethyl O-[4-(methylthio)phenyl]S-propyl phosphorodithioate and its cholinesterase-inhibiting metabolites; O-Ethyl S,S-dipropylphosphorodithioate; ethyl 3-methyl-4-(methylthio)phenyl (1-methylethyl)phosphoramidate and its cholinesterase-inhibiting metabolites; O-ethyl S-phenyl ethylphosphonodithioate; O-ethyl S-phenyl ethylphosphonothiolate; S[2-ethylsulfinyl)ethyl]O,O-dimethyl phosphorothioate and its cholinesterase-inhibiting metabolites, (primarily S-[2-(ethyl-sulfonyl)ethyl]O,O-dimethyl phosphorothioate); fenthion (O,O-dimethyl O-[3-methyl-4-(methylthio)phenyl] phosphorothioate and its cholinesterase-inhibiting metabolites; malathion; N-(mercaptomethyl)phthalimide S—(O,O-dimethyl phosphorodithioate); N-(mercaptomethyl)phthalimide S—(O,O-dimethyl phosphorothioate); 1-methoxycarbonyl-1-propen-2-yl dimethyl phosphate and its beta isomer; methyl parathion; naled (1,2-dibromo-2,2-dichloroethyl dimethyl phosphate); parathion; phorate (O,O-diethyl S-(ethylthio)methyl phosphorodithioate) and its cholinesterase-inhibiting metabolites; phosalone (S-(6-chloro-3-mercaptomethyl)-2-benzoxazolinone) O,O-diethyl phosphorodithioate); phosphamidon (2-chloro-2-diethylcarbamoyl-1-methylvinyl dimethyl phosphate) including all of its related cholinesterase-inhibiting compounds; pirimiphos-methyl O-[2-diethylamino-6-methyl-pyrimidinyl) O,O-dimethyl phosphorothioate; ronnel; schradan (octamethylpyrophosphoramide); tetraethyl pyrophosphate; O,O,O',O'-tetramethyl O,O'-sulfinyldi-p-phenylene phosphorothioate; O,O,O',O'-tetramethyl O,O'-thiodi-p-phenylene phosphorothioate; tributyl phosphorotritlioite; and S,S,S-Tributyl phosphorothrithioate.

Examples of other pesticides against which one or more PTE variants may be effective (e.g., degradation) include aldicarb (2-methyl-2-(methylthio) propionaldehyde O-(methylcarbamoyl)oxime) and its chlorinesterase-inhibiting metabolites 2-methyl-2-(methylsulfinyl)propionaldehyde O-(methycarbamoyl) oxime and 2-methyl-2-(methylsulfonyl)propionaldehyde O-(methylcarbamoyl)oxime; carbaryl (1-naphthyl N-methylcarbamate); carbofuran (2,3-dihydro-2,2-dimethyl-7-benzofuranyl-N-methylcarbamate); carbofuran metabolite (2,3-dihydro-2,2-dimethyl-3-hydroxy-7-benofuranyl N-methylcarbamate); ethiolate (S-ethyl diethylthiocarbamate); 2-(dimethylamino)-5,6-dimethyl-4-pyrimidinyl dimethylcarbamate and its metabolites 5,6-dimethyl-2-(formylmethylamino)-4-pyrimidinyl dimethylcarbamate and 5,6-dimethyl-2-(methylamino)-4-pyrimidinyl dimethylcarbamate (both calculated as parent); ethephon ((2-chloroethyl)phosphonic acid); m-(1-ethylpropyl)phenyl methylcarbamate; methomyl (S-methyl N-[(methylcarbamoyl)oxy]thioacetimidate); m-(1-Methylbutyl)phenyl methylcarbamate; oxamyl (methyl N'N-dimethyl-N-[(methylcarbamoyl)oxy]-1-thiooxamimidate); and 3,4,5-Trimethylphenyl methylcarbamate and its isomer 2,3,5-trimethylphenyl methylcarbamate.

In yet other embodiments, for example, within the context of military applications, the subject technology provides an alternative to current chemical methods for the decontamination of persistent nerve agents. In certain embodiments, the inventive proteins integrate into a prophylactic device, such as a respiratory filter, inhaler, or topical cream, to dramatically reduce direct exposure to organophosphate class compounds by degrading them prior to transfer into, for example, human systems.

For example, the inventive proteins can be incorporated into prophylactic topical creams for application on the skin. The compositions will typically comprise an effective amount of one or more inventive polypeptides of the instant application. Furthermore, the compositions can comprise a pharmaceutically acceptable vehicle. Appropriate vehicles include those that remain in the place of application on the skin, forming a continuous film resistant to water immersion and perspiration. The vehicle can be organic and capable of containing a formulation comprising a polypeptide of the invention in a diluted or dispersed form. Lotions, creams, solutions, gels, and solids are the usual physical forms of the composition.

Topical application means depositing or spreading the inventive compound (e.g., a mutant PTE according to the invention) and the compositions over the epidermic tissue (including skin and oral, gingival, nasal, etc. tissues).

In certain embodiments, an inventive polypeptide as described herein is formulated into a lotion comprising an emollient (e.g., from 1% to 25%) and the appropriate amount of water. Examples of emollients are: I. Hydrocarbon waxes and oils such as mineral oils, petrolatum, paraffin, ceresin, microcrystalline wax, polyethylene and perhydrosqualene. II. Silicone oils such as dimethylpolysiloxanes, methylphenylpolysiloxanes and water-soluble and alcohol-soluble glycol-silicone copolymers. III. Triglycerides, such as animal and vegetable fats and oils. Examples include, but are not limited to, castor oil, cod liver oil, corn oil, olive oil, almond oil, palm oil, sesame oil, cotton seed oil and soybean oil. IV. Acetoglyceride esters, such as acetylated monoglycerides. V. Ethoxylated glycerides, such as ethoxylated glycerol monostearate. VI. Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristoyl lactate and cetyl lactate. VII. Alkenyl esters of fatty acids having 10 to 20 carbon atoms. Examples thereof include, but are not limited to, oleyl myristate, oleyl stearate and oleyl oleate. VIII. Fatty acids having 10 to 20 carbon atoms. Suitable examples include, but are not limited to, pelargonic, lauric, myristic, palmitic, stearic, isostearic, hydroxystearic, oleic, linoleic, ricinoleic, arachidonic, behenic and erucic acids. IX. Fatty alcohols having 10 to 20 carbon atoms. Lauryl, myristoyl, palmitoyl, stearyl, isostearyl, hydroxystearyl, oleyl, ricinoleyl, behenyl, erucyl and 2-octyl dodecanol alcohols are appropriate examples of fatty alcohols. X. Fatty alcohol ethers. Ethoxylated fatty alcohols having 10 to 20 carbon atoms include, but are not limited to, lauryl, cetyl, stearyl, isostearyl, oleyl and cholesterol alcohols having attached thereto from 1 to 50 ethylene oxide groups or 1 to 50 propylene oxide groups. XI. Ether-esters, such as fatty acid esters of ethoxylated fatty alcohols. XII. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleates, lanolin alcohols ricinoleate, acetate of lanolin alcohols ricinoleate, hydrogenolysis of lanolin, and liquid or semisolid lanolin absorption bases are illustrative examples of lanolin derived emollients. XIII. Polyhydric alcohols and polyether derivatives. Propylene glycol, dipropylene glycol, polypropylene glycol 2000 and 4000, polyoxyethylene polypropylene glycols, glycerol, ethoxylated glycerol, propoxylated glycerol, sorbitol, ethoxylated sorbitol, hydroxypropyl sorbitol, polyethylene glycol 200-6000, methoxy polyethylene glycols 350, 550, 750, 2000, 5000, poly(ethylene oxide) homopolymers (100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), and polyoxypropylene derivatives of trimethylolpropane are suitable examples. XIV. Polyhydric alcohol esters. Mono- and di-acyl esters of ethylene glycol, mono- and di-acyl esters of diethylene glycol, mono- and di-acyl esters of polyethylene glycol (200-6000), mono- and di-acyl esters of propylene glycol, polypropylene glycol 2000 monooleate, polypropylene glycol 2000 monostearate, ethoxylated propylene glycol monostearate, mono- and di-acyl esters of glycerol, polyacyl esters of poly glycerol, ethoxylated glycerol monostearate, 1,3-butylene glycol monostearate, 1,3-butylene glycol distearate, acyl ester of polyoxyethylene polyol, acyl esters of sorbitan, and acyl esters of polyoxyethylene sorbitan are suitable examples. XV. Waxes such as beeswax, spermaceti, myristoyl myristate and stearyl stearate. XVI. Beeswax derivatives, such as polyoxyethylene sorbitol beeswax. These are reaction products of beeswax with ethoxylated sorbitol of varying ethylene oxide content that form a mixture of ether-esters. XVII. Vegetable waxes, including, but not limited to, carnauba and candelilla waxes. XVIII. Phospholipids such as lecithin and derivatives. XIX. Sterols. Examples include, but are not limited to, cholesterol and acyl esters of cholesterol. XX. Amides, such as fatty acid amides, ethoxylated acyl amides and solid fatty acid alkanolamides.

In some embodiments, lotions of the invention further contain an emulsifier, e.g., from 1% to 30% of an emulsifier. The emulsifiers can be anionic, cationic, or non-ionic. Examples of non-ionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbons in the alkyl chain condensed with 2 to 20 moles of ethylene oxide, mono- and di-acyl esters of ethylene glycol, wherein the fatty acid contains from 10 to 20 carbons, monoglycerides wherein the fatty acid contains from 10 to 20 carbons, diethylene glycol, polyethylene glycols of molecular weight 200 to 6000, polypropylene glycol of molecular weight 200 to 3000, glycerol, sorbitol, sorbitan, polyoxyethylene sorbitol, polyoxyethylene sorbitan and hydrophilic wax esters. Anionic emulsifiers include, but are not limited to, fatty acids saponified (soaps) with potassium, sodium, or triethanolamine, wherein the fatty acid contains from 10 to 20 carbons. Other anionic emulsifiers include, but are not limited to, alkali metals, ammonium or substituted ammonium with alkyl sulfates, alkyl arylsulfonates and alkyl ethoxy ether sulfonates having 10 to 30 carbons in the alkyl chain and from 1 to 50 ethylene oxide units. Cationic emulsifiers include quaternary ammonium and morpholinium and pyridinium compounds.

Some emollients previously described also have emulsifying properties. When a lotion contains one of these emollients, an additional emulsifier is not needed, though it can be included in the formulation.

Typically, the balance of the composition is water. The lotions can be formulated by simply admixing all of the components together. Optional components such as an emulsifier or common additives may be included in the composition. A common additive is a thickening agent. In certain embodiments, a thickening agent is included at a level of, e.g., 1% to 30% by weight of the composition. Examples of thickening agents are: cross-linked carboxypolymethylene polymers, methyl cellulose, polyethylene glycols, gums and bentonite.

The compositions of the present invention may also be formulated in the form of a cream. In addition to a polypeptide of the invention, creams can contain an emollient (e.g., from 5% to 50%) and the remainder is water. The emollients, as described above, can also be used in the cream formulation. Optionally, the cream may contain an emulsifier, e.g., at a level from 3% to 50%. The previously described emulsifiers would also be suitable.

Current technologies employed to protect military and civilian personnel from an unexpected exposure to nerve agents consist of standard personal protective equipment (general issue clothing and gas masks). These do not reduce the persistence of the agents themselves, but rather provide limited physical barriers to deeper exposure. Decontamination requires treatment of contacted surfaces with caustic chemicals or detergents combined with copious amounts of water. In the case of the 1995 Tokyo subway attack, involving the release of sarin gas, hazardous material crews decontaminated the sites by spraying all contaminated surfaces with industrial-strength cleaners. This current method of addressing the persistence problem associated with organophosphates relies on a large uncontaminated water supply as well as the chemicals themselves. In certain embodiments, the technology described herein overcomes these requirements by virtue of stable catalytic action of the inventive polypeptides.

Figure 5:
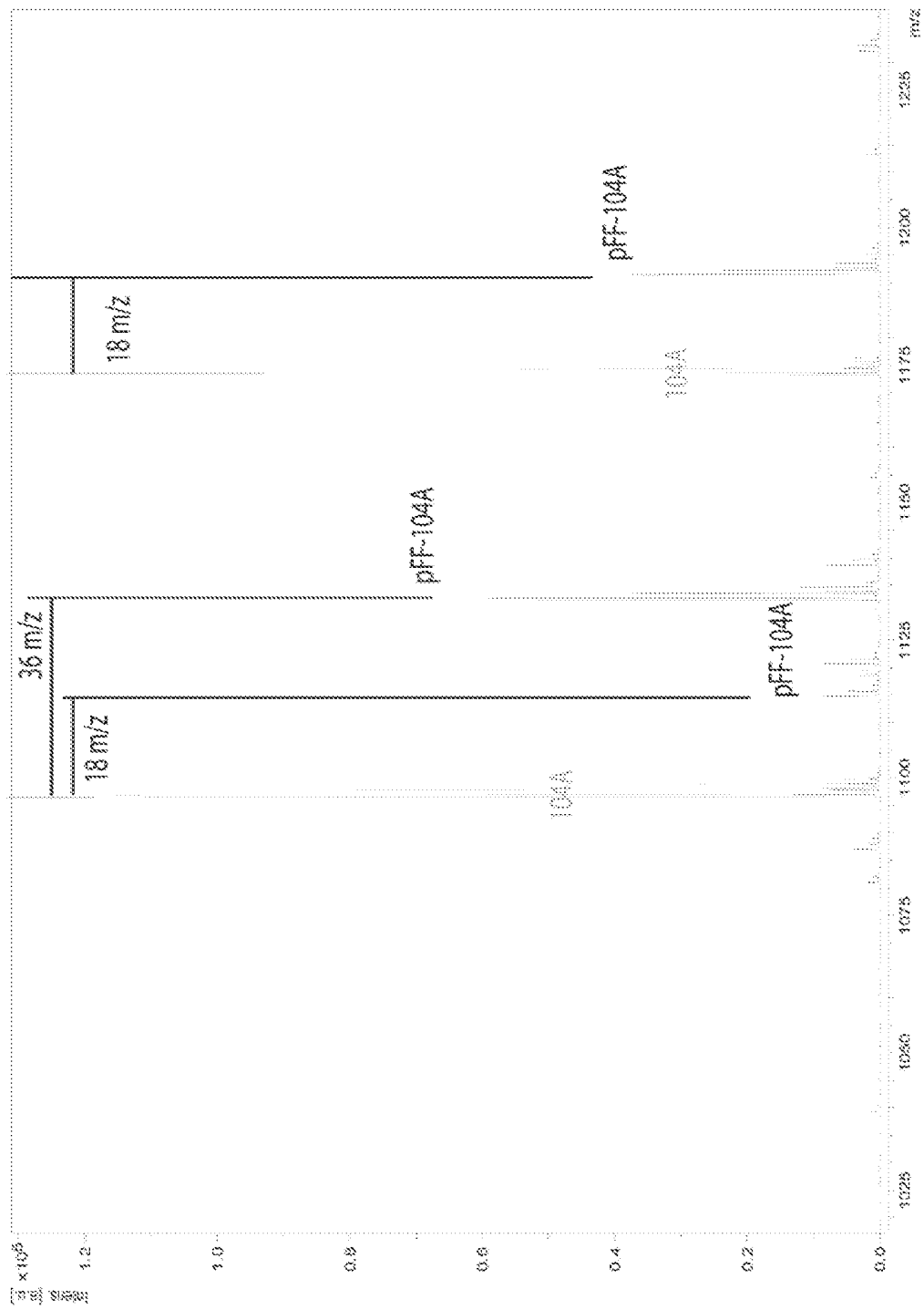
FIG. 5 depicts MALDI-TOF mass spectra of tryptic peptide fragments.
Figure 6:
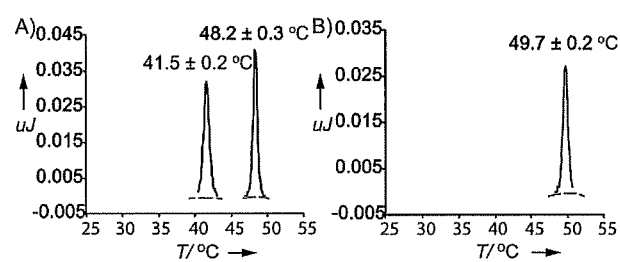
FIG. 6 depicts differential scanning calorimetry thermograms of A) pFF-PTE and B) pFF-F104A.

In other embodiments, within the context of agribusiness, for example, the instant technology may be used to decontaminate food stocks contaminated with organophosphate-based pesticides. In yet other embodiments, the gene itself for a functional phenylalanine mutant according to the instant invention may be directly integrated into the genome of genetically modified organism (GMO) feedstocks for controlled degradation of pesticides upon ripening.

In some embodiments, the invention relates to products for use in the laundry product market. For example, in certain embodiments, the invention provides enzymes capable of degrading organophophate-based pesticides and that are suitable for integration into, e.g., water filtration systems or consumer-grade/industrial-grade laundry detergents. In further embodiments, the invention relates to a laundry detergent product that fully degrades pesticides that may contaminate clothing.

In yet other embodiments, the invention relates to a water filter capable of carrying out the enzymatic reaction of an enzyme of the invention in a flow-through format. In particular embodiments, the invention provides a decontamination filter for organophosphate-ridden runoff. For example, in some embodiments, water polluted with organophosphates is placed in contact with a filter with immobilized PTE (e.g., mutant PTE according to the instant invention) whereby any organophosphates in the water are hydrolyzed by the immobilized PTE with which the water comes in contact.

In other embodiments, the invention relates to an assay in which the enzyme-driven hydrolysis of organophosphates is coupled with a colorimetric reaction to sense the accompanying change in pH, thus yielding a colorimetric sensor of organophosphate contamination. In certain embodiments, the assay is a colony assay. In other embodiments, the assay is conducted on cell lysates e.g., in a 96-well format. In some embodiments, the assay involves a pH probe wherein the enzyme is tethered to the probe.

The invention will now be further described by way of the following non-limiting examples.

EXAMPLES

Example 1

Rosetta [7] is a suite of libraries and tools for macromolecular modelling that has been employed to perform small molecule ligand docking [8], thermo-stabilize proteins [9], design hydrogen bond networks [10], design novel protein folds [11], create novel protein interfaces, and design enzymes [12] including those that contain NCAAs in their active sites [13]. The inventors have extended Rosetta to enable the use of more than 200 NCAA side chains [14]. Using the PTE structure of Holden and coworkers [15], the inventors generated a symmetric PTE in which all the phenylalanines are replaced with pFF. Using PyRosetta, a python interface to the Rosetta libraries, [16] the inventors then examined every pFF position in the model. Each pFF position was allowed to mutate to any amino acid except phenylalanine. The inventors then evaluated the mutated residue compared to the "native" pFF based on the total energy and predicted binding energy of the two chains (FIG. 1). This protocol was used to predict stabilizing site-specific mutations as well as mutations what would remove phenylalanine positions that would not tolerate pFF substitution. In this embodiment, the residue-specific pFF incorporation system does not allow the inventors to control which phenylalanine positions are fluorinated and thus removing phenylalanine positions that cannot tolerate fluorination could improve stability if alternate natural amino acids score well at the same positions. For each mutation, every neighboring amino acid within 10 Å of the Ca atom of pFF was allowed to repack to accommodate the point mutation by filling in potential high-cost-energy voids or to supplement the hydrophobicity, polarity, or charge in the vicinity (FIG. 2).

Replacing the phenylalanine with pFF at position 104 created energy-costing clashes with neighboring amino acids within the dimer interface (FIG. 2A). As the dimer is known to be important for function [6], the inventors sought re-stabilize the interface caused by the pFF. Upon mutation of F104 to alternative natural amino acids, the inventors identified the pFF-F 104A variant, which exhibits improved packing in the absence of the pFF (FIG. 2A).

The original pFF-F104A variant and pFF-PTE parent were biosynthesized via residue-specific incorporation using the phenylalanine auxotrophic *E. coli* strain AFIQ. [6] In addition, the non-fluorinated counterparts, PTE and F104A, were expressed under conventional conditions as controls (see below). As expected, all four proteins exhibited good expression in the presence of phenylalanine or pFF (FIG. 2B). Both pFF-F104A and pFF-PTE exhibited 80% and 92% incorporation as determined by MALDI-TOF mass spectrometry (FIG. 1, FIG. 3). Notably, purified yields of the pFF-F104A were 2-fold higher than pFF-PTE, indicating more soluble protein yield (FIG. 4).

Circular dichroism (CD) was performed to determine whether the mutation impacted the overall secondary structure and stability. The far-UV wavelength scan of pFF-F104A and pFF-PTE both presented a double minimum at 208 and 222 nm as expected for a (β/α)8-barrel protein, suggesting that the mutation did not affect the overall structure at 25° C. (FIG. 5). Surprisingly, comparison of the non-fluorinated counterparts revealed that F104A was less structured than PTE (FIG. 5). To assess the stability, differential scanning calorimetry (DSC) was performed. Upon heating the sample from 0-70° C., pFF-PTE exhibited two transitions at 42.0±0.1° C. ($T_m1$) and 48.6±0.2° C., consistent with previous studies[6] ($T_m2$; FIG. 6A, FIG. 3). This biphasic unfolding has also been observed previously by Grimsley et al. in the study of organophosphorous hydrolase (EC 8.1.3.1), and attributed to the presence of a dimeric unfolded intermediate [17]. By contrast, pFF-F104A revealed a single transition at 49.7±0.2° C., which was higher than both $T_m$ values by 7.7° C. and 1.1° C., respectively (FIG. 6B, FIG. 3). Remarkably, after heating, pFF-F104A maintained the single $T_m$ of 49.2±0.1° C., re-gaining structure after undergoing thermal unfolding. These data affirm the overall thermodynamic stability of pFF-F104A.

Moreover, in certain embodiments, it further suggests that the unfolding model has been altered from a 3-state to 2-state transition, suggesting that the energy requirement necessary to attaining the unfolded intermediate has been increased, resulting in a more cooperative transition. Mutations resulting in this particular transformation have been observed for other proteins; Fan et al. showed, for example, that the removal of a C-terminal domain of the oligomeric E. coli trigger factor protein, resulted in the transformation in an otherwise n-state unfolding process to a distinct 2-state unfolding process, indicative of pronounced stabilization of the native structure via inter-domain interactions [18]. Without being bound to theory, the pFF-F104A mutation may also be stabilizing the native structure of the overall protein, in effect committing the reverse of the mutation observed by Fan et al. [18]. That is, the pFF-F104A unfolds cooperatively in a single step, concurrent with its dissociation as monomeric species. While it is expected that the pFF-F104A mutation would have an effect on inter-domain stability such that neighbouring residues were allowed to repack and minimize across monomers at the dimer interface, the apparent stabilization of the native structure—concluding from the 3-state to 2-state transition transformation—via these newfound inter-domain interactions were unanticipated. Prior examples of this transformation exist in cases involving subdomains of similar stabilities or if there exists strong coupling between subdomains [19].

Figure 8:
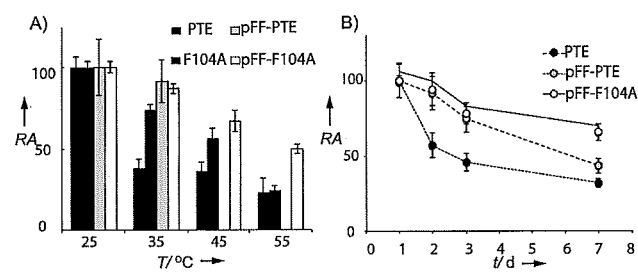
FIG. 8 depicts A) Residual activity (RA) profile of all proteins. B) Half-life or activity measured as a function of days.
Figure 11:
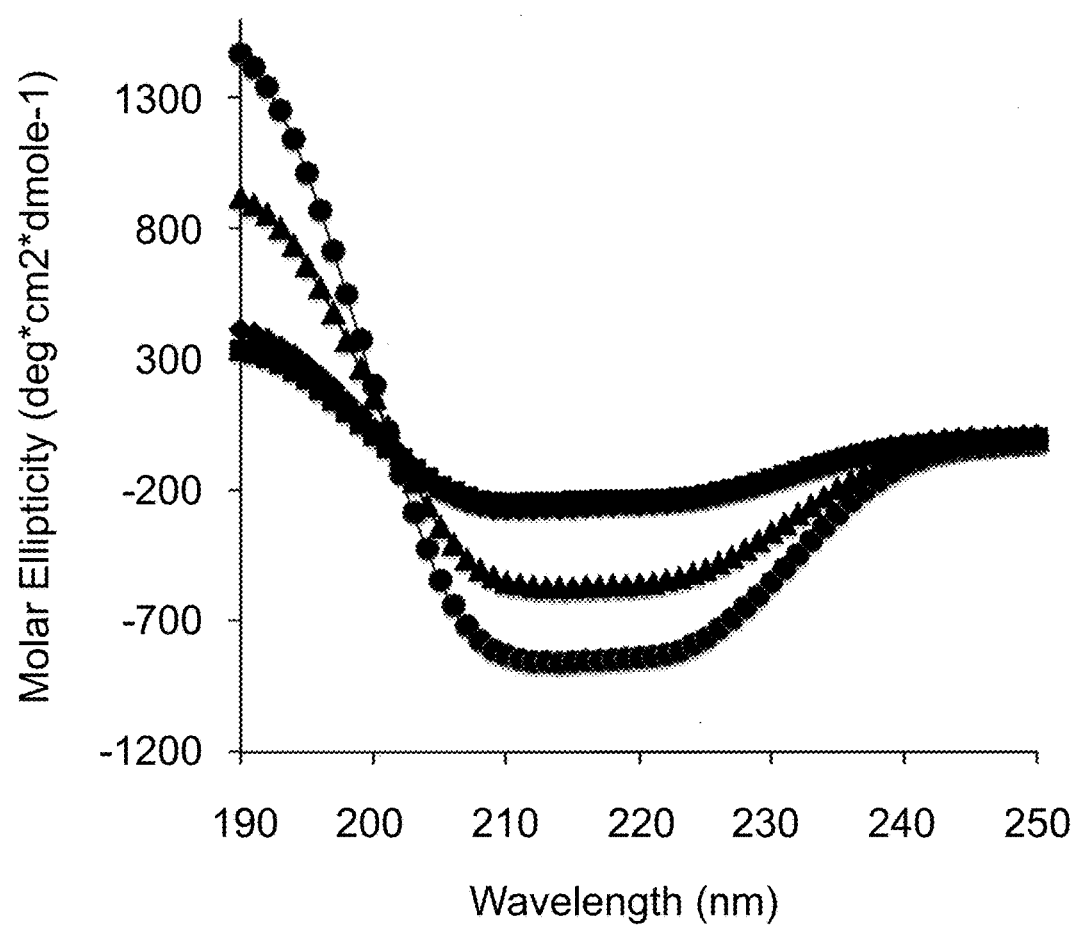
FIG. 11 depicts CD wavelength scans of PTE (circles), 104A (triangles), pFF-PTE (diamonds) and pFF-104A (squares).
Figure 17:
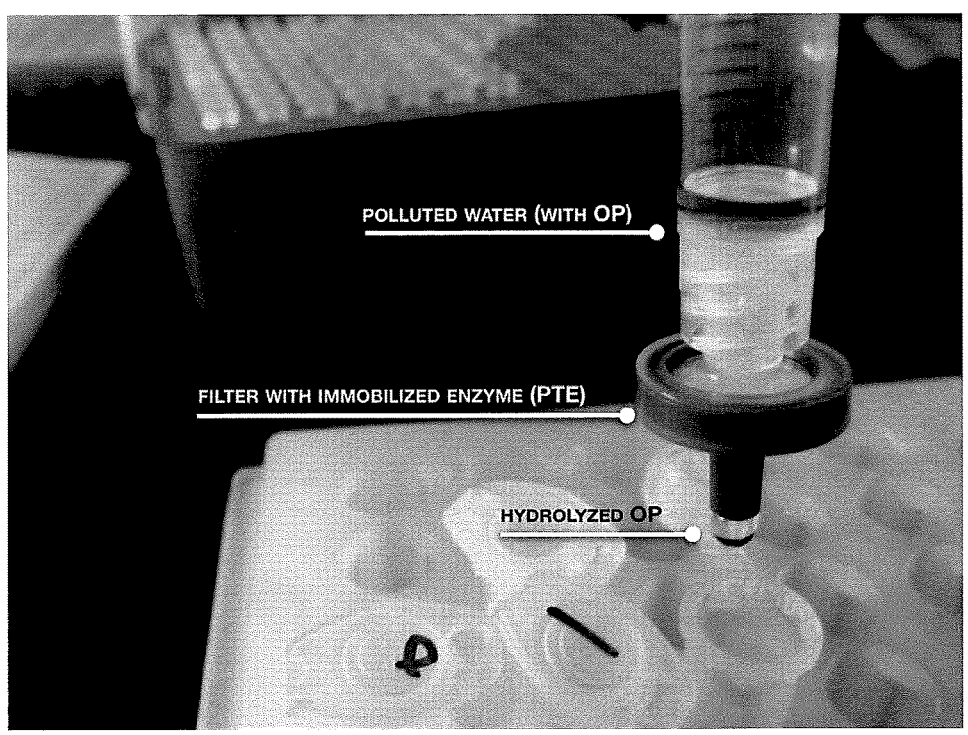
FIG. 17 depicts a filtration system according to an embodiment of the instant invention.

To assess function, the inventors determined the Michaelis-Menten kinetics of pFF-F 104A, pFF-PTE, F104A, and PTE for paraoxon. At 25° C., pFF-PTE exhibited the highest activity with an overall catalytic efficiency ($K_{cat}/K_M$) of 327,000 $s^{-1}$ $M^{-1}$, while pFF-F104A demonstrated a slight loss in $K_{cat}/K_M$ (223,000 $s^{-1}$ $M^{-1}$) (FIG. 7). The non-fluorinated PTE exhibited $K_{cat}/K_M$ of 200,000 s-1 M-1 within the range of both fluorinated proteins, however, F104A exhibited a dramatic loss with a $K_{cat}/K_M$ of 23,000 $s^{-1}$ $M^{-1}$ (FIG. 7). Thus, in this embodiment, the fluorinated amino acids appeared to be necessary for pFF-F104A activity. Proteins were then incubated in 25° C., 35° C., 45° C. and 55° C. for one hour and then cooled back down to room temperature to determine residual activity. A decline in residual activity was observed for all proteins as a function of elevated temperatures. As pFF-F104A was designed to stabilize the fluorinated protein, it exhibited 50% retention of activity at 55° C. (FIG. 8A, FIG. 7). By contrast, pFF-PTE and PTE exhibited 24% and 23% of initial activity at 55° C., respectively; F104A exhibited a rapid loss in activity at 45° C. and above (FIG. 8A, FIG. 7). As pFF-F104A maintained substantial residual activity at elevated temperatures, the inventors then investigated the half-life of activity. The parent pFF-PTE exhibited >50% loss in activity after 3 days while the non-fluorinated PTE showed >50% activity reduction after 7 days (FIG. 8B, FIG. 9). Remarkably, pFF-F104A still maintained 66% activity after 7 days (FIG. 8B, FIG. 9). The non-fluorinated F104A counterpart failed to exhibit activity after one day (FIG. 9). Together this data confirms that pFF-F104A is able to delay heat inactivation while also maintain function after one week.

Experimental Section

Materials: All chemicals, reagents, and substrate were purchased from Sigma (St. Louis, Mo.). T4 DNA ligase was purchased from Roche (Indianapolis, Ind.). DNA sequence was confirmed by Eurofins MWG Operon. 96-well plates were purchased from Thermo Fisher Scientific (Waltham, Mass.).

Computational Modeling: Rosetta[1] was used to generate a symmetric, pFF-incorporated PTE structure used by all simulations. The Holden and coworkers structure (PDB code: 1HZY) of wild type PTE was used as the input. In addition to the phenylalanine positions being mutated to pFF, three positions in the wild-type PTE sequence were mutated (K185R, D208G, and R319S) to generate pFF-S5PTE [2]. Mutations were made using the Rosetta fixbb application and were followed by side chain repacking and minimization. The amino acids directly interacting with the $Co^{2+}$ ions are important in binding the necessary divalent cation for PTE activity [3], so they were fixed in their native rotamers during repacking and minimization. PyRosetta, a python interface to the Rosetta libraries [4], was used to make and characterize point mutations. Every pFF position was individually mutated into any natural amino acid minus phenylalanine. To simulate a mutation, a single pFF position would be mutated and neighboring amino acid within 10 Å (as measured by Cα-Cα atom distance) was allowed to repack and minimize to accommodate the point mutation to fill in potential high-cost-energy voids or to supplement the hydrophobicity, polarity, or charge in the vicinity. For each pFF position, 500 decoys were generated. After the mutations were made, representative structures of each mutation were chosen based on the overall stability of the enzyme, reflected by the total score. The binding energy is the total energy minus the energy of both monomers separated by 1000 Å. Point mutations were chosen based on the difference between relative total and predicted binding energies of the mutant and pFF-S5PTE sequence. As above, amino acids directly interacting with the $Co^{2+}$ ions were fixed in their native rotamers during repacking and minimization. All Rosetta and PyRosetta calculations were done using the score 12 score function, and included extra rotamer sampling, including the native rotamers.

PTE cloning: pQE30-S5 was used as described before. The pQE30-F104A plasmid was prepared with forward primers (5'-GATGTGTCGACTGCCGATATCGGTCG-3' (SEQ ID NO: 65), Fisher Scientific), reverse primers (5'-CGACCGA-TATCGGCAGTCGACACA-3' (SEQ ID NO: 66), Fisher Scientific). The PCR parameters were set as follows for 18 cycles: initial denaturation in 95° C. for 30 seconds, sequential denaturation in 95° C. for 30 seconds, annealing in 55° C. for 1 minute, and extension in 68° C. for 4 minutes. The mixture was then incubated 37° C. overnight with DpnI to digest methylated parent DNA strands, which lack the desired mutation. DNA sequence was further confirmed by Eurofins MWG Operon.

Protein expression and purification: Mutant and wild type plasmids were transformed into E. coli phenylalanine auxotrophic strains (AF-IQ cells). [5] Electroporation was done at 25 μF, 100 Ohms, 2.5 kV (Biorad Gene Pulser II). Cells were plated on agar plates containing 200 μg/mL ampicillin, 34 μg/mL chloramphenicol. A single colony was picked and grown in medium (M9 medium supplemented with 0.2 wt % glucose, 35 mg/L thiamine, 1 mM MgSO4, 0.1 mM CaCl2, 200 μg/mL ampicillin, and 34 μg/mL chloramphenicol) with 20 mg/L of 20 amino acids at 37° C., 300 r.p.m. Afterwards, 250 mL of M9 medium for large-scale expression was innoculated 1:50 with an overnight culture. After optical density reached 1.0 at 600 nm, media shift was carried out by washing the cells three times with 0.9% 4° C. NaCl. Cells were then transferred to M9 minimal medium containing either 20 amino acids or 19 amino acids (-Phe). pFF-PTE and pFF-104A expression media were supplemented with 3 mM of pFF and 1 mM isopropyl-beta-D-thiogalactopyranoside (IPTG) to induce protein expression. 1 mM of $CoCl_2$ was added in each post-induction medium. After three hours incubation at 37° C., 300 r.p.m., the cells were harvested and then resuspended with 20 mM Tris-HCl, 500 mM NaCl, 5 mM imidazole, 10% glycerol (pH 8.0) and 1 μM $CoCl_2$. Cell lysate was sonicated on ice for 1.5 minutes and then a clarification spin was performed (20,000 g, 4° C., 30 min). Clarified supernatants were loaded into a His Trap column (G.E Healthcare, Piscataway, N.J.) using ÄKTA FPLC purifier (G.E. Healthcare, Piscataway, N.J.). Protein elution was generated using elution buffer B (20 mM Tris-HCl, 500 mM sodium chloride, 500 mM imidazole (pH 8.0)). The purified samples were then transferred for buffer exchange using 3×4 L 20 mM phosphate buffer (pH 8.0). Dialyzed protein was subjected to kinetic assays immediately.

Determining incorporation of fluorinated amino acid: To determine level of p-fluorophenylalanine incorporation, 20 μL of purified PTE pFF-PTE, F104A, or pFF-104A was incubated with 12.5 ng/μL, of trypsin solution (in 50 mM of ammonium bicarbonate) at 37° C. overnight. 2 μL of 10% trifluoroacetic acid (TFA) was used to quench each reaction. Reaction was then purified with a C18 packed zip-tip (Millipore, Billerica, Mass.). Tips were wetted in 50% acetonitirile (ACN), equilibrated in 0.1% TFA, and eluted with 0.1% TFA in 75% ACN. Matrix was dissolved in 10 mg/mL α-cyano-4-hydrocinnamic acid (CCA) in 50 ACN, 0.05% TFA. Theoretical trypsin digest were calculated from Peptide Mass (www(dot)expasy(dot)org/tools/peptide-mass(dot)html). Samples were added to the matrix at a 1:1 ratio and spotted on MALDI plate. Five standards were spotted separately for calibration: angiotensin I (MW=1295.69 g/mol), neurotensin (MW=1671.92 g/mol), ACTH (1-17) (MW=2092.09 g/mol), ACTH (18-39) (MW=2464.20 g/mol), and ACTH (7-38) (MW=3656.93 g/mol). Compass 1.4 for flex software was then used to analyze the MALDI spectra (www(dot)bruker(dot)com/).

Kinetics: The protein was diluted to a final concentration of 30 nM in 20 mM sodium phosphate (pH 8.0) by using the extinction coefficient 29,280 $M^{-1}$ $cm^{-1}$. Reactions were monitored spectrophotometrically (Synergy H1, Bio-Tek, Winooski, Vt.) at 405 nm for paraoxon (coefficient=17,000 $M^{-1}$ $cm^{-1}$). Reactions for paraoxon (13-104 μM) were done in 0.4% methanol. $K_M$ and $k_{cat}$ values were determined by a Lineweaver-Burk plot (1/v vs 1/[S]).[5] The equation used is shown below:

$$1/v=(K_M/V\text{Max})*(1/[S])+1/V\text{Max}$$

where [S] represents substrate concentration; $K_M$ represents the substrate concentration at which the reaction rate is half of $V_{max}$. The data reported is the average of three trials and the error represents the standard deviation of those trials.

Circular dichroism: CD spectra were recorded on a JASCO J-815 Spectropolarimeter (Easton, Md.) using Spectra Manager software. Temperature was controlled using a Fisher Isotemp Model 3016S water bath. Protein concentrations were 10 μM in 20 mM phosphate buffer (pH 8.0). 20 mM phosphate buffer was used for blanking signals. To calculate ellipticities, the following formula was used:

$$\theta_{mrw}=MRW(\theta_{obs})/(10*c*1)$$

where MRW is the mean residue weight of the specific phosphotriesterase, $\theta_{obs}$ is the observed ellipticities (mdeg), 1 is the path length (cm), c is the concentration in μM. Spectra were recorded from 190 nm to 250 nm with a scan speed of 1 nm/min.

Differential scanning calorimetry: DSC (Nano-DSC, TA instrument, USA) was performed by using 600 μL (0.1 mg/mL) of protein right after dialysis. Measurements were conducted at a scan rate of 1° C./min. Signals were blanked with buffer under the same conditions. The observed diagram was then analyzed by using NanoAnalyze software.

Example 2

Organophosphate Decontamination Device

Organophosphate decontamination device:
(a) polluted water: a chamber or pipeline that contains liquid with organophosphates;
(b) filter polluted water of (a) with immobilized PTE: PTE is immobilized with cobalt beads by 6× His Tag (SEQ ID NO: 67). After incubation (any temperatures ranging from about 4° C. to 37° C.) for five minutes, beads are then applied to the filter device with a filter paper (pore is smaller than the beads); and
(c) reaction: organophosphates are then hydrolyzed by PTE.

Example 3

Colorimetric Assay

Described herein is a colorimetric assay in which a small molecule pH indicator that upon liberation of acid from hydrolysis of any ester, would exhibit a visible color change. The cell-permeable small molecule, 3-amino-7-dimethyl-amino-2-methylphenazine hydrochloride (neutral red), is selected as the pH indicator as it will change from yellow to red at pH of 6.8 or below. This would then allow the detection of esters that do not possess a colorimetric or fluorescent tag.

Figure 18:
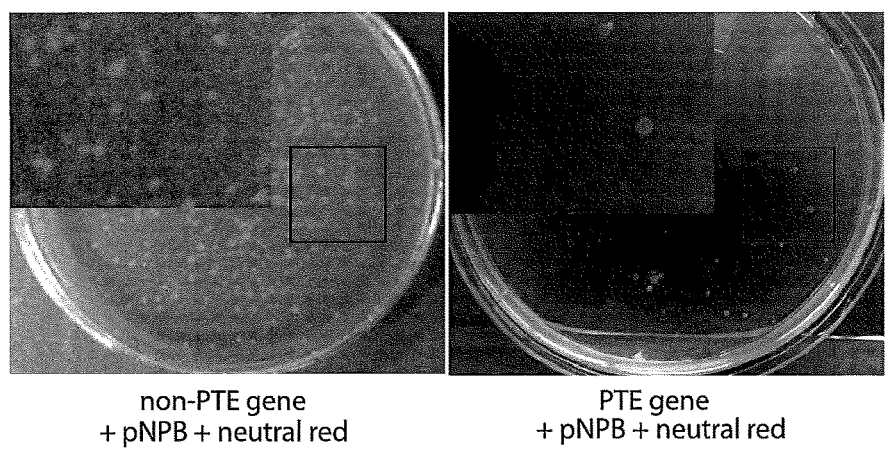
FIG. 18 depicts a colorimetric plate assay of plates bearing PQE-PTE in the presence (left) and absence (right) of IPTG (left) with a test substrate pNPB and neutral red.

In a first step towards effectively employing this assay, freshly transformed AFIQ cells bearing PTE were grown on TSA plates bearing 1 mM IPTG, 200 μg/mL ampicillin and 34 μg/mL chloramphenicol overnight at 37° C. To this, a layer of soft agar (0.5% agar in water) containing 1 mM of para-nitrophenylbenzoate (pNPB) and 30 μg/mL of neutral red was added and after reaction assessed for color change. Cells bearing PTE all exhibited pink/red colonies in the presence of pNPB, while cells bearing a non-PTE gene EC (negative control) were off-white under the identical conditions (see FIG. 18).

Example 4

PTE Lactose Crystal Formulation

Formulations that stabilize a PTE of the instant invention have been investigated. In some embodiments, the formulation enables the development of a powder or spray for the removal of pesticides from agricultural product. The below formulations involve the co-crystallization of a PTE of the invention with alpha lactose (LM). Preliminary data of PTE.LM crystals after 2 months storage in comparison to demonstrate hydrolysis of paraoxon when the protein stored in buffer is inactive.

Figure 19:
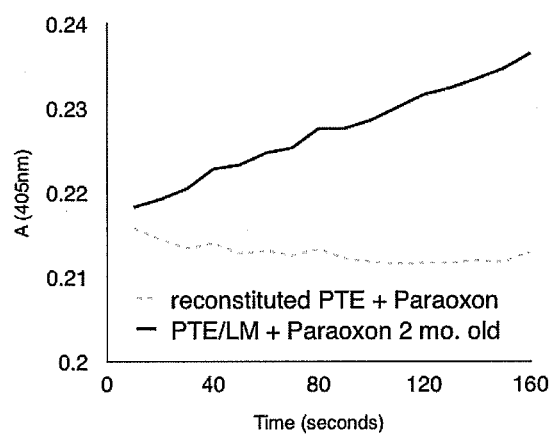
FIG. 19 is a graph depicting activity comparisons of 0.3 g/mL PTE.LM crystal and 3.75 µM PTE in buffer solution (ZZ) stored at room temperature for 2 months. The reaction of paraoxon hydrolysis was monitored at wavelength 405 nm.
Figure 20:
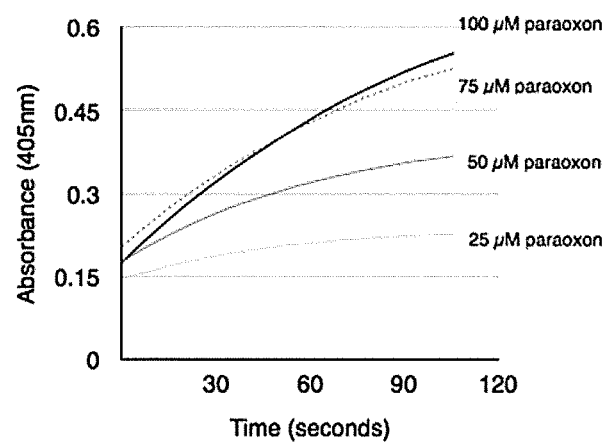
FIG. 20 is a graph depicting the paraoxon hydrolysis reaction of reconstituted 0.08 g/mL PTE.LM crystal. The reaction was monitored at wavelength 405 nm. The PTE.LM crystal was stored at room temperature for ~3.5 months.

More particularly, enhanced stability of PTE.LM crystals was observed even after storage at room temperature over 3.5 months. After 0.08 g/mL PTE.LM crystals was reconstituted in 20 mM phosphate buffer, hydrolysis of 50-100 uM paraoxon (0.4% methanol) was then used for assays. Within three minutes, reactions reached the maximum absorbance at 405 nm. Results are presented in FIGS. 19 and 20. While the PTE.LM crystals were reconstituted in phosphate buffer, it is noted that any suitable buffer may be used.

PTE.LM crystals were prepared as follows:

Alpha-Lactose monohydrate (ALM) as purchased from Sigma-Aldrich was dissolved in PBS (NaCl, KCl, $KH_2PO_4$, $Na_2HPO_4$) 1× buffer pH 7.4 at 70-100° C. Then solution was cooled down to room temperature and 0.20 mg of purified PTE was added to get ALM concentration 0.28 g/g buffer. Crystallization was performed in a fridge at 2-6° C. and took 2.5 weeks. Powder lactose monohydrate was used as the seed for crystallization. Crystals were harvested, washed with distilled water, and dried at room temperature. PTE crystals were stored at 4° C. or room temperature.

Some of the conditions to vary are as follows. Sometimes ALM is deionized using columns with both cation-exchange and anion-exchange resins. Instead of PBS 1×, water, PBS at different concentrations, and other buffers can be used in order to tune pH and salt concentration. Concentration of ALM varies from 0.24 to 0.5 g/g buffer. Experiment duration: from few hours up to 1 month. Sometimes crystallization is performed at room temperature and even at 36° C. (in this case, concentration of ALM in solution is higher).

Example 5

PTE Efficacy Against Pesticides

Testing of engineered PTE variants of the instant invention can be conducted on any number of various pesticides, including chlorpyrifos, acephate, malathion, ethion, and profenofos. Pesticides such as these can be assayed with the PTE variants of the instant invention. In some embodiments, the Code of Federal Regulations (CFR) is used as a reference regarding information on the control of pesticides in the United States, including details regarding the tolerances of different pesticides for each different category of agricultural product. In particular embodiments, the PTE variants of the instant invention are assayed for efficacy against pesticides against those products that have a low tolerance as designated by the CFR. In some embodiments, the effectiveness of a PTE variant of the instant invention is determined in assays involving the detection of a variety of pesticides on MS/LC, with detection limits as low as 25-50 ppb. The effectiveness of the PTE variants tested against one or more pesticides can be assessed in accordance with the tolerances illustrated in the CFR.

Example 6

Re-Engineering Fluorinated PTE Using Rosetta

PTE variants designed specifically for chlorpyrifos have been developed. A starting model for use with Rosetta design capabilities was derived from PDB structure 1HZY (1.30 Å). The starting model zinc ions were replaced by cobalt in the active site and initial geometry was taken from PDB structure 3A4J, a dual cobalt ion coordinating enzyme. Three beneficial mutations (K185R, D208G, R319S) were introduced into the base model to coincide with a laboratory version of PTE. For the ligand, chemical parameters for chlorpyrifos (dihedral torsional potentials and atomic partial charges) were generated with quantum mechanical calculations. The active site with residues capped at CA and chlorpyrifos docked in position for chemistry was geometrically optimized using the software Gaussian09 at the B3LYP/6-31+G(d) level of theory.

Figure 21:
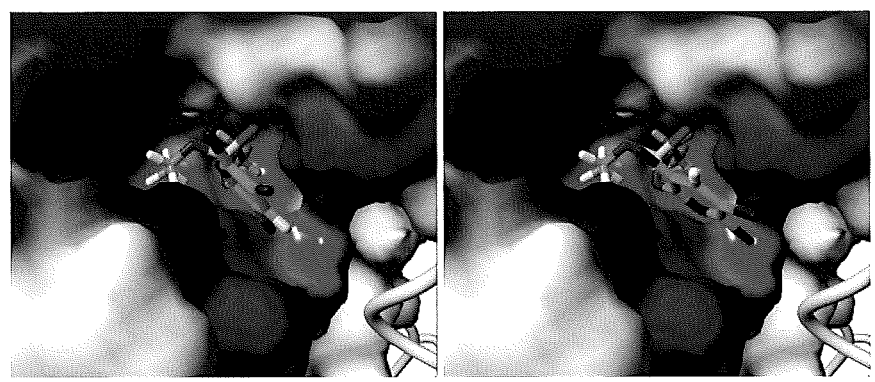
FIG. 21. Chlorpyrifos (chlorine in gray, phosphorus in very light gray, sulfur in light gray) orients its halogenated leaving group in one of two ways when docked with its phosphate group in the correct orientation for chemistry. The first conformation has the single meta-hydrogen pointing toward the other chain of the dimer visible as a tube in the lower right corner (A). The second conformation binds more strongly than the first and has the meta-hydrogen pointing directly out of the active site. The colors of the molecular surface depict the identified regions of the binding pocket. Dark gray: large pocket, light gray: small pocket, medium gray: leaving group pocket.

Docking simulations with Rosetta Ligand Dock have revealed two possible catalytically relevant binding orientations (FIG. 21). Both conformations orient the phosphate for nucleophilic attack by a hydroxide ion coordinated between two cobalt cations in accordance with current theoretical mechanisms for hydrolysis of organophosphates by PTE. While docking revealed other energetically favorable docked orientations, those that support the right geometry for catalysis were focused on. The leaving group of chlorpyrifos is a six membered ring with a nitrogen in the ortho position and three chlorine atoms bonded to the ring carbons. The asymmetric ring can orient itself between the residues of the leaving pocket (131, 132, 306, 309) in one of two ways. Ligand binding scores calculated using Rosetta's talaris 2013 energy function suggest that the second of the two orientations (conformation 2) is more favored in the unmodified enzyme (FIG. 21B).

To find mutations that improve the docking score of chlorpyrifos over the wild type, Rosetta design runs are carried out using alternate rounds of fixbb (fixed backbone) design protocol and the fast relax (structure refinement and optimization) protocol. 16 different sets of residues were initially targeted for design including, the small pocket (60, 106, 303, 308), the large pocket (254, 257, 271, 317), the leaving pocket, and all residues within 5 Å of the ligand. Additionally, some design runs included mutations previously identified in PTE as both kinetically and stereochemically beneficial such as the VRN-VQFL mutations identified by Bigley, A N et al. J Am Chem Soc (2013) July 17; 135(28):10426-32.

In this embodiment, a PTE using non-canonical fluorinated amino acids at the dimer interface was desired. Therefore, many design runs excluded the possibility of mutation to phenylalanine since it was believed that inclusion of p-fluorophenylalanine at positions outside of the dimer interface have a structurally destabilizing effect.

In half of all design runs, phenylalanine 306, located in the large pocket, was excluded from design and instead mutated to leucine. The inventors have recently identified this mutation as both stabilizing and rate enhancing with both simulations and experiments.

Figure 22:
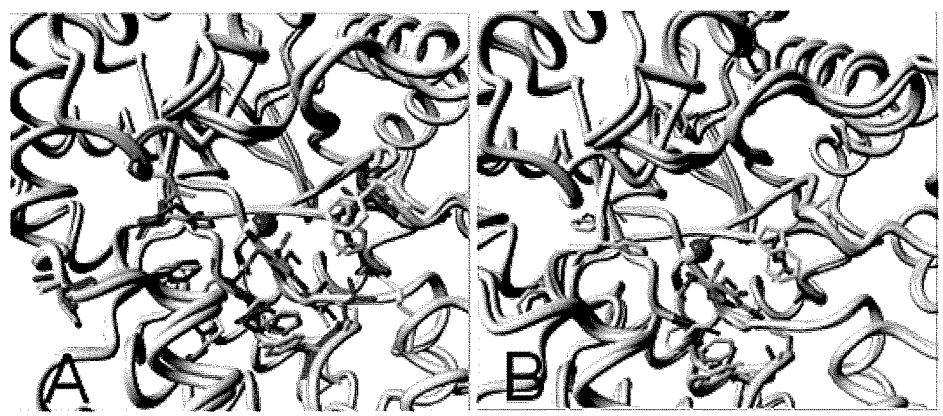
FIG. 22. The residue positions mutated in the best designed sequences after several iterations of design and relax. Loop 7 is in the lower left and the spheres are the active site hydroxide ion. Designs are derived from decoy structures CP5CPF-1_050214 (A) and CP5CPF-2_120049 (B). Wild type residues are in very light gray and mutated residues are in dark gray over the structure. Many of the same positions are mutated for both chlorpyrifos orientations.

For docked conformation 1, Rosetta design has identified several unique mutation sets that improve the binding score of chlorpyrifos to PTE (Table 1A in FIG. 23). The best of these improves the binding of chlorpyrifos by −2.6895 REU (Rosetta Energy Units). The positions of the altered residues for this design are highlighted in FIG. 22A. Mutation to phenylalanine was not restricted for the two structures presented in FIG. 22. In certain further embodiments, iterations remove them one position at a time, mutating other positions to compensate.

For docked conformation 2, Rosetta design has identified fewer mutations that improve chlorpyrifos binding (Table 1B in FIG. 23). The best improvement in binding energy has so far been −1.7696 REU. The mutated positions for that sequence are highlighted in FIG. 22B.

In some embodiments, more extensive sampling of both conformational space and sequence space is conducted for docked conformation 2. Examination of the data reveal that conformation 2 was sampled less than half as much as conformation 1 just by virtue of being second in the list. Because Rosetta's Monte Carlo based sampling algorithms are stochastic, greater improvement can generally be obtained with more extensive sampling.

Because conformation 2's binding scores to the native enzyme have been revealed as significantly better than those of conformation 1, in further embodiments, design efforts target conformation 2 more aggressively. In other embodiments, a rotamer library that favors the internal angle configuration of conformation 2 is built.

In some embodiments, to expedite synthesis of a designed PTE, the number of residues that need to be mutated is kept to a minimum, targeting approximately five positions if possible. Close examination of the energetic contributions for each residue, in the form of Rosetta score function components, may allow exclusion of mutations with minimal contribution to binding affinity. Additionally, the search algorithm may be handicapped by searching a large sequence space because the possibilities grow exponentially with each mutatable position. Accordingly, in some embodiments, binding improvement may be possible by searching a smaller space more exhaustively.

In some embodiments, the ability to mutate residues is added to a variation of Rosetta's fast relax protocol allowing full backbone movement and optimization while simultaneously sampling with rotamers unrestricted to their starting identity.

In other embodiments, simulations are conducted for a chlorpyrifos binding PTE design that includes p-fluorophenylalanine at the dimer interface. In certain embodiments, the interactions of p-fluorophenylalanine with chlorpyrifos within the binding pocket itself are evaluated using simulations that include p-fluorophenylalanine in an expanded rotamer library.

In yet other embodiments, it is desirable to carry out thermodynamic sampling of PTE variant structures using AMBER force field based MD simulations. This technique has been successfully used to rank other enzymes designs in order of probable success.

In some embodiments, the PTE variants corresponding to the protein sequences provided in FIG. 24 may be effective in chlorpyrifos binding.

REFERENCES

[1] a) N. Voloshchuk, J. K. Montclare, Mol. BioSys. 2010, 6, 65-80; b) H. T. More, C. Y. Yang, J. K. Montclare, in Functional Polymers by Post-Polymerization Modification: Concepts, Guidelines, and Applications (Ed.: P. A. K. Theato, H. A.), Wiley-VCH Verlag GmbH & Co. KGaA, Weinheim Germany, 2013.

[2] a) Y. Tang, G. Ghirlanda, W. A. Petka, T. Nakajima, W. F. DeGrado, D. A. Tirrell, Angew. Chem. Int. Ed. 2001, 40, 1494-1496; b) Y. Tang, D. A. Tirrell, J. Am. Chem. Soc. 2001, 123, 11089-11090; c) J. K. Montclare, S. Son, G. A. Clark, K. Kumar, D. A. Tirrell, ChemBioChem 2009, 10, 84-86; d) S. Son, I. C. Tanrikulu, D. A. Tirrell, ChemBioChem 2006, 7, 1251-1257.

[3] a) N. Voloshchuk, A. Y. Zhu, D. Snydacker, J. K. Montclare, Bioorg. Med. Chem. Lett. 2009, 19, 5449-5451; b) T. Panchenko, W. W. Zhu, J. K. Montclare, Biotech. Bioeng. 2006, 94, 921-930; c) N. Voloshchuk, M. X. Lee, W. W. Zhu, I. C. Tanrikulu, J. K. Montclare, Bioorg. Med. Chem. Lett. 2007, 17, 5907-5911; d) K. R. Mehta, C. Y. Yang, J. K. Montclare, Mol. BioSys. 2011, 7, 3050-3055; e) J. T. Hammill, S. Miyake-Stoner, J. L. Hazen, J. C. Jackson, R. A. Mehl, Nature Prot. 2007, 2, 2601-2607; f) N. Budisa, W. Wenger, B. Wiltschi, Mol. BioSys. 2010, 6, 1630-1639; g) M. G. Hoesl, C. G. Acevedo-Rocha, S. Nehring, M. Royter, C. Wolschner, B. Wiltschi, N. Budisa, G. Antranikian, ChemCatChem 2011, 3, 213-221; h) L. Merkel, M. Schauer, G. Antranikian, N. Budisa, ChemBioChem 2010, 11, 1505-1507; i) B. Holzberger, A. Marx, J. Am. Chem. Soc. 2010, 132, 15708-15713.

[4] C. Yuvienco, H. T. More, J. S. Haghpanah, R. S. Tu, J. K. Montclare, Biomacromolecules 2012, 13, 2273-2278.

[5] J. K. Montclare, D. A. Tirrell, Angew. Chem. Int. Ed. 2006, 45, 4518-4521.

[6] P. J. Baker, J. K. Montclare, ChemBioChem 2011, 12, 1845-1848.

[7] A. Leaver-Fay, M. Tyka, S. M. Lewis, 0. F. Lange, J. Thompson, R. Jacak, K. W. Kaufman, P D. Renfrew, C. A. Smith, W. Sheffler, I. W. Davis, S. Cooper, A. Treuille, D. J. Mandell, F. Richter, Y. A. Ban, S. J. Fleishman, J. E. Corn, D. E. Kim, S. Lyskov, M. Berrondo, S. Mentzer, Z. Popovie J. J. Havranek, J. Karanicolas, R. Das, J. Meiler, T. Kortemme, J. J. Gray, B. Kuhlman, D. Baker, P. Bradley, Methods Enzymol. 2011, 487, 545-574. [8] a) I. W. Davis, D. Baker, J. Mol. Biol. 2009, 385, 381-392; b) I. W. Davis, K. Raha, M. S. Head, D. Baker, Protein Sci. 2009, 18, 1998-2002.

[9] a) A. E. Miklos, C. Kluwe, B. S. Der, S. Pai, A. Sircar, R. A. Hughes, M. Berrondo, J. Xu, V. Codrea, P. E. Buckley, A. M. Calm, H. S. Welsh, C. R. Warner, M. A. Zacharko, J. P. Carney, J. J. Gray, G. Georgiou, B. Kuhlman, A. D. Ellington, Chem. Biol. 2012, 19, 449-455; b) G. Dantas, B. Kuhlman, D. Callender, M. Wong, D. Baker, J. Mol. Biol. 2003, 332, 449-460; c) G. Dantas, C. Corrent, S. L. Reichow, J. J. Havranek, Z. M. Eletr, N. G. Isern, B. Kuhlman, G. Varani, E. A. Merritt, D. Baker, J. Mol. Biol. 2007, 366, 1209-1221.

[10] a) L. A. Joachimiak, T. Kortemme, B. L. Stoddard, D. Baker J. Mol. Biol. 2006, 361, 195-208; b) P. B. Stranges, M. Machius, M. J. Miley, A. Tripathy, B. Kuhlman, Proc. Natl. Acad. Sci. USA 2011, 108, 20562-20567.

[11] B. Kuhlman, G. Dantas, G. C. Ireton, G. Varani, B. L. Stoddard, D. Baker, Science 2003, 302, 1364-1368.

[12] F. Richter, A. Leaver-Fay, S. D. Khare, S. Bjelic, D. Baker, PloS One 2011, 6, e19230.

[13] S. D. Khare, Y. Kipnis, P. Greisen, Jr., R. Takeuchi, Y. Ashani, M. Goldsmith, Y. Song, J. L. Gallaher, I. Silman, H. Leader, J. L. Sussman, B. L. Stoddard, D. S. Tawfik, D. Baker, Nature Chem. Biol. 2012, 8, 294-300.

[14] P. D. Renfrew, E. J. Choi, R. Bonneau, B. Kuhlman, PloS One 2012, 7, e32637.

[15] M. M. Benning, H. Shim, F. M. Raushel, H. M. Holden, Biochemistry 2001, 40, 2712-2722.

[16] C. Sidhartha, S. Lyskov, J. J. Gray, Bioinformatics 2010, 26, 689-691.

[17] J. K. Grimsley, J. M. Scholtz, C. N. Pace, J. R. Wild, Biochemistry 1997, 36, 14366-14374.

[18] D.-J. Fan, Y.-W. Ding, X.-M. Pan, J.-M. Zhou, Biochim. Biophys. Acta 2008, 1784, 1728-1734.

[19] M. Tsytlonok, L. S. Itzhaki, Arch. Biochem. Biophys. 2013, 531 14-23.

[20] T. H. Yoo, A. J. Link, D. A. Tirrell, Proc. Natl. Acad. Sci. USA 2007, 104, 13887-13890.

[21] a) O. Khersonsky, D. Röthlisberger, A. M. Wollacott, P. Murphy, O. Dym, S. Albeck, G. Kiss, K. N. Houk, D. Baker, D. S. Tawfik, J. Mol. Biol. 2011, 407, 391-412; b) J. D. Bloom, M. M. Meyer, P. Meinhold, C. R. Otey, D. MacMillan, F. H. Arnold, Curr. Op. Struct. Biol. 2005, 15, 447-452; c) E. M. Brustad, F. H. Arnold, Curr. Op. Chem. Biol. 2011, 15, 201-210.

22. Hill, C. M., W. S. Li, T. C. Cheng, J. J. DeFrank, and F. M. Raushel, Stereochemical specificity of organophosphorus acid anhydrolase toward p-nitrophenyl analogs of soman and sarin. Bioorganic Chemistry, 2001. 29(1): p. 27-35.

23. Li, W. S., K. T. Lum, M. Chen-Goodspeed, M. A. Sogorb, and F. M. Raushel, Stereoselective detoxification of chiral sarin and soman analogues by phosphotriesterase. Bioorganic & Medicinal Chemistry, 2001. 9(8): p. 2083-2091.

24. Li, W. S., Y. C. Li, C. M. Hill, K. T. Lum, and F. M. Raushel, Enzymatic synthesis of chiral organophosphothioates from prochiral precursors. Journal of the American Chemical Society, 2002. 124(14): p. 3498-3499.

25. Raushel, F. M. and H. M. Holden, Phosphotriesterase: An enzyme in search of its natural substrate. Advances in Enzymology, Vol 74, 2000. 74: p. 51-+.

26. Raushel, F. M., Bacterial detoxification of organophosphate nerve agents. Current Opinion in Microbiology, 2002. 5(3): p. 288-295.

27. Griffiths, A. D. and D. S. Tawfik, Directed evolution of an extremely fast phosphotriesterase by in vitro compartmentalization. Embo Journal, 2003. 22(1): p. 24-35.

28. Hill, C. M., W. S. Li, J. B. Thoden, H. M. Holden, and F. M. Raushel, Enhanced degradation of chemical warfare agents through molecular engineering of the phosphotriesterase active site. Journal of the American Chemical Society, 2003. 125(30): p. 8990-8991.

29. Li, Y. C., S. D. Aubert, and F. M. Raushel, Operational control of stereoselectivity during the enzymatic hydrolysis of racemic organophosphorus compounds. Journal of the American Chemical Society, 2003. 125(25): p. 7526-7527.

30. Aubert, S. D., Y. C. Li, and F. M. Raushel, Mechanism for the hydrolysis of organophosphates by the bacterial phosphotriesterase. Biochemistry, 2004. 43(19): p. 5707-5715.

31. Hong, S. B. and F. M. Raushel, Control of stereoselectivity in phosphotriesterase. Protein Engineering, 2004. 388: p. 256-266.

32. Li, Y. C., S. D. Aubert, E. G. Maes, and F. M. Raushel, Enzymatic resolution of chiral phosphinate esters. Journal of the American Chemical Society, 2004. 126(29): p. 8888-8889.

33. Raushel, F. M., Engineered variants of phosphotriesterase for enhanced detoxification of organophosphate nerve agents. Toxicology and Applied Pharmacology, 2004. 197(3): p. 136.

34. Ghanem, E. and F. M. Raushel, Detoxification of organophosphate nerve agents by bacterial phosphotriesterase. Toxicol Appl Pharmacol, 2005. 207(2 Suppl): p. 459-70.

35. Tsai, P. C., A. Bigley, Y. C. Li, E. Ghanem, C. L. Cadieux, S. A. Kasten, T. E. Reeves, D. M. Cerasoli, and F. M. Raushel, Stereoselective Hydrolysis of Organophosphate Nerve Agents by the Bacterial Phosphotriesterase. Biochemistry, 2010. 49(37): p. 7978-7987.

36. Tsai, P. C., Y. B. Fan, J. Kim, L. J. Yang, S. C. Almo, Y. Q. Gao, and F. M. Raushel, Structural Determinants for the Stereoselective Hydrolysis of Chiral Substrates by Phosphotriesterase. Biochemistry, 2010. 49(37): p. 7988-7997.

37. Roodveldt, C. and D. S. Tawfik, Shared promiscuous activities and evolutionary features in various members of the amidohydrolase superfamily. Biochemistry, 2005. 44(38): p. 12728-12736.

38. Seibert, C. M. and F. M. Raushel, Structural and catalytic diversity within the amidohydrolase superfamily Biochemistry, 2005. 44(17): p. 6383-6391.

39. Holm, L. and C. Sander, Protein folds and families: sequence and structure alignments. Nucleic Acids Res, 1999. 27(1): p. 244-7.

40. Benning, M. M., H. Shim, F. M. Raushel, and H. M. Holden, High resolution X-ray structures of different metal-substituted forms of phosphotriesterase from *Pseudomonas diminuta*. Biochemistry, 2001. 40(9): p. 2712-2722.

41. Chen-Goodspeed, M., M. A. Sogorb, F. Y. Wu, S. B. Hong, and F. M. Raushel, Structural determinants of the substrate and stereochemical specificity of phosphotriesterase. Biochemistry, 2001. 40(5): p. 1325-1331.

42. Hong, S. B. and F. M. Raushel, Stereochemical constraints on the catalytic hydrolysis of organophosphate nerve agents by phosphotriesterase. Phosphorus Sulfur and Silicon and the Related Elements, 1999. 146: p. 521-524.

43. Donarski, W. J., D. P. Dumas, D. P. Heitmeyer, V. E. Lewis, and F. M. Raushel, Structure Activity Relationships in the Hydrolysis of Substrates by the Phosphotriesterase from *Pseudomonas-Diminuta*. Biochemistry, 1989. 28(11): p. 4650-4655.

44. Dumas, D. P., S. R. Caldwell, J. R. Wild, and F. M. Raushel, Purification and Properties of the Phosphotriesterase from *Pseudomonas-Diminuta*. Journal of Biological Chemistry, 1989. 264(33): p. 19659-19665.

Having thus described in detail embodiments of the present invention, it is to be understood that the invention defined by the above paragraphs is not to be limited to particular details set forth in the above description as many apparent variations thereof are possible without departing from the spirit or scope of the present invention.

Each patent, patent application, and publication cited or described in the present application is hereby incorporated by reference in its entirety as if each individual patent, patent application, or publication was specifically and individually indicated to be incorporated by reference.

What is claimed is:

1. An isolated mutated phosphotriesterase enzyme (PTE), comprising at least two mutations in comparison to a PTE of SEQ ID NO:1, wherein at least one mutation is a change of a natural amino acid to a different natural amino acid and wherein at least a second mutation is change of a natural amino acid to a non-canonical amino acid (NCAA), wherein the mutated PTE has at least 85% homology with the wild type PTE, and wherein the mutated PTE exhibits enhanced activity at elevated temperatures relative to SEQ ID NO:1, and/or maintains activity in solution at room temperature longer relative to SEQ ID NO:1.

2. The mutated phosphotriesterase enzyme of claim 1, wherein the NCAA is p-fluorophenylalanine (pFF).

3. The mutated phosphotriesterase enzyme of claim 2, wherein the mutated PTE comprises the amino acid sequence depicted in SEQ ID NO: 3 in which the phenylalanine at position 104 is replaced by alanine and all the remaining phenylalanine residues are replaced by pFF, wherein the position 104 of phenylalanine is counted excluding the first ten amino acids of SEQ ID NO:3, said first ten amino acids comprising a polyhistidine tag.

4. A composition comprising the mutated phosphotriesterase enzyme of claim 1.

5. The composition of claim 4, wherein the composition is a prophylactic.

6. The composition of claim 5, wherein the prophylactic is a respiratory filter, inhaler, or topical cream.

7. The composition of claim 4, wherein the composition is selected from the group consisting of: a decontaminant, a water filtration system, a detergent, and feedstock.

8. The composition of claim 4, wherein the mutated phosphotriesterase enzyme comprises the amino acid sequence depicted in SEQ ID NO: 3 in which the phenylalanine at position 104 is replaced by alanine and all the remaining phenylalanine residues are replaced by pFF, wherein the position 104 of phenylalanine is counted excluding the first ten N-terminal amino acids of SEQ ID NO:3, said first ten N-terminal amino acids comprising a polyhistidine tag.

9. The mutated phosphotriesterase enzyme of claim 1, wherein the enzyme is effective against an organophosphate pesticide.

10. The mutated phosphotriesterase enzyme of claim 9, wherein the pesticide is chlorpyrifos.

11. The isolated mutated PTE of claim 1, wherein all occurrences except one of a specific amino acid residue are changed to an NCAA and the one unchanged occurrence of the specific amino acid residue is changed to a different natural amino acid.

12. The isolated mutated PTE of claim 11, wherein the specific amino acid residue is selected from the group consisting of phenylalanine, methionine, leucine, isoleucine, valine, proline, histidine, tyrosine and tryptophan.

13. An isolated mutated phosphotriesterase (PTE) having the sequence of SEQ ID NO:1 or a peptide having at least 85% homology with the sequence of SEQ ID NO:1, wherein all occurrences except one of a specific amino acid residue are changed to a non-canonical amino acid and the one unchanged amino acid of the specific amino acid residue is changed to a different natural amino acid, wherein the mutated PTE exhibits enhanced activity at elevated temperatures relative to the unmutated PTE, and/or maintains activity in solution at room temperature longer relative to the unmutated PTE.

14. The isolated mutated PTE of claim 13, wherein the specific amino acid residue is selected from the group consisting of phenylalanine, methionine, leucine, isoleucine, valine, proline, histidine, tyrosine and tryptophan.

* * * * *

SEQUENCE LISTING

<160> NUMBER OF SEQ ID NOS: 67

<210> SEQ ID NO 1
<211> LENGTH: 347
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 1

Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
50                  55                  60

Ala Val Arg Gly Leu Arg Arg Ala Arg Ala Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
        195                 200                 205

Cys Ile Gly His Ser Asp Asp Thr Asp Asp Leu Ser Tyr Leu Thr Ala
210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
                245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
        275                 280                 285

Ser Ser Tyr Val Thr Asn Ile Met Asp Val Met Asp Ser Val Asn Pro
290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
                325                 330                 335

Ala Arg Phe Leu Ser Pro Thr Leu Arg Ala Ser
            340                 345

<210> SEQ ID NO 2
<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atgagaggat cgcatcacca tcaccatcac ggatccatga tcaccaacag cggcgatcgg      60
atcaataccg tgcgcggtcc tatcacaatc tctgaagcgg gtttcacact gactcacgag     120
cacatctgcg gcagctcggc aggattcttg cgtgcttggc cagagttctt cggtagccgc     180
aaagctctag cggaaaaggc tgtgagagga ttgcgccgcg ccagagcggc tggcgtgcga     240
acgattgtcg atgtgtcgac tttcgatatc ggtcgcgatg tcagtttatt ggccgaggtt     300
tcgcgggctg ccgacgttca tatcgtggcg gcgaccggct tgtggttcga cccgccactt     360
tcgatgcgat tgaggagtgt agaggaactc acacagttct tcctgcgtga gattcaatat     420
ggcatcgaag acaccggaat tagggcgggc attatcaagg tcgcgaccac aggcaaggcg     480
accccctttc aggagttagt gttaaggcg gccgccgg ccagcttggc caccggtgtt        540
ccggtaacca ctcacacggc agcaagtcag cgcggtggtg agcagcaggc cgccattttt     600
gagtccgaag gcttgagccc ctcacgggtt tgtattggtc acagcgatga tactgacgat     660
ttgagctatc tcaccgccct cgctgcgcgc ggataccctca tcggtctaga ccacatcccg     720
cacagtgcga ttggtctaga agataatgcg agtgcatcag ccctcctggg catccgttcg     780
tggcaaacac gggctctctt gatcaaggcg ctcatcgacc aaggctacat gaaacaaatc     840
ctcgtttcga atgactggct gttcgggttt tcgagctatg tcaccaacat catggacgtg     900
atggatagcg tgaaccccga cgggatggcc ttcattccac tgagagtgat cccattccta     960
cgagagaagg gcgtcccaca ggaaacgctg gcaggcatca ctgtgactaa cccggcgcgg    1020
ttcttgtcac cgaccttgcg ggcgtcatga                                     1050
```

<210> SEQ ID NO 3
<211> LENGTH: 347
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
    50                  55                  60

Ala Val Arg Gly Leu Arg Ala Arg Ala Ala Gly Val Arg Thr Ile
65                  70                  75                  80

Val Asp Val Ser Thr Ala Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
    130                 135                 140

Ile Arg Ala Gly Ile Ile Lys Val Ala Thr Thr Gly Lys Ala Thr Pro
145                 150                 155                 160
```

Phe Gln Glu Leu Val Leu Arg Ala Ala Ala Arg Ala Ser Leu Ala Thr
            165                 170                 175

Gly Val Pro Val Thr Thr His Thr Ala Ala Ser Gln Arg Gly Gly Glu
        180                 185                 190

Gln Gln Ala Ala Ile Phe Glu Ser Glu Gly Leu Ser Pro Ser Arg Val
    195                 200                 205

Cys Ile Gly His Ser Asp Asp Thr Asp Asp Leu Ser Tyr Leu Thr Ala
210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
            245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
        275                 280                 285

Ser Ser Tyr Val Thr Asn Ile Met Asp Val Met Asp Ser Val Asn Pro
    290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
            325                 330                 335

Ala Arg Phe Leu Ser Pro Thr Leu Arg Ala Ser
            340                 345

<210> SEQ ID NO 4
<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgagaggat cgcatcacca tcaccatcac ggatccatga tcaccaacag cggcgatcgg      60
atcaataccg tgcgcggtcc tatcacaatc tctgaagcgg gtttcacact gactcacgag     120
cacatctgcg gcagctcggc aggattcttg cgtgcttggc cagagttctt cggtagccgc     180
aaagctctag cggaaaaggc tgtgagagga ttgcgccgcg ccagagcggc tggcgtgcga     240
acgattgtcg atgtgtcgac tgccgatatc ggtcgcgatg tcagtttatt ggccgaggtt     300
tcgcgggctg ccgacgttca tatcgtggcg gcgaccggct gtggttcga cccgccactt      360 tcgatgcgat tgaggagtgt agaggaactc acacagttct tcctgcgtga gattcaatat     420
ggcatcgaag acaccggaat tagggcgggc attatcaagg tcgcgaccac aggcaaggcg     480 acccccttc aggagttagt gttaagggcg gccgccgggg ccagcttggc caccggtgtt      540
ccggtaacca ctcacacggc agcaagtcag gcggtggtg agcagcaggc cgccattttt      600
gagtccgaag gcttgagccc ctcacgggtt tgtattggtc acagcgatga tactgacgat     660
ttgagctatc tcaccgccct cgctgcgcgc ggatacctca tcggtctaga ccacatcccg     720
cacagtgcga ttggtctaga agataatgcg agtgcatcag ccctcctggg catccgttcg     780
tggcaaacac gggctctctt gatcaaggcg ctcatcgacc aaggctacat gaaacaaatc     840
ctcgtttcga atgactggct gttcgggttt tcgagctatg tcaccaacat catggacgtg     900
atggatagcg tgaaccccga cgggatggcc ttcattccac tgagagtgat cccattccta     960

```
cgagagaagg gcgtcccaca ggaaacgctg gcaggcatca ctgtgactaa cccggcgcgg   1020
ttcttgtcac cgaccttgcg ggcgtcatga                                   1050
```

<210> SEQ ID NO 5
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Met Gly Asp Arg Ile Asn Thr Val Arg Gly Pro Ile Thr Ile Ser Glu
1               5                   10                  15

Ala Gly Phe Thr Leu Thr His Glu His Ile Cys Gly Ser Ser Ser Gly
            20                  25                  30

Phe Leu Arg Arg Trp Pro Glu Phe Phe Gly Ser Arg Lys Ala Leu Ala
        35                  40                  45

Glu Lys Ala Val Arg Gly Leu Arg Arg Ala Arg Ala Ala Gly Val Arg
    50                  55                  60

Thr Ile Val Asp Val Ala Thr Ala Ser Ile Gly Glu Asp Ala Ser Leu
65                  70                  75                  80

Leu Ala Glu Val Ser Arg Ala Ala Asp Val His Ile Val Ala Ala Thr
                85                  90                  95

Gly Ser Trp Phe Asp Ala Ser Leu Ser Leu Arg Leu Arg Ser Val Glu
            100                 105                 110

Glu Leu Thr Gln Phe Phe Leu Arg His Ile Gln Tyr Gly Ile Glu Asp
        115                 120                 125

Thr Gly Ile Arg Ala Gly Ile Ile Lys Val Ala Thr Thr Gly Lys Ala
    130                 135                 140

Thr Pro Phe Gln Glu Leu Val Leu Arg Ala Ala Arg Ala Ser Leu
145                 150                 155                 160

Ala Thr Gly Val Pro Val Thr Thr His Thr Ala Ala Ser Gln Arg Gly
                165                 170                 175

Gly Glu Gln Gln Ala Ala Ile Phe Glu Ser Glu Gly Leu Ser Pro Ser
            180                 185                 190

Arg Val Cys Ile Gly His Ser Asp Asp Thr Asp Asp Leu Ser Tyr Leu
        195                 200                 205

Thr Ala Leu Ala Ala Arg Gly Tyr Leu Ile Gly Leu Asp His Ile Pro
    210                 215                 220

His Ser Ala Ile Gly Leu Glu Asp Asn Ala Ser Ser Ala Leu Leu
225                 230                 235                 240

Gly Ile Arg Ser Trp Gln Thr Arg Ala Leu Leu Ile Lys Ala Leu Ile
                245                 250                 255

Asp Gln Gly Tyr Met Lys Gln Ile Leu Val Ser Asn Asp Trp Leu Phe
            260                 265                 270

Gly Phe Ser Ser Tyr Val Thr Asn Ile Met Asp Val Met Asp Ser Val
        275                 280                 285

Asn Pro Asp Gly Met Ala Phe Ile Pro Leu Arg Val Ile Pro Phe Leu
    290                 295                 300

Arg Glu Lys Gly Val Pro Gln Glu Thr Leu Ala Gly Ile Thr Val Thr
305                 310                 315                 320

Asn Pro Ala Arg Phe Leu Ser Pro Thr Leu Arg Ala Ser
                325                 330
```

<210> SEQ ID NO 6
<211> LENGTH: 347
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Leu Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
    50                  55                  60

Ala Val Arg Gly Leu Arg Arg Ala Arg Ala Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
    130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
        195                 200                 205

Cys Ile Gly His Ser Asp Asp Thr Asp Asp Leu Ser Tyr Leu Thr Ala
    210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
                245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
        275                 280                 285

Ser Ser Tyr Val Thr Asn Ile Met Asp Val Met Asp Ser Val Asn Pro
    290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
                325                 330                 335

Ala Arg Phe Leu Ser Pro Thr Leu Arg Ala Ser
            340                 345
```

<210> SEQ ID NO 7

```
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Arg Gly Ser His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
    50                  55                  60

Ala Val Arg Gly Leu Arg Arg Ala Arg Ala Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Met Leu Arg Glu Ile Gln Tyr Gly Ile Glu Asp Thr Gly
    130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
        195                 200                 205

Cys Ile Gly His Ser Asp Asp Thr Asp Asp Leu Ser Tyr Leu Thr Ala
    210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
                245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
        275                 280                 285

Ser Ser Tyr Val Thr Asn Ile Met Asp Val Met Asp Ser Val Asn Pro
    290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
                325                 330                 335

Ala Arg Phe Leu Ser Pro Thr Leu Arg Ala Ser
            340                 345

<210> SEQ ID NO 8
<211> LENGTH: 347
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 8

Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
    50                  55                  60

Ala Val Arg Gly Leu Arg Arg Ala Arg Ala Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Leu Glu Ser Glu Gly Leu Ser Pro Ser Arg Val
        195                 200                 205

Cys Ile Gly His Ser Asp Asp Thr Asp Asp Leu Ser Tyr Leu Thr Ala
210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
                245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
        275                 280                 285

Ser Ser Tyr Val Thr Asn Ile Met Asp Val Met Asp Ser Val Asn Pro
290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
                325                 330                 335

Ala Arg Phe Leu Ser Pro Thr Leu Arg Ala Ser
            340                 345

<210> SEQ ID NO 9
<211> LENGTH: 347
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 9

Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
    50                  55                  60

Ala Val Arg Gly Leu Arg Arg Ala Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
    130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
        195                 200                 205

Cys Ile Gly His Ser Asp Asp Thr Asp Leu Ser Tyr Leu Thr Ala
    210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
                245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Leu Gly Phe
        275                 280                 285

Ser Ser Tyr Val Thr Asn Ile Met Asp Val Met Asp Ser Val Asn Pro
    290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
                325                 330                 335

Ala Arg Phe Leu Ser Pro Thr Leu Arg Ala Ser
            340                 345

<210> SEQ ID NO 10
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
50                  55                  60

Ala Val Arg Gly Leu Arg Arg Ala Arg Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
        195                 200                 205

Cys Ile Gly His Ser Asp Asp Thr Asp Leu Ser Tyr Leu Thr Ala
210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
                245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Leu
        275                 280                 285

Ser Ser Tyr Val Thr Asn Ile Met Asp Val Met Asp Ser Val Asn Pro
290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
                325                 330                 335

Ala Arg Phe Leu Ser Pro Thr Leu Arg Ala Ser
            340                 345
```

<210> SEQ ID NO 11
<211> LENGTH: 347
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Met Arg Gly Ser His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
50                      55                  60

Ala Val Arg Gly Leu Arg Arg Ala Arg Ala Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Arg Ala Ser Leu Ala Thr
        165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
            195                 200                 205

Cys Ile Gly His Ser Asp Asp Thr Asp Leu Ser Tyr Leu Thr Ala
        210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
            245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
        275                 280                 285

Ser Ser Tyr Val Thr Asn Ile Met Asp Val Met Asp Ser Val Asn Pro
        290                 295                 300

Asp Gly Met Ala Leu Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
            325                 330                 335

Ala Arg Phe Leu Ser Pro Thr Leu Arg Ala Ser
            340                 345

<210> SEQ ID NO 12
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Arg Gly Ser His His His His His Met Ile Thr Asn Ser Gly
```

```
  1               5                  10                 15
Asp Arg Ile Asn Thr Val Arg Gly Pro Ile Thr Ile Ser Glu Ala Gly
                20                 25                 30

Phe Thr Leu Thr His Glu His Ile Cys Gly Ser Ser Ala Gly Phe Leu
                35                 40                 45

Arg Ala Trp Pro Glu Phe Phe Gly Ser Arg Lys Ala Leu Ala Glu Lys
                50                 55                 60

Ala Val Arg Gly Leu Arg Arg Ala Arg Ala Gly Val Arg Thr Ile
 65                 70                 75                 80

Val Asp Val Ser Thr Phe Asp Ile Gly Arg Asp Val Ser Leu Leu Ala
                85                 90                 95

Glu Val Ser Arg Ala Ala Asp Val His Ile Val Ala Ala Thr Gly Leu
               100                105                110

Trp Phe Asp Pro Pro Leu Ser Met Arg Leu Arg Ser Val Glu Glu Leu
               115                120                125

Thr Gln Phe Phe Leu Arg Glu Ile Gln Tyr Gly Ile Glu Asp Thr Gly
               130                135                140

Ile Arg Ala Gly Ile Ile Lys Val Ala Thr Thr Gly Lys Ala Thr Pro
145                150                155                160

Phe Gln Glu Leu Val Leu Arg Ala Ala Arg Ala Ser Leu Ala Thr
               165                170                175

Gly Val Pro Val Thr Thr His Thr Ala Ala Ser Gln Arg Gly Gly Glu
               180                185                190

Gln Gln Ala Ala Ile Phe Glu Ser Glu Gly Leu Ser Pro Ser Arg Val
               195                200                205

Cys Ile Gly His Ser Asp Asp Thr Asp Leu Ser Tyr Leu Thr Ala
               210                215                220

Leu Ala Ala Arg Gly Tyr Leu Ile Gly Leu Asp His Ile Pro His Ser
225                230                235                240

Ala Ile Gly Leu Glu Asp Asn Ala Ser Ala Ala Leu Leu Gly Ile
               245                250                255

Arg Ser Trp Gln Thr Arg Ala Leu Leu Ile Lys Ala Leu Ile Asp Gln
               260                265                270

Gly Tyr Met Lys Gln Ile Leu Val Ser Asn Asp Trp Leu Phe Gly Phe
               275                280                285

Ser Ser Tyr Val Thr Asn Ile Met Asp Val Met Asp Ser Val Asn Pro
               290                295                300

Asp Gly Met Ala Phe Ile Pro Leu Arg Val Ile Pro Met Leu Arg Glu
305                310                315                320

Lys Gly Val Pro Gln Glu Thr Leu Ala Gly Ile Thr Val Thr Asn Pro
               325                330                335

Ala Arg Phe Leu Ser Pro Thr Leu Arg Ala Ser
               340                345
```

<210> SEQ ID NO 13
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Arg Gly Ser His His His His His His Met Ile Thr Asn Ser Gly
1               5                  10                 15
```

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
    50                  55                  60

Ala Val Arg Gly Leu Arg Ala Arg Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
    130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
        195                 200                 205

Cys Ile Gly His Ser Asp Asp Thr Asp Leu Ser Tyr Leu Thr Ala
    210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
                245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
        275                 280                 285

Ser Ser Tyr Val Thr Asn Ile Met Asp Val Met Asp Ser Val Asn Pro
    290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
                325                 330                 335

Ala Arg Leu Leu Ser Pro Thr Leu Arg Ala Ser
            340                 345

<210> SEQ ID NO 14
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

```
Arg Ala Trp Pro Glu Phe Phe Gly Ser Arg Lys Ala Leu Ala Glu Lys
            35                  40                  45

Ala Val Arg Gly Leu Arg Arg Ala Arg Ala Ala Gly Val Arg Thr Ile
 50                  55                  60

Val Asp Val Ser Thr Phe Asp Gly Gly Arg Asp Val Ser Leu Leu Ala
 65                  70                  75                  80

Glu Val Ser Arg Ala Ala Asp Val His Ile Val Ala Ala Thr Gly Leu
                 85                  90                  95

Ser Trp Asp Pro Pro Leu Ser Met Arg Leu Arg Ser Val Glu Glu Leu
                100                 105                 110

Thr Gln Phe Phe Leu Arg Glu Ile Gln Tyr Gly Ile Glu Asp Thr Gly
            115                 120                 125

Ile Arg Ala Gly Ile Ile Leu Val Ala Thr Thr Gly Lys Ala Thr Pro
        130                 135                 140

Phe Gln Glu Leu Val Leu Arg Ala Ala Arg Ala Ser Leu Ala Thr
145                 150                 155                 160

Gly Val Pro Val Thr Thr His Thr Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Ser Thr Asp Leu Ser Tyr Leu Thr Ala
            195                 200                 205

Leu Ala Ala Arg Gly Tyr Leu Ile Gly Leu Asp Gly Ile Pro Leu Ser
210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Gly Phe Gly Asp
                260                 265                 270

Ser Gly Gly Val Thr Asn Ile Met Asp Val Arg Asp Ser Val Asn Pro
            275                 280                 285

Asp Gly Met Ala Phe Ile Pro Leu Arg Val Ile Pro Phe Leu Arg Glu
        290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 15
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
            35                  40                  45

Ala Val Arg Gly Leu Arg Arg Ala Arg Ala Ala Gly Val Arg Thr Ile
 50                  55                  60
```

```
            50                  55                  60
Val Asp Val Ser Thr Phe Asp Ser Gly Arg Asp Val Ser Leu Leu Ala
 65                  70                  75                  80

Glu Val Ser Arg Ala Ala Asp Val His Ile Val Ala Ala Thr Gly Leu
                 85                  90                  95

Ser Trp Asp Pro Pro Leu Ser Met Arg Leu Arg Ser Val Glu Glu Leu
                100                 105                 110

Thr Gln Phe Phe Leu Arg Glu Ile Gln Tyr Gly Ile Glu Asp Thr Gly
            115                 120                 125

Ile Arg Ala Gly Ile Ile Leu Val Ala Thr Thr Gly Lys Ala Thr Pro
        130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asn Thr Asp Leu Ser Tyr Leu Thr Ala
        195                 200                 205

Leu Ala Ala Arg Gly Tyr Leu Ile Gly Leu Asp Gly Ile Pro Phe Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Ala Phe Gly Met
            260                 265                 270

Ser Ala Gly Val Thr Asn Ile Met Asp Val Leu Asp Ser Val Asn Pro
        275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 16
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Arg Ile Asn Thr Val Arg Gly Pro Ile Thr Ile Ser Glu Ala Gly
 1               5                  10                  15

Phe Thr Leu Thr His Glu His Ile Cys Val Ser Ser Ala Gly Phe Leu
                20                  25                  30

Arg Ala Trp Pro Glu Phe Phe Gly Ser Arg Lys Ala Leu Ala Glu Lys
            35                  40                  45

Ala Val Arg Gly Leu Arg Arg Ala Arg Ala Ala Gly Val Arg Thr Ile
        50                  55                  60

Val Asp Val Ser Thr Phe Asp Leu Gly Arg Asp Val Ser Leu Leu Ala
 65                  70                  75                  80
```

```
Glu Val Ser Arg Ala Ala Asp Val His Ile Val Ala Ala Thr Gly Leu
                85                  90                  95

Gly Phe Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp His Ile Pro His Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Cys Phe Gly Asn
            260                 265                 270

Ser Leu Gly Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 17
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
                20                  25                  30

Arg Ala Trp Pro Glu Phe Phe Gly Ser Arg Lys Ala Leu Ala Glu Lys
            35                  40                  45

Ala Val Arg Gly Leu Arg Arg Ala Arg Ala Ala Gly Val Arg Thr Ile
    50                  55                  60

Val Asp Val Ser Thr Phe Asp Thr Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Met Asp Pro Pro Leu Ser Met Arg Leu Arg Ser Val Glu Glu Leu
            100                 105                 110
```

Thr Gln Phe Phe Leu Arg Glu Ile Gln Tyr Gly Ile Glu Asp Thr Gly
            115                 120                 125

Ile Arg Ala Gly Ile Ile Leu Val Ala Thr Thr Gly Lys Ala Thr Pro
        130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Glu Thr Asp Asp Leu Ser Tyr Leu Thr Ala
        195                 200                 205

Leu Ala Ala Arg Gly Tyr Leu Ile Gly Leu Asp Asn Ile Pro Ala Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Ala Phe Gly Ile
            260                 265                 270

Ser Phe Gly Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 18
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Leu Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Leu Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

```
            130                 135                 140
Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Leu Ser Tyr Leu Thr Ala
            195                 200                 205

Leu Ala Ala Arg Gly Tyr Leu Ile Gly Leu Asp Ala Ile Pro His Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Cys Phe Gly Leu
            260                 265                 270

Ser Ala Gly Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 19
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Arg Ile Asn Thr Val Arg Gly Pro Ile Thr Ile Ser Glu Ala Gly
1               5                   10                  15

Phe Thr Leu Thr His Glu His Ile Cys Gly Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Gln Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Phe Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160
```

Gly Val Pro Val Thr Thr His Thr Ala Ala Ser Gln Arg Gly Gly Glu
            165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Leu Ser Tyr Leu Thr Ala
            195                 200                 205

Leu Ala Ala Arg Gly Tyr Leu Ile Gly Leu Asp His Ile Pro His Ser
210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
            245                 250                 255

Gly Tyr Met Lys Gln Ile Leu Val Ser Asn Asp Tyr Gly Phe Gly Leu
            260                 265                 270

Ser Ala Gly Val Thr Asn Ile Met Asp Val His Asp Ser Val Asn Pro
            275                 280                 285

Asp Gly Met Ala Phe Ile Pro Leu Arg Val Ile Pro Phe Leu Arg Glu
            290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
            325                 330

<210> SEQ ID NO 20
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Arg Ile Asn Thr Val Arg Gly Pro Ile Thr Ile Ser Glu Ala Gly
1               5                   10                  15

Phe Thr Leu Thr His Glu His Ile Cys Met Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Thr Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Trp Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

```
Cys Ile Gly His Ser Asp Asp Thr Asp Asp Leu Ser Tyr Leu Thr Ala
            195                 200                 205

Leu Ala Ala Arg Gly Tyr Leu Ile Gly Leu Asp His Ile Pro His Ser
        210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Ser Phe Gly Asn
            260                 265                 270

Ser Leu Gly Val Thr Asn Ile Met Asp Val Glu Asp Ser Val Asn Pro
        275                 280                 285

Asp Gly Met Ala Phe Ile Pro Leu Arg Val Ile Pro Phe Leu Arg Glu
290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 21
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
50                  55                  60

Val Asp Val Ser Thr Phe Asp Gln Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Phe Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
130                 135                 140

Phe Gln Glu Leu Val Leu Arg Ala Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
            195                 200                 205

Leu Ala Ala Arg Gly Tyr Leu Ile Gly Leu Asp His Ile Pro His Ser
```

```
                210                 215                 220
Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Gly Phe Gly Met
                260                 265                 270

Ser Ala Gly Val Thr Asn Ile Met Asp Val Ile Asp Ser Val Asn Pro
                275                 280                 285

Asp Gly Met Ala Phe Ile Pro Leu Arg Val Ile Pro Phe Leu Arg Glu
                290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 22
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Arg Ile Asn Thr Val Arg Gly Pro Ile Thr Ile Ser Glu Ala Gly
1               5                   10                  15

Phe Thr Leu Thr His Glu His Ile Cys Ala Ser Ser Ala Gly Phe Leu
                20                  25                  30

Arg Ala Trp Pro Glu Phe Phe Gly Ser Arg Lys Ala Leu Ala Glu Lys
            35                  40                  45

Ala Val Arg Gly Leu Arg Arg Ala Arg Ala Ala Gly Val Arg Thr Ile
        50                  55                  60

Val Asp Val Ser Thr Phe Asp Ser Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Trp Asp Pro Pro Leu Ser Met Arg Leu Arg Ser Val Glu Glu Leu
                100                 105                 110

Thr Gln Phe Phe Leu Arg Glu Ile Gln Tyr Gly Ile Glu Asp Thr Gly
            115                 120                 125

Ile Arg Ala Gly Ile Ile Leu Val Ala Thr Thr Gly Lys Ala Thr Pro
        130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
                180                 185                 190

Cys Ile Gly His Ser Asp Asp Thr Asp Asp Leu Ser Tyr Leu Thr Ala
            195                 200                 205

Leu Ala Ala Arg Gly Tyr Leu Ile Gly Leu Asp His Ile Pro His Ser
        210                 215                 220

Ala Ile Gly Leu Glu Asp Asn Ala Ser Ala Ser Ala Trp Leu Gly Ile
225                 230                 235                 240
```

```
Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Ser Phe Gly Val
            260                 265                 270

Ser Ile Gly Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 23
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Ser Gly Arg Asp Val Ser Leu Leu Ala
65                  70                  75                  80

Glu Val Ser Arg Ala Ala Asp Val His Ile Val Ala Ala Thr Gly Leu
                85                  90                  95

Trp Ala Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp His Ile Pro His Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Trp Ala Phe Gly Gly
            260                 265                 270
```

```
Ser Asn Tyr Val Thr Asn Ile Met Asp Val Trp Asp Ser Val Asn Pro
        275                 280                 285

Asp Gly Met Ala Phe Ile Pro Leu Arg Val Ile Pro Phe Leu Arg Glu
        290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330
```

<210> SEQ ID NO 24
<211> LENGTH: 331
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Asp Arg Ile Asn Thr Val Arg Gly Pro Ile Thr Ile Ser Glu Ala Gly
1               5                   10                  15

Phe Thr Leu Thr His Glu His Ile Cys Met Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Gln Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Trp Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Ser Thr Asp Leu Ser Tyr Leu Thr Ala
        195                 200                 205

Leu Ala Ala Arg Gly Tyr Leu Ile Gly Leu Asp Ser Ile Pro Trp Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Trp Gly Phe Gly Ala
            260                 265                 270

Ser Ala Gly Val Thr Asn Ile Met Asp Val Tyr Asp Ser Val Asn Pro
        275                 280                 285

Asp Gly Met Ala Phe Ile Pro Leu Arg Val Ile Pro Phe Leu Arg Glu
```

```
                 290                 295                 300
Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 25
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Arg Ile Asn Thr Val Arg Gly Pro Ile Thr Ile Ser Glu Ala Gly
1               5                   10                  15

Phe Thr Leu Thr His Glu His Ile Cys Cys Ser Ser Ala Gly Phe Leu
                20                  25                  30

Arg Ala Trp Pro Glu Phe Phe Gly Ser Arg Lys Ala Leu Ala Glu Lys
            35                  40                  45

Ala Val Arg Gly Leu Arg Arg Ala Arg Ala Ala Gly Val Arg Thr Ile
50                  55                  60

Val Asp Val Ser Thr Phe Asp Gln Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Asn Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp Cys Ile Pro Trp Ser
210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Gly Phe Gly Ala
            260                 265                 270

Ser Ala Gly Val Thr Asn Ile Met Asp Val Leu Asp Ser Val Asn Pro
        275                 280                 285

Asp Gly Met Ala Phe Ile Pro Leu Arg Val Ile Pro Phe Leu Arg Glu
290                 295                 300

Lys Gly Val Pro Gln Glu Thr Leu Ala Gly Ile Thr Val Thr Asn Pro
305                 310                 315                 320
```

```
Ala Arg Phe Leu Ser Pro Thr Leu Arg Ala Ser
            325                 330
```

<210> SEQ ID NO 26
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Gly Val Arg Thr Ile
    50                  55                  60

Val Asp Val Ser Thr Phe Asp Ala Gly Arg Asp Val Ser Leu Leu Ala
65                  70                  75                  80

Glu Val Ser Arg Ala Ala Asp Val His Ile Val Ala Thr Gly Leu
                85                  90                  95

Trp Ala Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp His Ile Pro Phe Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Trp His Phe Gly Gly
            260                 265                 270

Ser Gly Tyr Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
            325                 330
```

<210> SEQ ID NO 27

<211> LENGTH: 331
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

Asp Arg Ile Asn Thr Val Arg Gly Pro Ile Thr Ile Ser Glu Ala Gly
1               5                   10                  15

Phe Thr Leu Thr His Glu His Ile Cys Gly Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Gln Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Leu Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp Gln Ile Pro Phe Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Ala Phe Gly Leu
            260                 265                 270

Ser Ala Gly Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 28
<211> LENGTH: 331
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 28

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Ala Gly Val Arg Thr Ile
    50                  55                  60

Val Asp Val Ser Thr Phe Asp Gln Gly Arg Asp Val Ser Leu Leu Ala
65                  70                  75                  80

Glu Val Ser Arg Ala Ala Asp Val His Ile Val Ala Ala Thr Gly Leu
            85                  90                  95

Gly Pro Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
            165                 170                 175

Gln Gln Ala Ala Ile Phe Glu Ser Glu Gly Leu Ser Pro Ser Arg Val
        180                 185                 190

Cys Ile Gly His Ser Asp Asn Thr Asp Asp Leu Ser Tyr Leu Thr Ala
        195                 200                 205

Leu Ala Ala Arg Gly Tyr Leu Ile Gly Leu Asp Ala Ile Pro His Ser
210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
            245                 250                 255

Gly Tyr Met Lys Gln Ile Leu Val Ser Asn Asp Tyr Ala Phe Gly Leu
        260                 265                 270

Ser Asn Gly Val Thr Asn Ile Met Asp Val His Asp Ser Val Asn Pro
    275                 280                 285

Asp Gly Met Ala Phe Ile Pro Leu Arg Val Ile Pro Phe Leu Arg Glu
290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
            325                 330

<210> SEQ ID NO 29
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Arg Ile Asn Thr Val Arg Gly Pro Ile Thr Ile Ser Glu Ala Gly

```
            1               5                  10                 15
        Phe Thr Leu Thr His Glu His Ile Cys Gly Ser Ser Ala Gly Phe Leu
                        20                 25                 30

Arg Ala Trp Pro Glu Phe Phe Gly Ser Arg Lys Ala Leu Ala Glu Lys
                        35                 40                 45

Ala Val Arg Gly Leu Arg Arg Ala Ala Gly Val Arg Thr Ile
                        50                 55                 60

Val Asp Val Ser Thr Phe Asp Gly Gly Arg Asp Val Ser Leu Leu Ala
        65                      70                 75                 80

Glu Val Ser Arg Ala Ala Asp Val His Ile Val Ala Ala Thr Gly Leu
                        85                 90                 95

Ser Trp Asp Pro Pro Leu Ser Met Arg Leu Arg Ser Val Glu Glu Leu
                        100                105                110

Thr Gln Phe Phe Leu Arg Glu Ile Gln Tyr Gly Ile Glu Asp Thr Gly
                        115                120                125

Ile Arg Ala Gly Ile Ile Leu Val Ala Thr Thr Gly Lys Ala Thr Pro
                        130                135                140

Phe Gln Glu Leu Val Leu Arg Ala Ala Arg Ala Ser Leu Ala Thr
        145                     150                155                160

Gly Val Pro Val Thr Thr His Thr Ala Ala Ser Gln Arg Gly Gly Glu
                        165                170                175

Gln Gln Ala Ala Ile Phe Glu Ser Glu Gly Leu Ser Pro Ser Arg Val
                        180                185                190

Cys Ile Gly His Ser Asp Asp Thr Asp Leu Ser Tyr Leu Thr Ala
                        195                200                205

Leu Ala Ala Arg Gly Tyr Leu Ile Gly Leu Asp Ser Ile Pro Lys Ser
                        210                215                220

Ala Ile Gly Leu Glu Asp Asn Ala Ser Ala Ser Ala Trp Leu Gly Ile
        225                     230                235                240

Arg Ser Trp Gln Thr Arg Ala Leu Leu Ile Lys Ala Leu Ile Asp Gln
                        245                250                255

Gly Tyr Met Lys Gln Ile Leu Val Ser Asn Asp Tyr Ala Phe Gly Leu
                        260                265                270

Ser Ala Gly Val Thr Asn Ile Met Asp Val His Asp Ser Val Asn Pro
                        275                280                285

Asp Gly Met Ala Phe Ile Pro Leu Arg Val Ile Pro Phe Leu Arg Glu
                        290                295                300

Lys Gly Val Pro Gln Glu Thr Leu Ala Gly Ile Thr Val Thr Asn Pro
        305                     310                315                320

Ala Arg Phe Leu Ser Pro Thr Leu Arg Ala Ser
                        325                330

<210> SEQ ID NO 30
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Arg Ile Asn Thr Val Arg Gly Pro Ile Thr Ile Ser Glu Ala Gly
1               5                   10                  15

Phe Thr Leu Thr His Glu His Ile Cys Ala Ser Ser Ala Gly Phe Leu
                20                  25                  30
```

```
Arg Ala Trp Pro Glu Phe Phe Gly Ser Arg Lys Ala Leu Ala Glu Lys
             35                  40                  45

Ala Val Arg Gly Leu Arg Arg Ala Arg Ala Ala Gly Val Arg Thr Ile
 50                  55                  60

Val Asp Val Ser Thr Phe Asp Gln Gly Arg Asp Val Ser Leu Leu Ala
 65                  70                  75                  80

Glu Val Ser Arg Ala Ala Asp Val His Ile Val Ala Ala Thr Gly Leu
                 85                  90                  95

Gly Trp Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
            115                 120                 125

Ile Arg Ala Gly Ile Ile Leu Val Ala Thr Thr Gly Lys Ala Thr Pro
        130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp Gln Ile Pro His Ser
        210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Pro Phe Gly Val
            260                 265                 270

Ser Ala Gly Val Thr Asn Ile Met Asp Val Val Asp Ser Val Asn Pro
        275                 280                 285

Asp Gly Met Ala Phe Ile Pro Leu Arg Val Ile Pro Phe Leu Arg Glu
        290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 31
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Arg Ile Asn Thr Val Arg Gly Pro Ile Thr Ile Ser Glu Ala Gly
1               5                   10                  15

Phe Thr Leu Thr His Glu His Ile Cys Ala Ser Ser Ala Gly Phe Leu
                20                  25                  30

Arg Ala Trp Pro Glu Phe Phe Gly Ser Arg Lys Ala Leu Ala Glu Lys
            35                  40                  45

Ala Val Arg Gly Leu Arg Arg Ala Arg Ala Ala Gly Val Arg Thr Ile
 50                  55                  60
```

Val Asp Val Ser Thr Phe Asp Gly Arg Asp Val Ser Leu Leu Ala
65                  70                  75                  80

Glu Val Ser Arg Ala Ala Asp Val His Ile Val Ala Ala Thr Gly Leu
            85                  90                  95

Gly Pro Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
            115                 120                 125

Ile Arg Ala Gly Ile Ile Leu Val Ala Thr Thr Gly Lys Ala Thr Pro
130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
            165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
            195                 200                 205

Leu Ala Ala Arg Gly Tyr Leu Ile Gly Leu Asp Asn Ile Pro Phe Ser
210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
            245                 250                 255

Gly Tyr Met Lys Gln Ile Leu Val Ser Asn Asp Tyr Pro Phe Gly Leu
            260                 265                 270

Ser Ala Gly Val Thr Asn Ile Met Asp Val Val Asp Ser Val Asn Pro
            275                 280                 285

Asp Gly Met Ala Phe Ile Pro Leu Arg Val Ile Pro Phe Leu Arg Glu
            290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
            325                 330

<210> SEQ ID NO 32
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Arg Ile Asn Thr Val Arg Gly Pro Ile Thr Ile Ser Glu Ala Gly
1               5                   10                  15

Phe Thr Leu Thr His Glu His Ile Cys Gly Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Met Gly Arg Asp Val Ser Leu Leu Ala
65                  70                  75                  80

Glu Val Ser Arg Ala Ala Asp Val His Ile Val Ala Ala Thr Gly Leu
            85                  90                  95

```
                     85                  90                  95
Trp Ile Asp Pro Pro Leu Ser Met Arg Leu Arg Ser Val Glu Glu Leu
                100                 105                 110

Thr Gln Phe Phe Leu Arg Glu Ile Gln Tyr Gly Ile Glu Asp Thr Gly
            115                 120                 125

Ile Arg Ala Gly Ile Ile Leu Val Ala Thr Thr Gly Lys Ala Thr Pro
        130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp His Ile Pro Phe Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Trp Ala Phe Gly Leu
            260                 265                 270

Ser Ala Tyr Val Thr Asn Ile Met Asp Val Leu Asp Ser Val Asn Pro
        275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 33
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Arg Ile Asn Thr Val Arg Gly Pro Ile Thr Ile Ser Glu Ala Gly
1               5                   10                  15

Phe Thr Leu Thr His Glu His Ile Cys Phe Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Met Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Trp Asp Pro Pro Leu Ser Met Arg Leu Arg Ser Val Glu Glu Leu
            100                 105                 110
```

```
Thr Gln Phe Phe Leu Arg Glu Ile Gln Tyr Gly Ile Glu Asp Thr Gly
            115                 120                 125
Ile Arg Ala Gly Ile Ile Leu Val Ala Thr Thr Gly Lys Ala Thr Pro
    130                 135                 140
Phe Gln Glu Leu Val Leu Arg Ala Ala Arg Ala Ser Leu Ala Thr
145                 150                 155                 160
Gly Val Pro Val Thr Thr His Thr Ala Ala Ser Gln Arg Gly Gly Glu
                165                 170                 175
Gln Gln Ala Ala Ile Phe Glu Ser Gly Leu Ser Pro Ser Arg Val
            180                 185                 190
Cys Ile Gly His Ser Asp Asp Thr Asp Leu Ser Tyr Leu Thr Ala
            195                 200                 205
Leu Ala Ala Arg Gly Tyr Leu Ile Gly Leu Asp Ala Ile Pro His Ser
    210                 215                 220
Ala Ile Gly Leu Glu Asp Asn Ala Ser Ala Ser Ala Trp Leu Gly Ile
225                 230                 235                 240
Arg Ser Trp Gln Thr Arg Ala Leu Leu Ile Lys Ala Leu Ile Asp Gln
                245                 250                 255
Gly Tyr Met Lys Gln Ile Leu Val Ser Asn Asp Tyr Ser Phe Gly Met
            260                 265                 270
Ser Ala Gly Val Thr Asn Ile Met Asp Val His Asp Ser Val Asn Pro
    275                 280                 285
Asp Gly Met Ala Phe Ile Pro Leu Arg Val Ile Pro Phe Leu Arg Glu
            290                 295                 300
Lys Gly Val Pro Gln Glu Thr Leu Ala Gly Ile Thr Val Thr Asn Pro
305                 310                 315                 320
Ala Arg Phe Leu Ser Pro Thr Leu Arg Ala Ser
                325                 330

<210> SEQ ID NO 34
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Para-fluoro Phe
<220> FEATURE:
<221> NAME/KEY: MOD_RES
<222> LOCATION: (47)..(47)
<223> OTHER INFORMATION: Para-fluoro Phe
<220> FEATURE:
<221> NAME/KEY: MOD_RES
<222> LOCATION: (54)..(55)
<223> OTHER INFORMATION: Para-fluoro Phe
<220> FEATURE:
<221> NAME/KEY: MOD_RES
<222> LOCATION: (86)..(86)
<223> OTHER INFORMATION: Para-fluoro Phe
<220> FEATURE:
<221> NAME/KEY: MOD_RES
<222> LOCATION: (114)..(114)
<223> OTHER INFORMATION: Para-fluoro Phe
<220> FEATURE:
<221> NAME/KEY: MOD_RES
<222> LOCATION: (131)..(132)
<223> OTHER INFORMATION: Para-fluoro Phe
<220> FEATURE:
<221> NAME/KEY: MOD_RES
<222> LOCATION: (161)..(161)
<223> OTHER INFORMATION: Para-fluoro Phe
<220> FEATURE:
```

```
<221> NAME/KEY: MOD_RES
<222> LOCATION: (198)..(198)
<223> OTHER INFORMATION: Para-fluoro Phe
<220> FEATURE:
<221> NAME/KEY: MOD_RES
<222> LOCATION: (286)..(286)
<223> OTHER INFORMATION: Para-fluoro Phe
<220> FEATURE:
<221> NAME/KEY: MOD_RES
<222> LOCATION: (288)..(288)
<223> OTHER INFORMATION: Para-fluoro Phe
<220> FEATURE:
<221> NAME/KEY: MOD_RES
<222> LOCATION: (309)..(309)
<223> OTHER INFORMATION: Para-fluoro Phe
<220> FEATURE:
<221> NAME/KEY: MOD_RES
<222> LOCATION: (317)..(317)
<223> OTHER INFORMATION: Para-fluoro Phe
<220> FEATURE:
<221> NAME/KEY: MOD_RES
<222> LOCATION: (339)..(339)
<223> OTHER INFORMATION: Para-fluoro Phe

<400> SEQUENCE: 34

Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
50                  55                  60

Ala Val Arg Gly Leu Arg Arg Ala Arg Ala Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
        195                 200                 205

Cys Ile Gly His Ser Asp Asp Thr Asp Leu Ser Tyr Leu Thr Ala
210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Leu Leu Gly Ile
                245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
        275                 280                 285
```

```
Ser Ser Tyr Val Thr Asn Ile Met Asp Val Met Asp Ser Val Asn Pro
    290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
                325                 330                 335

Ala Arg Phe Leu Ser Pro Thr Leu Arg Ala Ser
            340                 345

<210> SEQ ID NO 35
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Para-fluoro Phe
<220> FEATURE:
<221> NAME/KEY: MOD_RES
<222> LOCATION: (47)..(47)
<223> OTHER INFORMATION: Para-fluoro Phe
<220> FEATURE:
<221> NAME/KEY: MOD_RES
<222> LOCATION: (54)..(55)
<223> OTHER INFORMATION: Para-fluoro Phe
<220> FEATURE:
<221> NAME/KEY: MOD_RES
<222> LOCATION: (114)..(114)
<223> OTHER INFORMATION: Para-fluoro Phe
<220> FEATURE:
<221> NAME/KEY: MOD_RES
<222> LOCATION: (131)..(132)
<223> OTHER INFORMATION: Para-fluoro Phe
<220> FEATURE:
<221> NAME/KEY: MOD_RES
<222> LOCATION: (161)..(161)
<223> OTHER INFORMATION: Para-fluoro Phe
<220> FEATURE:
<221> NAME/KEY: MOD_RES
<222> LOCATION: (198)..(198)
<223> OTHER INFORMATION: Para-fluoro Phe
<220> FEATURE:
<221> NAME/KEY: MOD_RES
<222> LOCATION: (286)..(286)
<223> OTHER INFORMATION: Para-fluoro Phe
<220> FEATURE:
<221> NAME/KEY: MOD_RES
<222> LOCATION: (288)..(288)
<223> OTHER INFORMATION: Para-fluoro Phe
<220> FEATURE:
<221> NAME/KEY: MOD_RES
<222> LOCATION: (309)..(309)
<223> OTHER INFORMATION: Para-fluoro Phe
<220> FEATURE:
<221> NAME/KEY: MOD_RES
<222> LOCATION: (317)..(317)
<223> OTHER INFORMATION: Para-fluoro Phe
<220> FEATURE:
<221> NAME/KEY: MOD_RES
<222> LOCATION: (339)..(339)
<223> OTHER INFORMATION: Para-fluoro Phe

<400> SEQUENCE: 35

Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
```

```
            35                  40                  45
Arg Ala Trp Pro Glu Phe Phe Gly Ser Arg Lys Ala Leu Ala Glu Lys
 50                  55                  60

Ala Val Arg Gly Leu Arg Arg Ala Ala Gly Val Arg Thr Ile
 65                  70                  75                  80

Val Asp Val Ser Thr Ala Asp Ile Gly Arg Asp Val Ser Leu Leu Ala
                 85                  90                  95

Glu Val Ser Arg Ala Ala Asp Val His Ile Val Ala Thr Gly Leu
            100                 105                 110

Trp Phe Asp Pro Pro Leu Ser Met Arg Leu Arg Ser Val Glu Glu Leu
            115                 120                 125

Thr Gln Phe Phe Leu Arg Glu Ile Gln Tyr Gly Ile Glu Asp Thr Gly
130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
            195                 200                 205

Cys Ile Gly His Ser Asp Asp Thr Asp Leu Ser Tyr Leu Thr Ala
210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
                245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
            275                 280                 285

Ser Ser Tyr Val Thr Asn Ile Met Asp Val Met Asp Ser Val Asn Pro
290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
                325                 330                 335

Ala Arg Phe Leu Ser Pro Thr Leu Arg Ala Ser
            340                 345

<210> SEQ ID NO 36
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(19)
<223> OTHER INFORMATION: Para-fluoro Phe
<220> FEATURE:
<221> NAME/KEY: MOD_RES
<222> LOCATION: (33)..(33)
<223> OTHER INFORMATION: Para-fluoro Phe
<220> FEATURE:
<221> NAME/KEY: MOD_RES
<222> LOCATION: (40)..(41)
<223> OTHER INFORMATION: Para-fluoro Phe
```

```
<220> FEATURE:
<221> NAME/KEY: MOD_RES
<222> LOCATION: (100)..(100)
<223> OTHER INFORMATION: Para-fluoro Phe
<220> FEATURE:
<221> NAME/KEY: MOD_RES
<222> LOCATION: (117)..(118)
<223> OTHER INFORMATION: Para-fluoro Phe
<220> FEATURE:
<221> NAME/KEY: MOD_RES
<222> LOCATION: (147)..(147)
<223> OTHER INFORMATION: Para-fluoro Phe
<220> FEATURE:
<221> NAME/KEY: MOD_RES
<222> LOCATION: (184)..(184)
<223> OTHER INFORMATION: Para-fluoro Phe
<220> FEATURE:
<221> NAME/KEY: MOD_RES
<222> LOCATION: (272)..(272)
<223> OTHER INFORMATION: Para-fluoro Phe
<220> FEATURE:
<221> NAME/KEY: MOD_RES
<222> LOCATION: (274)..(274)
<223> OTHER INFORMATION: Para-fluoro Phe
<220> FEATURE:
<221> NAME/KEY: MOD_RES
<222> LOCATION: (295)..(295)
<223> OTHER INFORMATION: Para-fluoro Phe
<220> FEATURE:
<221> NAME/KEY: MOD_RES
<222> LOCATION: (303)..(303)
<223> OTHER INFORMATION: Para-fluoro Phe
<220> FEATURE:
<221> NAME/KEY: MOD_RES
<222> LOCATION: (325)..(325)
<223> OTHER INFORMATION: Para-fluoro Phe

<400> SEQUENCE: 36

Met Gly Asp Arg Ile Asn Thr Val Arg Gly Pro Ile Thr Ile Ser Glu
1               5                   10                  15

Ala Gly Phe Thr Leu Thr His Glu His Ile Cys Gly Ser Ser Ser Gly
            20                  25                  30

Phe Leu Arg Arg Trp Pro Glu Phe Phe Gly Ser Arg Lys Ala Leu Ala
        35                  40                  45

Glu Lys Ala Val Arg Gly Leu Arg Arg Ala Arg Ala Ala Gly Val Arg
50                  55                  60

Thr Ile Val Asp Val Ala Thr Ala Ser Ile Gly Glu Asp Ala Ser Leu
65                  70                  75                  80

Leu Ala Glu Val Ser Arg Ala Ala Asp Val His Ile Val Ala Ala Thr
                85                  90                  95

Gly Ser Trp Phe Asp Ala Ser Leu Ser Leu Arg Leu Arg Ser Val Glu
            100                 105                 110

Glu Leu Thr Gln Phe Phe Leu Arg His Ile Gln Tyr Gly Ile Glu Asp
        115                 120                 125

Thr Gly Ile Arg Ala Gly Ile Ile Lys Val Ala Thr Thr Gly Lys Ala
130                 135                 140

Thr Pro Phe Gln Glu Leu Val Leu Arg Ala Ala Arg Ala Ser Leu
145                 150                 155                 160

Ala Thr Gly Val Pro Val Thr Thr His Thr Ala Ala Ser Gln Arg Gly
                165                 170                 175

Gly Glu Gln Gln Ala Ala Ile Phe Glu Ser Gly Leu Ser Pro Ser
            180                 185                 190

Arg Val Cys Ile Gly His Ser Asp Asp Thr Asp Leu Ser Tyr Leu
        195                 200                 205

Thr Ala Leu Ala Ala Arg Gly Tyr Leu Ile Gly Leu Asp His Ile Pro
```

```
                    210                 215                 220
His Ser Ala Ile Gly Leu Glu Asp Asn Ala Ser Ala Ser Ala Leu Leu
225                 230                 235                 240

Gly Ile Arg Ser Trp Gln Thr Arg Ala Leu Leu Ile Lys Ala Leu Ile
                245                 250                 255

Asp Gln Gly Tyr Met Lys Gln Ile Leu Val Ser Asn Asp Trp Leu Phe
            260                 265                 270

Gly Phe Ser Ser Tyr Val Thr Asn Ile Met Asp Val Met Asp Ser Val
        275                 280                 285

Asn Pro Asp Gly Met Ala Phe Ile Pro Leu Arg Val Ile Pro Phe Leu
    290                 295                 300

Arg Glu Lys Gly Val Pro Gln Glu Thr Leu Ala Gly Ile Thr Val Thr
305                 310                 315                 320

Asn Pro Ala Arg Phe Leu Ser Pro Thr Leu Arg Ala Ser
                325                 330

<210> SEQ ID NO 37
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (47)..(47)
<223> OTHER INFORMATION: Para-fluoro Phe
<220> FEATURE:
<221> NAME/KEY: MOD_RES
<222> LOCATION: (54)..(55)
<223> OTHER INFORMATION: Para-fluoro Phe
<220> FEATURE:
<221> NAME/KEY: MOD_RES
<222> LOCATION: (86)..(86)
<223> OTHER INFORMATION: Para-fluoro Phe
<220> FEATURE:
<221> NAME/KEY: MOD_RES
<222> LOCATION: (114)..(114)
<223> OTHER INFORMATION: Para-fluoro Phe
<220> FEATURE:
<221> NAME/KEY: MOD_RES
<222> LOCATION: (131)..(132)
<223> OTHER INFORMATION: Para-fluoro Phe
<220> FEATURE:
<221> NAME/KEY: MOD_RES
<222> LOCATION: (161)..(161)
<223> OTHER INFORMATION: Para-fluoro Phe
<220> FEATURE:
<221> NAME/KEY: MOD_RES
<222> LOCATION: (198)..(198)
<223> OTHER INFORMATION: Para-fluoro Phe
<220> FEATURE:
<221> NAME/KEY: MOD_RES
<222> LOCATION: (286)..(286)
<223> OTHER INFORMATION: Para-fluoro Phe
<220> FEATURE:
<221> NAME/KEY: MOD_RES
<222> LOCATION: (288)..(288)
<223> OTHER INFORMATION: Para-fluoro Phe
<220> FEATURE:
<221> NAME/KEY: MOD_RES
<222> LOCATION: (309)..(309)
<223> OTHER INFORMATION: Para-fluoro Phe
<220> FEATURE:
<221> NAME/KEY: MOD_RES
<222> LOCATION: (317)..(317)
<223> OTHER INFORMATION: Para-fluoro Phe
<220> FEATURE:
<221> NAME/KEY: MOD_RES
<222> LOCATION: (339)..(339)
<223> OTHER INFORMATION: Para-fluoro Phe
```

<400> SEQUENCE: 37

```
Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Leu Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
50                  55                  60

Ala Val Arg Gly Leu Arg Arg Ala Arg Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
        195                 200                 205

Cys Ile Gly His Ser Asp Asp Thr Asp Leu Ser Tyr Leu Thr Ala
210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
                245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
        275                 280                 285

Ser Ser Tyr Val Thr Asn Ile Met Asp Val Met Asp Ser Val Asn Pro
290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
                325                 330                 335

Ala Arg Phe Leu Ser Pro Thr Leu Arg Ala Ser
            340                 345
```

<210> SEQ ID NO 38
<211> LENGTH: 347
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES

```
<222> LOCATION: (33)..(33)
<223> OTHER INFORMATION: Para-fluoro Phe
<220> FEATURE:
<221> NAME/KEY: MOD_RES
<222> LOCATION: (47)..(47)
<223> OTHER INFORMATION: Para-fluoro Phe
<220> FEATURE:
<221> NAME/KEY: MOD_RES
<222> LOCATION: (54)..(55)
<223> OTHER INFORMATION: Para-fluoro Phe
<220> FEATURE:
<221> NAME/KEY: MOD_RES
<222> LOCATION: (86)..(86)
<223> OTHER INFORMATION: Para-fluoro Phe
<220> FEATURE:
<221> NAME/KEY: MOD_RES
<222> LOCATION: (114)..(114)
<223> OTHER INFORMATION: Para-fluoro Phe
<220> FEATURE:
<221> NAME/KEY: MOD_RES
<222> LOCATION: (131)..(131)
<223> OTHER INFORMATION: Para-fluoro Phe
<220> FEATURE:
<221> NAME/KEY: MOD_RES
<222> LOCATION: (161)..(161)
<223> OTHER INFORMATION: Para-fluoro Phe
<220> FEATURE:
<221> NAME/KEY: MOD_RES
<222> LOCATION: (198)..(198)
<223> OTHER INFORMATION: Para-fluoro Phe
<220> FEATURE:
<221> NAME/KEY: MOD_RES
<222> LOCATION: (286)..(286)
<223> OTHER INFORMATION: Para-fluoro Phe
<220> FEATURE:
<221> NAME/KEY: MOD_RES
<222> LOCATION: (288)..(288)
<223> OTHER INFORMATION: Para-fluoro Phe
<220> FEATURE:
<221> NAME/KEY: MOD_RES
<222> LOCATION: (309)..(309)
<223> OTHER INFORMATION: Para-fluoro Phe
<220> FEATURE:
<221> NAME/KEY: MOD_RES
<222> LOCATION: (317)..(317)
<223> OTHER INFORMATION: Para-fluoro Phe
<220> FEATURE:
<221> NAME/KEY: MOD_RES
<222> LOCATION: (339)..(339)
<223> OTHER INFORMATION: Para-fluoro Phe

<400> SEQUENCE: 38

Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
    50                  55                  60

Ala Val Arg Gly Leu Arg Arg Ala Arg Ala Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Met Leu Arg Glu Ile Gln Tyr Gly Ile Glu Asp Thr Gly
    130                 135                 140
```

-continued

```
Ile Arg Ala Gly Ile Ile Lys Val Ala Thr Thr Gly Lys Ala Thr Pro
145                 150                 155                 160

Phe Gln Glu Leu Val Leu Arg Ala Ala Arg Ala Ser Leu Ala Thr
            165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
            195                 200                 205

Cys Ile Gly His Ser Asp Asp Thr Asp Leu Ser Tyr Leu Thr Ala
            210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
            245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
            275                 280                 285

Ser Ser Tyr Val Thr Asn Ile Met Asp Val Met Asp Ser Val Asn Pro
            290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
            325                 330                 335

Ala Arg Phe Leu Ser Pro Thr Leu Arg Ala Ser
            340                 345

<210> SEQ ID NO 39
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Para-fluoro Phe
<220> FEATURE:
<221> NAME/KEY: MOD_RES
<222> LOCATION: (47)..(47)
<223> OTHER INFORMATION: Para-fluoro Phe
<220> FEATURE:
<221> NAME/KEY: MOD_RES
<222> LOCATION: (54)..(55)
<223> OTHER INFORMATION: Para-fluoro Phe
<220> FEATURE:
<221> NAME/KEY: MOD_RES
<222> LOCATION: (86)..(86)
<223> OTHER INFORMATION: Para-fluoro Phe
<220> FEATURE:
<221> NAME/KEY: MOD_RES
<222> LOCATION: (114)..(114)
<223> OTHER INFORMATION: Para-fluoro Phe
<220> FEATURE:
<221> NAME/KEY: MOD_RES
<222> LOCATION: (131)..(132)
<223> OTHER INFORMATION: Para-fluoro Phe
<220> FEATURE:
<221> NAME/KEY: MOD_RES
<222> LOCATION: (161)..(161)
<223> OTHER INFORMATION: Para-fluoro Phe
<220> FEATURE:
<221> NAME/KEY: MOD_RES
<222> LOCATION: (286)..(286)
```

```
<223> OTHER INFORMATION: Para-fluoro Phe
<220> FEATURE:
<221> NAME/KEY: MOD_RES
<222> LOCATION: (288)..(288)
<223> OTHER INFORMATION: Para-fluoro Phe
<220> FEATURE:
<221> NAME/KEY: MOD_RES
<222> LOCATION: (309)..(309)
<223> OTHER INFORMATION: Para-fluoro Phe
<220> FEATURE:
<221> NAME/KEY: MOD_RES
<222> LOCATION: (317)..(317)
<223> OTHER INFORMATION: Para-fluoro Phe
<220> FEATURE:
<221> NAME/KEY: MOD_RES
<222> LOCATION: (339)..(339)
<223> OTHER INFORMATION: Para-fluoro Phe

<400> SEQUENCE: 39

Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
    50                  55                  60

Ala Val Arg Gly Leu Arg Arg Ala Arg Ala Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
    130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Leu Glu Ser Glu Gly Leu Ser Pro Ser Arg Val
        195                 200                 205

Cys Ile Gly His Ser Asp Asp Thr Asp Asp Leu Ser Tyr Leu Thr Ala
    210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
                245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
        275                 280                 285

Ser Ser Tyr Val Thr Asn Ile Met Asp Val Met Asp Ser Val Asn Pro
    290                 295                 300

Asp Gly Met Ala Phe Ile Pro Leu Arg Val Ile Pro Phe Leu Arg Glu
305                 310                 315                 320
```

-continued

```
Lys Gly Val Pro Gln Glu Thr Leu Ala Gly Ile Thr Val Thr Asn Pro
            325                 330                 335

Ala Arg Phe Leu Ser Pro Thr Leu Arg Ala Ser
            340                 345

<210> SEQ ID NO 40
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Para-fluoro Phe
<220> FEATURE:
<221> NAME/KEY: MOD_RES
<222> LOCATION: (47)..(47)
<223> OTHER INFORMATION: Para-fluoro Phe
<220> FEATURE:
<221> NAME/KEY: MOD_RES
<222> LOCATION: (54)..(55)
<223> OTHER INFORMATION: Para-fluoro Phe
<220> FEATURE:
<221> NAME/KEY: MOD_RES
<222> LOCATION: (86)..(86)
<223> OTHER INFORMATION: Para-fluoro Phe
<220> FEATURE:
<221> NAME/KEY: MOD_RES
<222> LOCATION: (114)..(114)
<223> OTHER INFORMATION: Para-fluoro Phe
<220> FEATURE:
<221> NAME/KEY: MOD_RES
<222> LOCATION: (131)..(132)
<223> OTHER INFORMATION: Para-fluoro Phe
<220> FEATURE:
<221> NAME/KEY: MOD_RES
<222> LOCATION: (161)..(161)
<223> OTHER INFORMATION: Para-fluoro Phe
<220> FEATURE:
<221> NAME/KEY: MOD_RES
<222> LOCATION: (198)..(198)
<223> OTHER INFORMATION: Para-fluoro Phe
<220> FEATURE:
<221> NAME/KEY: MOD_RES
<222> LOCATION: (288)..(288)
<223> OTHER INFORMATION: Para-fluoro Phe
<220> FEATURE:
<221> NAME/KEY: MOD_RES
<222> LOCATION: (309)..(309)
<223> OTHER INFORMATION: Para-fluoro Phe
<220> FEATURE:
<221> NAME/KEY: MOD_RES
<222> LOCATION: (317)..(317)
<223> OTHER INFORMATION: Para-fluoro Phe
<220> FEATURE:
<221> NAME/KEY: MOD_RES
<222> LOCATION: (339)..(339)
<223> OTHER INFORMATION: Para-fluoro Phe

<400> SEQUENCE: 40

Met Arg Gly Ser His His His His His Met Ile Thr Asn Ser Gly
1               5                   10                  15

Asp Arg Ile Asn Thr Val Arg Gly Pro Ile Thr Ile Ser Glu Ala Gly
                20                  25                  30

Phe Thr Leu Thr His Glu His Ile Cys Gly Ser Ser Ala Gly Phe Leu
            35                  40                  45

Arg Ala Trp Pro Glu Phe Phe Gly Ser Arg Lys Ala Leu Ala Glu Lys
        50                  55                  60

Ala Val Arg Gly Leu Arg Arg Ala Arg Ala Ala Gly Val Arg Thr Ile
```

-continued

```
                65                  70                  75                  80
        Val Asp Val Ser Thr Phe Asp Ile Gly Arg Asp Val Ser Leu Leu Ala
                        85                  90                  95

Glu Val Ser Arg Ala Ala Asp Val His Ile Val Ala Ala Thr Gly Leu
                        100                 105                 110

Trp Phe Asp Pro Pro Leu Ser Met Arg Leu Arg Ser Val Glu Glu Leu
                        115                 120                 125

Thr Gln Phe Phe Leu Arg Glu Ile Gln Tyr Gly Ile Glu Asp Thr Gly
                        130                 135                 140

Ile Arg Ala Gly Ile Ile Lys Val Ala Thr Thr Gly Lys Ala Thr Pro
        145                 150                 155                 160

Phe Gln Glu Leu Val Leu Arg Ala Ala Arg Ala Ser Leu Ala Thr
                        165                 170                 175

Gly Val Pro Val Thr Thr His Thr Ala Ala Ser Gln Arg Gly Gly Glu
                        180                 185                 190

Gln Gln Ala Ala Ile Phe Glu Ser Glu Gly Leu Ser Pro Ser Arg Val
                        195                 200                 205

Cys Ile Gly His Ser Asp Asp Thr Asp Asp Leu Ser Tyr Leu Thr Ala
                        210                 215                 220

Leu Ala Ala Arg Gly Tyr Leu Ile Gly Leu Asp His Ile Pro His Ser
        225                 230                 235                 240

Ala Ile Gly Leu Glu Asp Asn Ala Ser Ala Ser Ala Leu Leu Gly Ile
                        245                 250                 255

Arg Ser Trp Gln Thr Arg Ala Leu Leu Ile Lys Ala Leu Ile Asp Gln
                        260                 265                 270

Gly Tyr Met Lys Gln Ile Leu Val Ser Asn Asp Trp Leu Leu Gly Phe
                        275                 280                 285

Ser Ser Tyr Val Thr Asn Ile Met Asp Val Met Asp Ser Val Asn Pro
                        290                 295                 300

Asp Gly Met Ala Phe Ile Pro Leu Arg Val Ile Pro Phe Leu Arg Glu
        305                 310                 315                 320

Lys Gly Val Pro Gln Glu Thr Leu Ala Gly Ile Thr Val Thr Asn Pro
                        325                 330                 335

Ala Arg Phe Leu Ser Pro Thr Leu Arg Ala Ser
                        340                 345

<210> SEQ ID NO 41
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Para-fluoro Phe
<220> FEATURE:
<221> NAME/KEY: MOD_RES
<222> LOCATION: (47)..(47)
<223> OTHER INFORMATION: Para-fluoro Phe
<220> FEATURE:
<221> NAME/KEY: MOD_RES
<222> LOCATION: (54)..(55)
<223> OTHER INFORMATION: Para-fluoro Phe
<220> FEATURE:
<221> NAME/KEY: MOD_RES
<222> LOCATION: (86)..(86)
<223> OTHER INFORMATION: Para-fluoro Phe
<220> FEATURE:
<221> NAME/KEY: MOD_RES
```

```
<222> LOCATION: (114)..(114)
<223> OTHER INFORMATION: Para-fluoro Phe
<220> FEATURE:
<221> NAME/KEY: MOD_RES
<222> LOCATION: (131)..(132)
<223> OTHER INFORMATION: Para-fluoro Phe
<220> FEATURE:
<221> NAME/KEY: MOD_RES
<222> LOCATION: (161)..(161)
<223> OTHER INFORMATION: Para-fluoro Phe
<220> FEATURE:
<221> NAME/KEY: MOD_RES
<222> LOCATION: (198)..(198)
<223> OTHER INFORMATION: Para-fluoro Phe
<220> FEATURE:
<221> NAME/KEY: MOD_RES
<222> LOCATION: (286)..(286)
<223> OTHER INFORMATION: Para-fluoro Phe
<220> FEATURE:
<221> NAME/KEY: MOD_RES
<222> LOCATION: (309)..(309)
<223> OTHER INFORMATION: Para-fluoro Phe
<220> FEATURE:
<221> NAME/KEY: MOD_RES
<222> LOCATION: (317)..(317)
<223> OTHER INFORMATION: Para-fluoro Phe
<220> FEATURE:
<221> NAME/KEY: MOD_RES
<222> LOCATION: (339)..(339)
<223> OTHER INFORMATION: Para-fluoro Phe

<400> SEQUENCE: 41

Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
    50                  55                  60

Ala Val Arg Gly Leu Arg Arg Ala Arg Ala Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
    130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
        195                 200                 205

Cys Ile Gly His Ser Asp Asp Thr Asp Asp Leu Ser Tyr Leu Thr Ala
    210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
```

```
                    245                 250                 255
Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Leu
        275                 280                 285

Ser Ser Tyr Val Thr Asn Ile Met Asp Val Met Asp Ser Val Asn Pro
    290                 295                 300

Asp Gly Met Ala Phe Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
                325                 330                 335

Ala Arg Phe Leu Ser Pro Thr Leu Arg Ala Ser
            340                 345

<210> SEQ ID NO 42
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Para-fluoro Phe
<220> FEATURE:
<221> NAME/KEY: MOD_RES
<222> LOCATION: (47)..(47)
<223> OTHER INFORMATION: Para-fluoro Phe
<220> FEATURE:
<221> NAME/KEY: MOD_RES
<222> LOCATION: (54)..(55)
<223> OTHER INFORMATION: Para-fluoro Phe
<220> FEATURE:
<221> NAME/KEY: MOD_RES
<222> LOCATION: (86)..(86)
<223> OTHER INFORMATION: Para-fluoro Phe
<220> FEATURE:
<221> NAME/KEY: MOD_RES
<222> LOCATION: (114)..(114)
<223> OTHER INFORMATION: Para-fluoro Phe
<220> FEATURE:
<221> NAME/KEY: MOD_RES
<222> LOCATION: (131)..(132)
<223> OTHER INFORMATION: Para-fluoro Phe
<220> FEATURE:
<221> NAME/KEY: MOD_RES
<222> LOCATION: (161)..(161)
<223> OTHER INFORMATION: Para-fluoro Phe
<220> FEATURE:
<221> NAME/KEY: MOD_RES
<222> LOCATION: (198)..(198)
<223> OTHER INFORMATION: Para-fluoro Phe
<220> FEATURE:
<221> NAME/KEY: MOD_RES
<222> LOCATION: (286)..(286)
<223> OTHER INFORMATION: Para-fluoro Phe
<220> FEATURE:
<221> NAME/KEY: MOD_RES
<222> LOCATION: (288)..(288)
<223> OTHER INFORMATION: Para-fluoro Phe
<220> FEATURE:
<221> NAME/KEY: MOD_RES
<222> LOCATION: (317)..(317)
<223> OTHER INFORMATION: Para-fluoro Phe
<220> FEATURE:
<221> NAME/KEY: MOD_RES
<222> LOCATION: (339)..(339)
<223> OTHER INFORMATION: Para-fluoro Phe

<400> SEQUENCE: 42
```

```
Met Arg Gly Ser His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
50                  55                  60

Ala Val Arg Gly Leu Arg Ala Arg Ala Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Arg Ala Ser Leu Ala Thr
                165                 170                 175

Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
        195                 200                 205

Cys Ile Gly His Ser Asp Asp Thr Asp Asp Leu Ser Tyr Leu Thr Ala
210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
                245                 250                 255

Arg Ser Trp Gln Thr Arg Ala Leu Leu Ile Lys Ala Leu Ile Asp Gln
            260                 265                 270

Gly Tyr Met Lys Gln Ile Leu Val Ser Asn Asp Trp Leu Phe Gly Phe
        275                 280                 285

Ser Ser Tyr Val Thr Asn Ile Met Asp Val Met Asp Ser Val Asn Pro
290                 295                 300

Asp Gly Met Ala Leu Ile Pro Leu Arg Val Ile Pro Phe Leu Arg Glu
305                 310                 315                 320

Lys Gly Val Pro Gln Glu Thr Leu Ala Gly Ile Thr Val Thr Asn Pro
                325                 330                 335

Ala Arg Phe Leu Ser Pro Thr Leu Arg Ala Ser
            340                 345

<210> SEQ ID NO 43
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Para-fluoro Phe
<220> FEATURE:
```

-continued

```
<221> NAME/KEY: MOD_RES
<222> LOCATION: (47)..(47)
<223> OTHER INFORMATION: Para-fluoro Phe
<220> FEATURE:
<221> NAME/KEY: MOD_RES
<222> LOCATION: (54)..(55)
<223> OTHER INFORMATION: Para-fluoro Phe
<220> FEATURE:
<221> NAME/KEY: MOD_RES
<222> LOCATION: (86)..(86)
<223> OTHER INFORMATION: Para-fluoro Phe
<220> FEATURE:
<221> NAME/KEY: MOD_RES
<222> LOCATION: (114)..(114)
<223> OTHER INFORMATION: Para-fluoro Phe
<220> FEATURE:
<221> NAME/KEY: MOD_RES
<222> LOCATION: (131)..(132)
<223> OTHER INFORMATION: Para-fluoro Phe
<220> FEATURE:
<221> NAME/KEY: MOD_RES
<222> LOCATION: (161)..(161)
<223> OTHER INFORMATION: Para-fluoro Phe
<220> FEATURE:
<221> NAME/KEY: MOD_RES
<222> LOCATION: (198)..(198)
<223> OTHER INFORMATION: Para-fluoro Phe
<220> FEATURE:
<221> NAME/KEY: MOD_RES
<222> LOCATION: (286)..(286)
<223> OTHER INFORMATION: Para-fluoro Phe
<220> FEATURE:
<221> NAME/KEY: MOD_RES
<222> LOCATION: (288)..(288)
<223> OTHER INFORMATION: Para-fluoro Phe
<220> FEATURE:
<221> NAME/KEY: MOD_RES
<222> LOCATION: (309)..(309)
<223> OTHER INFORMATION: Para-fluoro Phe
<220> FEATURE:
<221> NAME/KEY: MOD_RES
<222> LOCATION: (339)..(339)
<223> OTHER INFORMATION: Para-fluoro Phe

<400> SEQUENCE: 43

Met Arg Gly Ser His His His His His His Met Ile Thr Asn Ser Gly
1               5                   10                  15

Asp Arg Ile Asn Thr Val Arg Gly Pro Ile Thr Ile Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Ala Glu Lys
    50                  55                  60

Ala Val Arg Gly Leu Arg Arg Ala Arg Ala Ala Gly Val Arg Thr Ile
65                  70                  75                  80

Val Asp Val Ser Thr Phe Asp Ile Gly Arg Asp Val Ser Leu Leu Ala
                85                  90                  95

Glu Val Ser Arg Ala Ala Asp Val His Ile Val Ala Ala Thr Gly Leu
            100                 105                 110

Trp Phe Asp Pro Pro Leu Ser Met Arg Leu Arg Ser Val Glu Glu Leu
        115                 120                 125

Thr Gln Phe Phe Leu Arg Glu Ile Gln Tyr Gly Ile Glu Asp Thr Gly
    130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Ala Arg Ala Ser Leu Ala Thr
                165                 170                 175
```

```
Gly Val Pro Val Thr Thr His Thr Ala Ala Ser Gln Arg Gly Gly Glu
            180                 185                 190

Gln Gln Ala Ala Ile Phe Glu Ser Glu Gly Leu Ser Pro Ser Arg Val
        195                 200                 205

Cys Ile Gly His Ser Asp Asp Thr Asp Leu Ser Tyr Leu Thr Ala
    210                 215                 220

Leu Ala Ala Arg Gly Tyr Leu Ile Gly Leu Asp His Ile Pro His Ser
225                 230                 235                 240

Ala Ile Gly Leu Glu Asp Asn Ala Ser Ala Ser Ala Leu Leu Gly Ile
                245                 250                 255

Arg Ser Trp Gln Thr Arg Ala Leu Leu Ile Lys Ala Leu Ile Asp Gln
                260                 265                 270

Gly Tyr Met Lys Gln Ile Leu Val Ser Asn Asp Trp Leu Phe Gly Phe
            275                 280                 285

Ser Ser Tyr Val Thr Asn Ile Met Asp Val Met Asp Ser Val Asn Pro
        290                 295                 300

Asp Gly Met Ala Phe Ile Pro Leu Arg Val Ile Pro Met Leu Arg Glu
305                 310                 315                 320

Lys Gly Val Pro Gln Glu Thr Leu Ala Gly Ile Thr Val Thr Asn Pro
                325                 330                 335

Ala Arg Phe Leu Ser Pro Thr Leu Arg Ala Ser
            340                 345

<210> SEQ ID NO 44
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Para-fluoro Phe
<220> FEATURE:
<221> NAME/KEY: MOD_RES
<222> LOCATION: (47)..(47)
<223> OTHER INFORMATION: Para-fluoro Phe
<220> FEATURE:
<221> NAME/KEY: MOD_RES
<222> LOCATION: (54)..(55)
<223> OTHER INFORMATION: Para-fluoro Phe
<220> FEATURE:
<221> NAME/KEY: MOD_RES
<222> LOCATION: (86)..(86)
<223> OTHER INFORMATION: Para-fluoro Phe
<220> FEATURE:
<221> NAME/KEY: MOD_RES
<222> LOCATION: (114)..(114)
<223> OTHER INFORMATION: Para-fluoro Phe
<220> FEATURE:
<221> NAME/KEY: MOD_RES
<222> LOCATION: (131)..(132)
<223> OTHER INFORMATION: Para-fluoro Phe
<220> FEATURE:
<221> NAME/KEY: MOD_RES
<222> LOCATION: (161)..(161)
<223> OTHER INFORMATION: Para-fluoro Phe
<220> FEATURE:
<221> NAME/KEY: MOD_RES
<222> LOCATION: (198)..(198)
<223> OTHER INFORMATION: Para-fluoro Phe
<220> FEATURE:
<221> NAME/KEY: MOD_RES
<222> LOCATION: (286)..(286)
<223> OTHER INFORMATION: Para-fluoro Phe
<220> FEATURE:
<221> NAME/KEY: MOD_RES
```

```
<222> LOCATION: (288)..(288)
<223> OTHER INFORMATION: Para-fluoro Phe
<220> FEATURE:
<221> NAME/KEY: MOD_RES
<222> LOCATION: (309)..(309)
<223> OTHER INFORMATION: Para-fluoro Phe
<220> FEATURE:
<221> NAME/KEY: MOD_RES
<222> LOCATION: (317)..(317)
<223> OTHER INFORMATION: Para-fluoro Phe

<400> SEQUENCE: 44
```

| | | | | | | | | | | | | | | |
|---|---|---|---|---|---|---|---|---|---|---|---|---|---|---|
| Met | Arg | Gly | Ser | His | His | His | His | His | Met | Ile | Thr | Asn | Ser | Gly |
| 1 | | | | 5 | | | | | 10 | | | | | 15 |
| Asp | Arg | Ile | Asn | Thr | Val | Arg | Gly | Pro | Ile | Thr | Ile | Ser | Glu | Ala | Gly |
| | | | 20 | | | | | 25 | | | | | 30 | | |
| Phe | Thr | Leu | Thr | His | Glu | His | Ile | Cys | Gly | Ser | Ser | Ala | Gly | Phe | Leu |
| | | | 35 | | | | | 40 | | | | | 45 | | |
| Arg | Ala | Trp | Pro | Glu | Phe | Phe | Gly | Ser | Arg | Lys | Ala | Leu | Ala | Glu | Lys |
| | 50 | | | | | 55 | | | | | 60 | | | | |
| Ala | Val | Arg | Gly | Leu | Arg | Ala | Arg | Ala | Ala | Gly | Val | Arg | Thr | Ile |
| 65 | | | | 70 | | | | | 75 | | | | | 80 |
| Val | Asp | Val | Ser | Thr | Phe | Asp | Ile | Gly | Arg | Asp | Val | Ser | Leu | Leu | Ala |
| | | | | 85 | | | | | 90 | | | | | 95 | |
| Glu | Val | Ser | Arg | Ala | Ala | Asp | Val | His | Ile | Val | Ala | Ala | Thr | Gly | Leu |
| | | | 100 | | | | | 105 | | | | | 110 | | |
| Trp | Phe | Asp | Pro | Pro | Leu | Ser | Met | Arg | Leu | Arg | Ser | Val | Glu | Glu | Leu |
| | | 115 | | | | | 120 | | | | | 125 | | | |
| Thr | Gln | Phe | Phe | Leu | Arg | Glu | Ile | Gln | Tyr | Gly | Ile | Glu | Asp | Thr | Gly |
| | 130 | | | | | 135 | | | | | 140 | | | | |
| Ile | Arg | Ala | Gly | Ile | Ile | Lys | Val | Ala | Thr | Thr | Gly | Lys | Ala | Thr | Pro |
| 145 | | | | | 150 | | | | | 155 | | | | | 160 |
| Phe | Gln | Glu | Leu | Val | Leu | Arg | Ala | Ala | Arg | Ala | Ser | Leu | Ala | Thr |
| | | | 165 | | | | | 170 | | | | | 175 | |
| Gly | Val | Pro | Val | Thr | Thr | His | Thr | Ala | Ala | Ser | Gln | Arg | Gly | Gly | Glu |
| | | | 180 | | | | | 185 | | | | | 190 | | |
| Gln | Gln | Ala | Ala | Ile | Phe | Glu | Ser | Glu | Gly | Leu | Ser | Pro | Ser | Arg | Val |
| | 195 | | | | | 200 | | | | | 205 | | | | |
| Cys | Ile | Gly | His | Ser | Asp | Asp | Thr | Asp | Asp | Leu | Ser | Tyr | Leu | Thr | Ala |
| 210 | | | | | 215 | | | | | 220 | | | | | |
| Leu | Ala | Ala | Arg | Gly | Tyr | Leu | Ile | Gly | Leu | Asp | His | Ile | Pro | His | Ser |
| 225 | | | | | 230 | | | | | 235 | | | | | 240 |
| Ala | Ile | Gly | Leu | Glu | Asp | Asn | Ala | Ser | Ala | Ser | Ala | Leu | Leu | Gly | Ile |
| | | | | 245 | | | | | 250 | | | | | 255 | |
| Arg | Ser | Trp | Gln | Thr | Arg | Ala | Leu | Leu | Ile | Lys | Ala | Leu | Ile | Asp | Gln |
| | | | 260 | | | | | 265 | | | | | 270 | | |
| Gly | Tyr | Met | Lys | Gln | Ile | Leu | Val | Ser | Asn | Asp | Trp | Leu | Phe | Gly | Phe |
| | 275 | | | | | 280 | | | | | 285 | | | | |
| Ser | Ser | Tyr | Val | Thr | Asn | Ile | Met | Asp | Val | Met | Asp | Ser | Val | Asn | Pro |
| | 290 | | | | | 295 | | | | | 300 | | | | |
| Asp | Gly | Met | Ala | Phe | Ile | Pro | Leu | Arg | Val | Ile | Pro | Phe | Leu | Arg | Glu |
| 305 | | | | | 310 | | | | | 315 | | | | | 320 |
| Lys | Gly | Val | Pro | Gln | Glu | Thr | Leu | Ala | Gly | Ile | Thr | Val | Thr | Asn | Pro |
| | | | 325 | | | | | 330 | | | | | 335 | | |
| Ala | Arg | Leu | Leu | Ser | Pro | Thr | Leu | Arg | Ala | Ser |
| | | 340 | | | | | 345 | | | |

```
<210> SEQ ID NO 45
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 45

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Gly Gly Arg Asp Val Ser Leu Leu Ala
65                  70                  75                  80

Glu Val Ser Arg Ala Ala Asp Val His Ile Val Ala Ala Thr Gly Leu
                85                  90                  95

Ser Trp Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125
```

```
Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
                180                 185                 190

Cys Ile Gly His Ser Asp Ser Thr Asp Asp Leu Ser Tyr Leu Thr Ala
                195                 200                 205

Leu Ala Ala Arg Gly Tyr Leu Ile Gly Leu Asp Gly Ile Pro Leu Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Gly Phe Gly Asp
                260                 265                 270

Ser Gly Gly Val Thr Asn Ile Met Asp Val Arg Asp Ser Val Asn Pro
                275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 46
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (223)..(223)
<223> OTHER INFORMATION: Para-fluoro Phe
```

```
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 46

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Ala Arg Ala Ala Gly Val Arg Thr Ile
50                  55                  60

Val Asp Val Ser Thr Phe Asp Ser Gly Arg Asp Val Ser Leu Leu Ala
65                  70                  75                  80

Glu Val Ser Arg Ala Ala Asp Val His Ile Val Ala Ala Thr Gly Leu
                85                  90                  95

Ser Trp Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asn Thr Asp Asp Leu Ser Tyr Leu Thr Ala
        195                 200                 205

Leu Ala Ala Arg Gly Tyr Leu Ile Gly Leu Asp Gly Ile Pro Phe Ser
210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Ala Phe Gly Met
            260                 265                 270

Ser Ala Gly Val Thr Asn Ile Met Asp Val Leu Asp Ser Val Asn Pro
        275                 280                 285

Asp Gly Met Ala Phe Ile Pro Leu Arg Val Ile Pro Phe Leu Arg Glu
290                 295                 300

Lys Gly Val Pro Gln Glu Thr Leu Ala Gly Ile Thr Val Thr Asn Pro
305                 310                 315                 320
```

Ala Arg Phe Leu Ser Pro Thr Leu Arg Ala Ser
            325                 330

<210> SEQ ID NO 47
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (98)..(98)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 47

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Leu Gly Arg Asp Val Ser Leu Leu Ala
65                  70                  75                  80

Glu Val Ser Arg Ala Ala Asp Val His Ile Val Ala Ala Thr Gly Leu
                85                  90                  95

```
Gly Phe Asp Pro Pro Leu Ser Met Arg Leu Arg Ser Val Glu Glu Leu
                100                 105                 110

Thr Gln Phe Phe Leu Arg Glu Ile Gln Tyr Gly Ile Glu Asp Thr Gly
            115                 120                 125

Ile Arg Ala Gly Ile Ile Leu Val Ala Thr Thr Gly Lys Ala Thr Pro
130                 135                 140

Phe Gln Glu Leu Val Leu Arg Ala Ala Arg Ala Ser Leu Ala Thr
145                 150                 155                 160

Gly Val Pro Val Thr Thr His Thr Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Leu Ser Tyr Leu Thr Ala
                195                 200                 205

Leu Ala Ala Arg Gly Tyr Leu Ile Gly Leu Asp His Ile Pro His Ser
210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Cys Phe Gly Asn
                260                 265                 270

Ser Leu Gly Val Thr Asn Ile Met Asp Val His Asp Ser Val Asn Pro
            275                 280                 285

Asp Gly Met Ala Phe Ile Pro Leu Arg Val Ile Pro Phe Leu Arg Glu
        290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 48
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
```

```
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (274)..(274)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 48

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Thr Gly Arg Asp Val Ser Leu Leu Ala
65                  70                  75                  80

Glu Val Ser Arg Ala Ala Asp Val His Ile Val Ala Thr Gly Leu
                85                  90                  95

Gly Met Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Glu Thr Asp Asp Leu Ser Tyr Leu Thr Ala
        195                 200                 205

Leu Ala Ala Arg Gly Tyr Leu Ile Gly Leu Asp Asn Ile Pro Ala Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Ala Phe Gly Ile
            260                 265                 270

Ser Phe Gly Val Thr Asn Ile Met Asp Val His Asp Ser Val Asn Pro
        275                 280                 285
```

```
Asp Gly Met Ala Phe Ile Pro Leu Arg Val Ile Pro Phe Leu Arg Glu
            290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 49
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 49

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Leu Gly Arg Asp Val Ser Leu Leu Ala
65                  70                  75                  80
```

Glu Val Ser Arg Ala Ala Asp Val His Ile Val Ala Ala Thr Gly Leu
            85                  90                  95

Gly Leu Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Leu Ser Tyr Leu Thr Ala
            195                 200                 205

Leu Ala Ala Arg Gly Tyr Leu Ile Gly Leu Asp Ala Ile Pro His Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Cys Phe Gly Leu
            260                 265                 270

Ser Ala Gly Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 50
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (98)..(98)
<223> OTHER INFORMATION: Para-fluoro Phe
<220> FEATURE:
<221> NAME/KEY: MOD_RES

```
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 50

Asp Arg Ile Asn Thr Val Arg Gly Pro Ile Thr Ile Ser Glu Ala Gly
1               5                   10                  15

Phe Thr Leu Thr His Glu His Ile Cys Gly Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Gln Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Phe Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp His Ile Pro His Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Gly Phe Gly Leu
            260                 265                 270
```

```
Ser Ala Gly Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
        290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 51
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 51

Asp Arg Ile Asn Thr Val Arg Gly Pro Ile Thr Ile Ser Glu Ala Gly
1               5                   10                  15

Phe Thr Leu Thr His Glu His Ile Cys Met Ser Ser Ala Gly Phe Leu
                20                  25                  30

Arg Ala Trp Pro Glu Phe Phe Gly Ser Arg Lys Ala Leu Ala Glu Lys
            35                  40                  45

Ala Val Arg Gly Leu Arg Arg Ala Arg Ala Ala Gly Val Arg Thr Ile
    50                  55                  60
```

```
Val Asp Val Ser Thr Phe Asp Thr Gly Arg Asp Val Ser Leu Leu Ala
 65                  70                  75                  80

Glu Val Ser Arg Ala Ala Asp Val His Ile Val Ala Ala Thr Gly Leu
             85                  90                  95

Gly Trp Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp His Ile Pro His Ser
210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Ser Phe Gly Asn
            260                 265                 270

Ser Leu Gly Val Thr Asn Ile Met Asp Val Glu Asp Ser Val Asn Pro
        275                 280                 285

Asp Gly Met Ala Phe Ile Pro Leu Arg Val Ile Pro Phe Leu Arg Glu
290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330
```

```
<210> SEQ ID NO 52
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (98)..(98)
```

```
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 52

Asp Arg Ile Asn Thr Val Arg Gly Pro Ile Thr Ile Ser Glu Ala Gly
 1               5                  10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Gln Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Phe Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Leu Ser Tyr Leu Thr Ala
        195                 200                 205

Leu Ala Ala Arg Gly Tyr Leu Ile Gly Leu Asp His Ile Pro His Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255
```

-continued

```
Gly Tyr Met Lys Gln Ile Leu Val Ser Asn Asp Tyr Gly Phe Gly Met
            260                 265                 270

Ser Ala Gly Val Thr Asn Ile Met Asp Val Ile Asp Ser Val Asn Pro
        275                 280                 285

Asp Gly Met Ala Phe Ile Pro Leu Arg Val Ile Pro Phe Leu Arg Glu
290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 53
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 53

Asp Arg Ile Asn Thr Val Arg Gly Pro Ile Thr Ile Ser Glu Ala Gly
1               5                   10                  15

Phe Thr Leu Thr His Glu His Ile Cys Ala Ser Ser Ala Gly Phe Leu
            20                  25                  30

Arg Ala Trp Pro Glu Phe Phe Gly Ser Arg Lys Ala Leu Ala Glu Lys
        35                  40                  45
```

```
Ala Val Arg Gly Leu Arg Arg Ala Arg Ala Ala Gly Val Arg Thr Ile
             50                  55                  60

Val Asp Val Ser Thr Phe Asp Ser Gly Arg Asp Val Ser Leu Leu Ala
 65                  70                  75                  80

Glu Val Ser Arg Ala Ala Asp Val His Ile Val Ala Ala Thr Gly Leu
                 85                  90                  95

Gly Trp Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp His Ile Pro His Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Ser Phe Gly Val
            260                 265                 270

Ser Ile Gly Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 54
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
```

-continued

```
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 54

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Ser Gly Arg Asp Val Ser Leu Leu Ala
65                  70                  75                  80

Glu Val Ser Arg Ala Ala Asp Val His Ile Val Ala Thr Gly Leu
                85                  90                  95

Trp Ala Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp His Ile Pro His Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255
```

```
Gly Tyr Met Lys Gln Ile Leu Val Ser Asn Asp Trp Ala Phe Gly Gly
                260                 265                 270

Ser Asn Tyr Val Thr Asn Ile Met Asp Val Trp Asp Ser Val Asn Pro
            275                 280                 285

Asp Gly Met Ala Phe Ile Pro Leu Arg Val Ile Pro Phe Leu Arg Glu
        290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 55
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 55

Asp Arg Ile Asn Thr Val Arg Gly Pro Ile Thr Ile Ser Glu Ala Gly
1               5                   10                  15

Phe Thr Leu Thr His Glu His Ile Cys Met Ser Ser Ala Gly Phe Leu
            20                  25                  30

Arg Ala Trp Pro Glu Phe Phe Gly Ser Arg Lys Ala Leu Ala Glu Lys
        35                  40                  45
```

```
Ala Val Arg Gly Leu Arg Arg Ala Arg Ala Ala Gly Val Arg Thr Ile
 50                  55                  60
Val Asp Val Ser Thr Phe Asp Gln Gly Arg Asp Val Ser Leu Leu Ala
 65                  70                  75                  80
Glu Val Ser Arg Ala Ala Asp Val His Ile Val Ala Ala Thr Gly Leu
                 85                  90                  95
Gly Trp Asp Pro Pro Leu Ser Met Arg Leu Arg Ser Val Glu Glu Leu
                100                 105                 110
Thr Gln Phe Phe Leu Arg Glu Ile Gln Tyr Gly Ile Glu Asp Thr Gly
            115                 120                 125
Ile Arg Ala Gly Ile Ile Leu Val Ala Thr Thr Gly Lys Ala Thr Pro
        130                 135                 140
Phe Gln Glu Leu Val Leu Arg Ala Ala Arg Ala Ser Leu Ala Thr
145                 150                 155                 160
Gly Val Pro Val Thr Thr His Thr Ala Ala Ser Gln Arg Gly Gly Glu
                165                 170                 175
Gln Gln Ala Ala Ile Phe Glu Ser Glu Gly Leu Ser Pro Ser Arg Val
            180                 185                 190
Cys Ile Gly His Ser Asp Ser Thr Asp Asp Leu Ser Tyr Leu Thr Ala
        195                 200                 205
Leu Ala Ala Arg Gly Tyr Leu Ile Gly Leu Asp Ser Ile Pro Trp Ser
210                 215                 220
Ala Ile Gly Leu Glu Asp Asn Ala Ser Ala Ser Ala Trp Leu Gly Ile
225                 230                 235                 240
Arg Ser Trp Gln Thr Arg Ala Leu Leu Ile Lys Ala Leu Ile Asp Gln
                245                 250                 255
Gly Tyr Met Lys Gln Ile Leu Val Ser Asn Asp Trp Gly Phe Gly Ala
            260                 265                 270
Ser Ala Gly Val Thr Asn Ile Met Asp Val Tyr Asp Ser Val Asn Pro
        275                 280                 285
Asp Gly Met Ala Phe Ile Pro Leu Arg Val Ile Pro Phe Leu Arg Glu
    290                 295                 300
Lys Gly Val Pro Gln Glu Thr Leu Ala Gly Ile Thr Val Thr Asn Pro
305                 310                 315                 320
Ala Arg Phe Leu Ser Pro Thr Leu Arg Ala Ser
                325                 330
```

<210> SEQ ID NO 56
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:

```
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 56

Asp Arg Ile Asn Thr Val Arg Gly Pro Ile Thr Ile Ser Glu Ala Gly
1               5                   10                  15

Phe Thr Leu Thr His Glu His Ile Cys Cys Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Gln Gly Arg Asp Val Ser Leu Leu Ala
65                  70                  75                  80

Glu Val Ser Arg Ala Ala Asp Val His Ile Val Ala Thr Gly Leu
                85                  90                  95

Gly Asn Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp Cys Ile Pro Trp Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Gly Phe Gly Ala
```

```
                260                 265                 270
Ser Ala Gly Val Thr Asn Ile Met Asp Val Leu Asp Ser Val Asn Pro
            275                 280                 285

Asp Gly Met Ala Phe Ile Pro Leu Arg Val Ile Pro Phe Leu Arg Glu
        290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 57
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (223)..(223)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 57

Asp Arg Ile Asn Thr Val Arg Gly Pro Ile Thr Ile Ser Glu Ala Gly
1               5                   10                  15

Phe Thr Leu Thr His Glu His Ile Cys Val Ser Ser Ala Gly Phe Leu
            20                  25                  30
```

```
Arg Ala Trp Pro Glu Phe Phe Gly Ser Arg Lys Ala Leu Ala Glu Lys
             35                  40                  45

Ala Val Arg Gly Leu Arg Ala Arg Ala Gly Val Arg Thr Ile
 50                  55                  60

Val Asp Val Ser Thr Phe Asp Ala Gly Arg Asp Val Ser Leu Leu Ala
 65                  70                  75                  80

Glu Val Ser Arg Ala Ala Asp Val His Ile Val Ala Ala Thr Gly Leu
                 85                  90                  95

Trp Ala Asp Pro Pro Leu Ser Met Arg Leu Arg Ser Val Glu Glu Leu
                100                 105                 110

Thr Gln Phe Phe Leu Arg Glu Ile Gln Tyr Gly Ile Glu Asp Thr Gly
            115                 120                 125

Ile Arg Ala Gly Ile Ile Leu Val Ala Thr Thr Gly Lys Ala Thr Pro
130                 135                 140

Phe Gln Glu Leu Val Leu Arg Ala Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp His Ile Pro Phe Ser
210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Trp His Phe Gly Gly
            260                 265                 270

Ser Gly Tyr Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 58
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
```

```
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (223)..(223)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 58

Asp Arg Ile Asn Thr Val Arg Gly Pro Ile Thr Ile Ser Glu Ala Gly
1               5                   10                  15

Phe Thr Leu Thr His Glu His Ile Cys Gly Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Gln Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Leu Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp Gln Ile Pro Phe Ser
    210                 215                 220
```

```
Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Ala Phe Gly Leu
            260                 265                 270

Ser Ala Gly Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 59
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 59

Asp Arg Ile Asn Thr Val Arg Gly Pro Ile Thr Ile Ser Glu Ala Gly
1               5                   10                  15
```

Phe Thr Leu Thr His Glu His Ile Cys Val Ser Ala Gly Phe Leu
                20                  25                  30

Arg Ala Trp Pro Glu Phe Phe Gly Ser Arg Lys Ala Leu Ala Glu Lys
            35                  40                  45

Ala Val Arg Gly Leu Arg Arg Ala Ala Gly Val Arg Thr Ile
50                  55                  60

Val Asp Val Ser Thr Phe Asp Gln Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Pro Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asn Thr Asp Asp Leu Ser Tyr Leu Thr Ala
        195                 200                 205

Leu Ala Ala Arg Gly Tyr Leu Ile Gly Leu Asp Ala Ile Pro His Ser
210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Ala Phe Gly Leu
            260                 265                 270

Ser Asn Gly Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 60
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)

```
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 60

Asp Arg Ile Asn Thr Val Arg Gly Pro Ile Thr Ile Ser Glu Ala Gly
1               5                   10                  15

Phe Thr Leu Thr His Glu His Ile Cys Gly Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Gly Gly Arg Asp Val Ser Leu Leu Ala
65                  70                  75                  80

Glu Val Ser Arg Ala Ala Asp Val His Ile Val Ala Ala Thr Gly Leu
                85                  90                  95

Ser Trp Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Leu Ser Tyr Leu Thr Ala
        195                 200                 205

Leu Ala Ala Arg Gly Tyr Leu Ile Gly Leu Asp Ser Ile Pro Lys Ser
    210                 215                 220

Ala Ile Gly Leu Glu Asp Asn Ala Ser Ala Ser Ala Trp Leu Gly Ile
```

```
                    225                 230                 235                 240
        Arg Ser Trp Gln Thr Arg Ala Leu Leu Ile Lys Ala Leu Ile Asp Gln
                        245                 250                 255

Gly Tyr Met Lys Gln Ile Leu Val Ser Asn Asp Tyr Ala Phe Gly Leu
                        260                 265                 270

Ser Ala Gly Val Thr Asn Ile Met Asp Val His Asp Ser Val Asn Pro
                        275                 280                 285

Asp Gly Met Ala Phe Ile Pro Leu Arg Val Ile Pro Phe Leu Arg Glu
                        290                 295                 300

Lys Gly Val Pro Gln Glu Thr Leu Ala Gly Ile Thr Val Thr Asn Pro
        305                 310                 315                 320

Ala Arg Phe Leu Ser Pro Thr Leu Arg Ala Ser
                        325                 330

<210> SEQ ID NO 61
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 61

Asp Arg Ile Asn Thr Val Arg Gly Pro Ile Thr Ile Ser Glu Ala Gly
1               5                   10                  15

Phe Thr Leu Thr His Glu His Ile Cys Ala Ser Ser Ala Gly Phe Leu
```

```
                20                  25                  30
Arg Ala Trp Pro Glu Phe Phe Gly Ser Arg Lys Ala Leu Ala Glu Lys
            35                  40                  45

Ala Val Arg Gly Leu Arg Arg Ala Arg Ala Ala Gly Val Arg Thr Ile
        50                  55                  60

Val Asp Val Ser Thr Phe Asp Gln Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Trp Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Leu Ser Tyr Leu Thr Ala
        195                 200                 205

Leu Ala Ala Arg Gly Tyr Leu Ile Gly Leu Asp Gln Ile Pro His Ser
    210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Pro Phe Gly Val
            260                 265                 270

Ser Ala Gly Val Thr Asn Ile Met Asp Val Val Asp Ser Val Asn Pro
        275                 280                 285

Asp Gly Met Ala Phe Ile Pro Leu Arg Val Ile Pro Phe Leu Arg Glu
    290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 62
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
```

```
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (223)..(223)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 62

Asp Arg Ile Asn Thr Val Arg Gly Pro Ile Thr Ile Ser Glu Ala Gly
1               5                   10                  15

Phe Thr Leu Thr His Glu His Ile Cys Ala Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
50                  55                  60

Val Asp Val Ser Thr Phe Asp Asp Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Pro Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Leu Ser Tyr Leu Thr Ala
        195                 200                 205

Leu Ala Ala Arg Gly Tyr Leu Ile Gly Leu Asp Asn Ile Pro Phe Ser
```

```
                210                 215                 220
Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Pro Phe Gly Leu
            260                 265                 270

Ser Ala Gly Val Thr Asn Ile Met Asp Val Val Asp Ser Val Asn Pro
            275                 280                 285

Asp Gly Met Ala Phe Ile Pro Leu Arg Val Ile Pro Phe Leu Arg Glu
        290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330
```

<210> SEQ ID NO 63
<211> LENGTH: 331
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (17)..(17)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (223)..(223)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 63

```
Asp Arg Ile Asn Thr Val Arg Gly Pro Ile Thr Ile Ser Glu Ala Gly
1               5                   10                  15

Phe Thr Leu Thr His Glu His Ile Cys Gly Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Ala Gly Val Arg Thr Ile
    50                  55                  60

Val Asp Val Ser Thr Phe Asp Met Gly Arg Asp Val Ser Leu Leu Ala
65                  70                  75                  80

Glu Val Ser Arg Ala Ala Asp Val His Ile Val Ala Ala Thr Gly Leu
                85                  90                  95

Trp Ile Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Leu Ser Tyr Leu Thr Ala
        195                 200                 205

Leu Ala Ala Arg Gly Tyr Leu Ile Gly Leu Asp His Ile Pro Phe Ser
210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Trp Ala Phe Gly Leu
            260                 265                 270

Ser Ala Tyr Val Thr Asn Ile Met Asp Val Leu Asp Ser Val Asn Pro
        275                 280                 285

Asp Gly Met Ala Phe Ile Pro Leu Arg Val Ile Pro Phe Leu Arg Glu
290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330
```

<210> SEQ ID NO 64
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Para-fluoro Phe
<220> FEATURE:

<221> NAME/KEY: MOD_RES
<222> LOCATION: (26)..(26)
<223> OTHER INFORMATION: Para-fluoro Phe
<220> FEATURE:
<221> NAME/KEY: MOD_RES
<222> LOCATION: (31)..(31)
<223> OTHER INFORMATION: Para-fluoro Phe
<220> FEATURE:
<221> NAME/KEY: MOD_RES
<222> LOCATION: (38)..(39)
<223> OTHER INFORMATION: Para-fluoro Phe
<220> FEATURE:
<221> NAME/KEY: MOD_RES
<222> LOCATION: (70)..(70)
<223> OTHER INFORMATION: Para-fluoro Phe
<220> FEATURE:
<221> NAME/KEY: MOD_RES
<222> LOCATION: (115)..(116)
<223> OTHER INFORMATION: Para-fluoro Phe
<220> FEATURE:
<221> NAME/KEY: MOD_RES
<222> LOCATION: (145)..(145)
<223> OTHER INFORMATION: Para-fluoro Phe
<220> FEATURE:
<221> NAME/KEY: MOD_RES
<222> LOCATION: (182)..(182)
<223> OTHER INFORMATION: Para-fluoro Phe
<220> FEATURE:
<221> NAME/KEY: MOD_RES
<222> LOCATION: (270)..(270)
<223> OTHER INFORMATION: Para-fluoro Phe
<220> FEATURE:
<221> NAME/KEY: MOD_RES
<222> LOCATION: (293)..(293)
<223> OTHER INFORMATION: Para-fluoro Phe
<220> FEATURE:
<221> NAME/KEY: MOD_RES
<222> LOCATION: (301)..(301)
<223> OTHER INFORMATION: Para-fluoro Phe
<220> FEATURE:
<221> NAME/KEY: MOD_RES
<222> LOCATION: (323)..(323)
<223> OTHER INFORMATION: Para-fluoro Phe

<400> SEQUENCE: 64

Asp Arg Ile Asn Thr Val Arg Gly Pro Ile Thr Ile Ser Glu Ala Gly
1               5                   10                  15

Phe Thr Leu Thr His Glu His Ile Cys Phe Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Met Gly Arg Asp Val Ser Leu Leu Ala
65                  70                  75                  80

Glu Val Ser Arg Ala Ala Asp Val His Ile Val Ala Ala Thr Gly Leu
                85                  90                  95

Gly Trp Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Leu Val Ala Thr Thr Gly Lys Ala Thr Pro
    130                 135                 140

Phe Gln Glu Leu Val Leu Arg Ala Ala Arg Ala Ser Leu Ala Thr
145                 150                 155                 160

Gly Val Pro Val Thr Thr His Thr Ala Ala Ser Gln Arg Gly Gly Glu
                165                 170                 175

```
Gln Gln Ala Ala Ile Phe Glu Ser Glu Gly Leu Ser Pro Ser Arg Val
            180                 185                 190

Cys Ile Gly His Ser Asp Asp Thr Asp Leu Ser Tyr Leu Thr Ala
        195                 200                 205

Leu Ala Ala Arg Gly Tyr Leu Ile Gly Leu Asp Ala Ile Pro His Ser
        210                 215                 220

Ala Ile Gly Leu Glu Asp Asn Ala Ser Ala Ser Ala Trp Leu Gly Ile
225                 230                 235                 240

Arg Ser Trp Gln Thr Arg Ala Leu Leu Ile Lys Ala Leu Ile Asp Gln
                245                 250                 255

Gly Tyr Met Lys Gln Ile Leu Val Ser Asn Asp Tyr Ser Phe Gly Met
            260                 265                 270

Ser Ala Gly Val Thr Asn Ile Met Asp Val His Asp Ser Val Asn Pro
        275                 280                 285

Asp Gly Met Ala Phe Ile Pro Leu Arg Val Ile Pro Phe Leu Arg Glu
        290                 295                 300

Lys Gly Val Pro Gln Glu Thr Leu Ala Gly Ile Thr Val Thr Asn Pro
305                 310                 315                 320

Ala Arg Phe Leu Ser Pro Thr Leu Arg Ala Ser
                325                 330

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gatgtgtcga ctgccgatat cggtcg                                              26

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cgaccgatat cggcagtcga caca                                                24

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 67

His His His His His His
1               5
```